(12) United States Patent
    Abbas et al.

(10) Patent No.:    US 12,564,342 B2
(45) Date of Patent:      Mar. 3, 2026

(54) METHODS, SYSTEMS, AND DEVICES FOR THE DIAGNOSIS OF BEHAVIORAL DISORDERS, DEVELOPMENTAL DELAYS, AND NEUROLOGIC IMPAIRMENTS

(71) Applicant: Cognoa, Inc., Palo Alto, CA (US)

(72) Inventors: Abdelhalim Abbas, San Jose, CA (US); Jeffrey Ford Garberson, Redwood City, CA (US); Nathaniel E. Bischoff, Mountain View, CA (US); Erik Beall, Palo Alto, CA (US)

(73) Assignee: Cognoa, Inc., Palo Alto, CA (US)

( * ) Notice: Subject to any disclaimer, the term of this patent is extended or adjusted under 35 U.S.C. 154(b) by 529 days.

(21) Appl. No.: 17/761,532

(22) PCT Filed: Sep. 4, 2020

(86) PCT No.: PCT/US2020/049492
§ 371 (c)(1),
(2) Date: Mar. 17, 2022

(87) PCT Pub. No.: WO2021/046412
PCT Pub. Date: Mar. 11, 2021

(65) Prior Publication Data
US 2022/0369976 A1     Nov. 24, 2022

Related U.S. Application Data

(60) Provisional application No. 62/897,217, filed on Sep. 6, 2019.

(51) Int. Cl.
*G16H 20/70*       (2018.01)
*A61B 5/00*       (2006.01)
        (Continued)

(52) U.S. Cl.
CPC ............ *A61B 5/165* (2013.01); *A61B 5/1114* (2013.01); *A61B 5/1128* (2013.01); *A61B 5/163* (2017.08);
        (Continued)

(58) Field of Classification Search
CPC ..... A61B 5/165; A61B 5/1128; A61B 5/4088; A61B 5/4803; A61B 5/4836; A61B 5/7267
        (Continued)

(56) References Cited

U.S. PATENT DOCUMENTS 4,860,214 A    8/1989   Matsuda et al.
5,722,418 A    3/1998   Bro
        (Continued)

FOREIGN PATENT DOCUMENTS

CA        2857069 A1    5/2013
CN      101149767 A    3/2008
        (Continued)

OTHER PUBLICATIONS

Vaughan et al. (WO 2018/090009 Al) (Year: 2018).*
        (Continued)

*Primary Examiner* — Mohammed H Zuberi
*Assistant Examiner* — Ahamed I Nazar
(74) *Attorney, Agent, or Firm* — Wilson Sonsini Goodrich & Rosati

(57)           ABSTRACT

Described herein are methods, devices, systems, software, and platforms used to evaluate individuals such as children for behavioral disorders, developmental delays, and neurologic impairments. Specifically, described herein are methods, devices, systems, software, and platforms that are used to analyze video and/or audio recordings of individuals
        (Continued)

having one or more behavioral disorders, developmental delays, and neurologic impairments.

19 Claims, 13 Drawing Sheets

(51) Int. Cl.
    *A61B 5/11*           (2006.01)
    *A61B 5/16*           (2006.01)

(52) U.S. Cl.
    CPC ............ *A61B 5/168* (2013.01); *A61B 5/4088*
        (2013.01); *A61B 5/4803* (2013.01); *A61B*
        *5/4836* (2013.01); *A61B 5/681* (2013.01);
        *A61B 5/6898* (2013.01); *A61B 5/7264*
        (2013.01); *A61B 5/7275* (2013.01); *A61B*
        *5/744* (2013.01); *G16H 20/70* (2018.01); *A61B*
        *2503/06* (2013.01)

(58) Field of Classification Search
    USPC ........................................................ 382/128
    See application file for complete search history.

(56)           References Cited

U.S. PATENT DOCUMENTS

| | | |
|---|---|---|
| 6,186,145 B1 | 2/2001 | Brown |
| 6,569,093 B2 | 5/2003 | Iliff |
| 6,957,202 B2 | 10/2005 | Skaanning et al. |
| 7,043,439 B2 | 5/2006 | Jost et al. |
| 7,155,421 B1 | 12/2006 | Haldar |
| 7,311,666 B2 | 12/2007 | Stupp et al. |
| 7,958,066 B2 | 6/2011 | Pinckney et al. |
| 7,974,872 B2 | 7/2011 | Katayama et al. |
| 8,024,332 B2 | 9/2011 | Cao et al. |
| 8,655,817 B2 | 2/2014 | De et al. |
| 8,834,174 B2 | 9/2014 | Malik |
| 9,305,059 B1 | 4/2016 | Glickman et al. |
| 9,443,199 B2 | 9/2016 | Pinckney et al. |
| 9,443,205 B2 | 9/2016 | Wall |
| 10,052,057 B2 | 8/2018 | Klin et al. |
| 10,311,645 B1 | 6/2019 | Ravindran et al. |
| 10,478,112 B2 | 11/2019 | Wall |
| 10,687,751 B2 | 6/2020 | Wall |
| 10,874,355 B2 | 12/2020 | Vaughan et al. |
| 11,024,422 B2 | 6/2021 | Wall |
| 11,176,444 B2 | 11/2021 | Wall et al. |
| 2001/0034615 A1 | 10/2001 | Wilkinson et al. |
| 2002/0019747 A1 | 2/2002 | Ware et al. |
| 2002/0035486 A1 | 3/2002 | Huyn et al. |
| 2002/0042786 A1 | 4/2002 | Scarborough et al. |
| 2003/0032069 A1 | 2/2003 | Muraca |
| 2003/0191680 A1 | 10/2003 | Dewar |
| 2004/0015337 A1 | 1/2004 | Thomas et al. |
| 2004/0103001 A1 | 5/2004 | Mazar et al. |
| 2004/0147840 A1 | 7/2004 | Duggirala et al. |
| 2004/0197750 A1 | 10/2004 | Donaher et al. |
| 2004/0210159 A1 | 10/2004 | Kibar |
| 2004/0265784 A1 | 12/2004 | Stout |
| 2005/0075887 A1 | 4/2005 | Bernard et al. |
| 2005/0142524 A1 | 6/2005 | Simon et al. |
| 2005/0176057 A1 | 8/2005 | Bremer et al. |
| 2005/0187802 A1 | 8/2005 | Koeppel |
| 2005/0197988 A1 | 9/2005 | Bublitz |
| 2005/0209785 A1 | 9/2005 | Wells et al. |
| 2005/0216243 A1 | 9/2005 | Graham et al. |
| 2005/0260549 A1 | 11/2005 | Feierstein et al. |
| 2006/0009683 A1 | 1/2006 | Sakai et al. |
| 2006/0059145 A1 | 3/2006 | Henschke et al. |
| 2006/0078856 A1 | 4/2006 | Kellman |
| 2006/0282306 A1 | 12/2006 | Thissen-Roe |
| 2007/0118399 A1 | 5/2007 | Avinash et al. |
| 2007/0207449 A1 | 9/2007 | Feierstein |
| 2008/0014566 A1 | 1/2008 | Chapman et al. |
| 2008/0016024 A1 | 1/2008 | Andoh et al. |
| 2009/0007924 A1 | 1/2009 | Iliff |
| 2009/0016559 A1 | 1/2009 | Cleary |
| 2009/0083075 A1 | 3/2009 | Henschke et al. |
| 2009/0124886 A1 | 5/2009 | Wang et al. |
| 2009/0182578 A1 | 7/2009 | Ozersky |
| 2009/0259494 A1 | 10/2009 | Feder et al. |
| 2010/0068687 A1 | 3/2010 | Bertelsen |
| 2010/0177950 A1 | 7/2010 | Donovan et al. |
| 2010/0179928 A1 | 7/2010 | Hodgin |
| 2010/0189818 A1 | 7/2010 | Tsai |
| 2010/0280760 A1 | 11/2010 | Pi et al. |
| 2010/0332430 A1 | 12/2010 | Caraviello et al. |
| 2011/0145161 A1 | 6/2011 | Scarborough et al. |
| 2011/0218253 A1 | 9/2011 | Lange et al. |
| 2012/0004925 A1 | 1/2012 | Braverman et al. |
| 2012/0028816 A1 | 2/2012 | Warren et al. |
| 2012/0101852 A1 | 4/2012 | Albert |
| 2012/0102405 A1 | 4/2012 | Zuckerman et al. |
| 2012/0108909 A1 | 5/2012 | Slobounov et al. |
| 2012/0270199 A1 | 10/2012 | Malik |
| 2013/0159010 A1 | 6/2013 | Paty et al. |
| 2013/0184603 A1 | 7/2013 | Rothman |
| 2013/0262357 A1 | 10/2013 | Amarasingham et al. |
| 2013/0267441 A1 | 10/2013 | Momeni et al. |
| 2014/0006319 A1 | 1/2014 | Anand et al. |
| 2014/0063236 A1 | 3/2014 | Shreve et al. |
| 2014/0074848 A1 | 3/2014 | Kettunen et al. |
| 2014/0122109 A1 | 5/2014 | Ghanbari et al. |
| 2014/0141983 A1 | 5/2014 | Singh et al. |
| 2014/0148728 A1 | 5/2014 | Eizenman et al. |
| 2014/0219986 A1 | 8/2014 | Greene et al. |
| 2014/0223462 A1 | 8/2014 | Aimone et al. |
| 2014/0253876 A1 | 9/2014 | Klin et al. |
| 2014/0304200 A1 | 10/2014 | Wall |
| 2014/0330576 A1 | 11/2014 | Bauer |
| 2014/0343450 A1 | 11/2014 | Stack |
| 2015/0004588 A1 | 1/2015 | Vats et al. |
| 2015/0006192 A1 | 1/2015 | Sudharsan et al. |
| 2015/0099946 A1 | 4/2015 | Sahin |
| 2015/0119437 A1 | 4/2015 | Clark et al. |
| 2015/0154372 A1 | 6/2015 | Soenksen et al. |
| 2015/0315182 A1 | 11/2015 | Lee et al. |
| 2016/0022137 A1 | 1/2016 | Wetzel et al. |
| 2016/0135706 A1 | 5/2016 | Sullivan et al. |
| 2016/0140859 A1 | 5/2016 | Jiao et al. |
| 2016/0180038 A1 | 6/2016 | Clark et al. |
| 2016/0180248 A1 | 6/2016 | Regan |
| 2016/0209428 A1 | 7/2016 | Naviaux et al. |
| 2016/0232328 A1 | 8/2016 | Sklar et al. |
| 2017/0035792 A1 | 2/2017 | Montagnier et al. |
| 2017/0069216 A1 | 3/2017 | Vaughan et al. |
| 2017/0091423 A1 | 3/2017 | Kumar et al. |
| 2017/0160878 A1 | 6/2017 | Endo et al. |
| 2017/0169178 A1 | 6/2017 | Beehler et al. |
| 2017/0188930 A1* | 7/2017 | Lahvis .................. A61B 5/168 |
| 2017/0262609 A1 | 9/2017 | Perlroth et al. |
| 2017/0365101 A1 | 12/2017 | Samec et al. |
| 2018/0098724 A1 | 4/2018 | Lu et al. |
| 2018/0132780 A1 | 5/2018 | Saar |
| 2018/0184964 A1 | 7/2018 | Simon et al. |
| 2019/0019581 A1 | 1/2019 | Vaughan et al. |
| 2019/0038202 A1 | 2/2019 | Wall |
| 2019/0043610 A1 | 2/2019 | Vaughan |
| 2019/0043619 A1 | 2/2019 | Vaughan et al. |
| 2019/0088366 A1 | 3/2019 | Vaughan et al. |
| 2019/0244127 A1 | 8/2019 | Amado et al. |
| 2021/0068766 A1 | 3/2021 | Vaughan et al. |
| 2021/0133509 A1* | 5/2021 | Wall .................... A61B 5/4088 |
| 2021/0335489 A1 | 10/2021 | Wall |

FOREIGN PATENT DOCUMENTS

| | | |
|---|---|---|
| CN | 101499078 A | 8/2009 |
| CN | 101821741 A | 9/2010 |
| CN | 102663129 A | 9/2012 |
| CN | 102971755 A | 3/2013 |
| CN | 103473631 A | 12/2013 |
| CN | 103493054 A | 1/2014 |

(56) References Cited

FOREIGN PATENT DOCUMENTS

| | | | |
|---|---|---|---|
| CN | 103714261 A | 4/2014 | |
| CN | 104504297 A | 4/2015 | |
| EP | 0424869 | 2/1991 | |
| EP | 3483785 A1 | 5/2019 | |
| EP | 3941340 A1 | 1/2022 | |
| JP | 2001034688 A | 2/2001 | |
| JP | 2002318858 A | 10/2002 | |
| JP | 2007249878 A | 9/2007 | |
| JP | 2011255106 A | 12/2011 | |
| JP | 2012516463 A | 7/2012 | |
| JP | 2015228202 A | 12/2015 | |
| JP | 2017504087 A | 2/2017 | |
| JP | 2019504402 A | 2/2019 | |
| WO | WO-9521419 A1 | 8/1995 | |
| WO | WO-9705553 A1 | 2/1997 | |
| WO | WO-2008124138 A1 | 10/2008 | |
| WO | WO-2010059709 A2 | 5/2010 | |
| WO | WO-2012082056 A1 | 6/2012 | |
| WO | WO-2013062937 A2 | 5/2013 | |
| WO | WO-2015006364 A2 | 1/2015 | |
| WO | WO-2015066203 A2 | 5/2015 | |
| WO | WO-2016110804 A1 | 7/2016 | |
| WO | WO-2017027709 A1 | 2/2017 | |
| WO | WO-2017106770 A1 | 6/2017 | |
| WO | WO-2018090009 A1 | 5/2018 | |
| WO | WO-2020198065 A1 | 10/2020 | |
| WO | WO-2021046412 A1 | 3/2021 | |

OTHER PUBLICATIONS

PCT/US2020/049492 International Preliminary Report on Patentability dated Mar. 8, 2022.

PCT/US2020/049492 International Search Report and Written Opinion dated Dec. 10, 2020.

Artoni et al, Accessible education for autistic children: ABA-based didactic software, International Conference on Universal Access in Human-Computer Interaction (2011).

Atherton, G., et al., Autism through the ages: a mixed methods approach to understanding how age and age of diagnosis affect quality of life. J Autism Dev Disord, doi: 10.1007/s10803-021-05235-x.

Bailey, et al. Autism as a strongly genetic disorder: evidence from a British twin study. Psychol Med. Jan. 1995;25(1):63-77.

Bernier, et al. Psychopathology, families, and culture: autism. Child Adolesc Psychiatr Clin N Am. Oct. 2010;19(4):855-67.

Berument, et al. Autism screening questionnaire: diagnostic validity. Br J Psychiatry. Nov. 1999;175:444-51.

Breiman, Leo. Chapter 6: Medical Diagnosis and Prognosis. Classification and Regression Trees. Routledge (1984), pp. 174-346.

Breiman, Leo. Random Forests. Machine Learning, vol. 45, No. 1 (2001): pp. 5-32.

Cicchetti, et al. Reliability of the ADI-R: multiple examiners evaluate a single case. J Autism Dev Disord. Apr. 2008;38(4):764-70. Epub Dec. 5, 2007.

Cohen. Fast effective rule induction. Proceedings of the Twelfth International Conference on Machine Learning. (pp. 115-123) (1995).

Duda, et al. Testing the accuracy of an observation-based classifier for rapid detection of autism risk Transl Psychiatry. Aug. 12, 2014;4:e424.

Duda, et al. Testing the accuracy of an observation-based classifier for rapid detection of autism risk. Transl Psychiatry. Apr. 28, 2015;5:e556. (Addendum).

Duda, Marlena, et al. Clinical Evaluation of a Novel and Mobile Autism Risk Assessment. Journal of autism and developmental disorders vol. 46,6 (2016): 1953-1961.

Elder et al., Clinical impact of early diagnosis of autism on the prognosis and parent-child relationships. Psychology Research and Behavior Management 10: 283-292 (2017).

EP20860544.4 Extended European Search Report dated Aug. 25, 2023.

Fischbach, et al. The Simons Simplex Collection: a resource for identification of autism genetic risk factors. Neuron. Oct. 21, 2010;68(2):192-5.

Fisher et al., DISC Interviewer Manual. Section 2 Computerized Versions of the DISC (2006).

Frank, et al. A simple approach to ordinal prediction. European conference on Maching Learning; Freiburg, Germany, Springer-Verlag 2001:145-156.

Frank, et al. Data mining in bioinformatics using Weka. Bioinformatics. Oct. 12, 2004;20(15):2479-81. Epub Apr. 8, 2004.

Frank et al. Generating accurate rule sets without global optimization. In: Machine Learning: Proceedings of the Fifteenth International Conference: 1998; San Francisco, CA, Morgan Kaufmann Publishers (8 pgs).

Freund, et al. A decision-theoretic generalization of on-line learning and an application to boosting. Journal of computer and system sciences 55.1 (1997): 119-139.

Freund, et al. Experiments with a new boosting algorithm. In: Proceedings of the International Conference on Machine Learning: 1996, San Francisco, Morgan Kautinann: pp. 148-156.

Freund, et al. The alternating decision tree learning algorithm. In: Machine Learning: Proceedings of the Sixteenth International Conference. 1999, pp. 124-133.

Fusaro, et al. The potential of accelerating early detection of autism through content analysis of YouTube videos. PLOS One. Apr. 16, 2014;9(4):e93533.

Gaines, et al. Induction of ripple-down rules applied to modeling large databases. Journal of Intelligent Information Systems 5.3 (1995): 211-228.

Gama. Functional trees. Machine Learning 55:219-250 (2004).

Geschwind et al. The autism genetic resource exchange: a resource for the study of autism and related neuropsychiatric conditions. The American Journal of Human Genetics 69:463-466 (2001).

Gillberg et al. Early detection of autism. Diagnostic instruments for clinicians. European Child & Adolescent Psychiatry 5.2:67-74. (1996).

Golarai, G. et al. "Autism and the development of face processing", Clinical Neuroscience Research, 2006, vol. 6 , No. 3, pp. 145-106.

Gotham, et al. The Autism Diagnostic Observation Schedule: revised algorithms for improved diagnostic validity. J Autism Dev Disord. Apr. 2007;37(4):613-27. Epub Dec. 16, 2006.

Gura, et al. Autism spectrum disorder screening in primary care. J Dev Behav Pediatr. Jan. 2011;32(1):48-51.

Hall et al. The WEKA data mining software: an update. SIGKDD Explorations Newsletter 11:10-18 (2009).

Hirsch, S. et al. Development of a questionnaire weighted scoring system to target diagnostic examinations for asthma in adults: a modelling study. BMC Fam. Pract. 5:30 pp. 1-13 (2004) [E-pub Dec. 17, 2004].

Holmes et al. Multiclass alternating decision trees. Machine learning: ECML 2002. Springer Berlin Heidelberg, (pp. 161-172) (2002).

Holte. Very simple classification rules perform well on most commonly used datasets. Machine learning 11:63-91 (1993).

Howlin. Chapter 3—Identifying and assessing children with autism or asperger syndrome. Children with Autism and Asperger's Syndrome: A Guide for Practitioners and Carers. UK: John Wiley and Sons (1998) (pp. 52-75, 294-321).

Kobak et al. Web-based training in early autism screening: results from a pilot study. Telemed J E Health. Oct. 2011;17(8):640-4.

Kohavi. A study of cross-validation and bootstrap for accuracy estimation and model selection. In: Proceedings IJCAI-95: 1995: Montreal, Morgan Kaufmann, Los Altos, CA: 1137-1143.

Kosmicki, et al. Searching for a minimal set of behaviors for autism detection through feature selection-based machine learning. Transl Psychiatry. Feb. 24, 2015;5:e514.

Landwehr et al. Logistic model trees. Machine Learning 59:161-205 (2005).

Lord et al. Autism Diagnostic Interview-Revised: A revised version of a diagnostic interview for caregivers of individuals with possible pervasive developmental disorders. J Autism Dev Discord 24(5):659-685 (1994).

(56)          References Cited

OTHER PUBLICATIONS

Lord, et al. Autism diagnostic observation schedule: a standardized observation of communicative and social behavior. J Autism Dev Disord. Jun. 1989;19(2):185-212.

Lord et al. The Autism Diagnostic Observation Schedule—Generic: A Standard Measure of Social and Communication Deficits Associated with the Spectrum of Autism. J Autism Dev Discord 30(3):205-223 (2000).

Martin. Instance-Based learning: Nearest neighbor with generalization. Hamilton, New Zealand, University of Waikato (83 pgs) (1995).

Mayes et al., Autism and ADHD: Overlapping and discriminating symptoms. Research in Autism Spectrum Disorders 6(1) :277-285 (2012).

Moore et al. Cached Sufficient Statistics for Efficient Machine Learning with Large Datasets. JAIR 8:67-91 (1998).

Moyer, M.W., Gut Bacteria May Play a Role in Autism. Scientific American (20140: pp. 1-4.

Muangnak et al. Classification students with learning disabilities using naive bayes classifier and decision tree. The 6th International Conference on Networked Computing and Advanced Information Management. IEEE, 2010.

Ordonez, C. et al. Machine learning techniques applied to the determination of osteoporosis incidence in post-menopausal women. Mathematical and Computer Modelling, 50:673-679 (2009).

PCT/US2012/061422 International Search Report and Written Opinion dated May 24, 2013.

PCT/US2016/046557 International Search Report and Written Opinion dated Nov. 3, 2016.

PCT/US2016/067358 International Search Report and Written Opinion dated Apr. 13, 2017.

Pinto-Martin, et al. Screening strategies for autism spectrum disorders in pediatric primary care. J Dev Behav Pediatr. Oct. 2008;29(5):345-50.

Pisula, E. Parents of children with autism: review of current research. Arch Psychiatry Psychother, 2003, 5: 51-63.

Plajner et al., Bayesian Network Models for Adaptive Testing; Proceedings of the Twelfth Bayesian Modeling Applications Workshop, co-located with the 31st Conference on Uncertainty in Artificial Intelligence; Amsterdam, The Netherlands, Jul. 16, 2015; http://ceur-ws.org/Vol-1565/ (Year: 2015).

Planjner, Slide presentation on Bayesian Network Models for Adaptive Testing: Proceeding of the Twelfth Bayesian Modeling Applications Workshop (2015).

Quinlan. C4. 5: Programming for machine learning. Morgan Kauffmann (6 pgs) (1993).

Risi, et al. Combining information from multiple sources in the diagnosis of autism spectrum disorders. Journal of the American Academy of Child & Adolescent Psychiatry, 2006, 45(9): 1094-1103.

Robins, et al. The Modified Checklist for Autism in Toddlers: an initial study investigating the early detection of autism and pervasive developmental disorders. J Autism Dev Disord. Apr. 2001;31(2):131-44.

Rutter et al. Autism diagnostic interview-revised. Los Angeles, CA: Western Psychological Services 29:30 (2003).

Santosh et al. The construction and validation of a short form of the developmental, diagnostic and dimensional interview. Eur Child Adolesc Psychiatry. Aug. 2009;18(8):521-4.

Shattuck, et al. Timing of identification among children with an autism spectrum disorder: findings from a population-based surveillance study. J Am Acad Child Adolesc Psychiatry. May 2009;48(5):474-83.

Shi. Best-first decision tree learning. Master Thesis, The University of Waikato (120 pgs) (2007).

Skuse et al. The developmental, dimensional and diagnostic interview (3di): a novel computerized assessment for autism spectrum disorders. Journal of the American Academy of Child & Adolescent Psychiatry 43.5:548-558 (2004).

Sok et al.: Multivariate alternating decision trees, Pattern Recognition, 50:195-209 doi:10.1016/j.patcog.2015.08.014 (2016).

Tadevosyan-Leyfer, et al. A principal components analysis of the Autism Diagnostic Interview—Revised. J Am Acad Child Adolesc Psychiatry. Jul. 2003;42(7):864-72.

U.S. Appl. No. 17/690,977 Office Action dated Jan. 4, 2023.

U.S. Appl. No. 17/690,977 Office Action dated Sep. 14, 2022.

Van Stralen et al. Diagnostic methods I: sensitivity, specificity, and other measures of accuracy. Kidney Int. 75(12):1257-1263 (2009).

Wall et al. Use of artificial intelligence to shorten the behavioral diagnosis of autism. PLoS One. 2012;7(8):e43855.

Wall, et al. Use of machine learning to shorten observation-based screening and diagnosis of autism. Transl Psychiatry. Apr. 10, 2012;2:e100.

Ward et al, The Autistic Behavioural Indicators Instrument (ABII): Development and instrument utility in discriminating autistic disorder from speech and language impairment and typical development, Research in Autism Spectrum Disorders 4.1 (2010): 28-42.

Wenner, M. Gut Bacteria May Play a Role in Autism. Scientific American, pp. 1-4, Sep. 1, 2014.

Wiggins, et al. Examination of the time between first evaluation and first autism spectrum diagnosis in a population-based sample. J Dev Behav Pediatr. Apr. 2006;27(2 Suppl):S79-87.

Witten et al. Data Mining: Practical Machine Learning Tools and Techniques with Java Implementations. Morgan Kaufmann, Amsterdam, Second Edition (558 pgs) (Oct. 2005).

Witten et al, Weka: Practical Machine Learning Tools and Techniques with Java Implementations, University of Waikato, Department of Computer Science, 1999. (4pp).

* cited by examiner

201

210

205

215

"Hello, my name is Susan. Today I am going to tell you a really cool story. Are you ready for it? Tell me as loud as you can, are you ready?! Okay, let's listen to it now!"

One night, a young woman was walking through the airport...

"Here's a picture for you to tell your own story. Where are they and what are they doing?"

METHODS, SYSTEMS, AND DEVICES FOR THE DIAGNOSIS OF BEHAVIORAL DISORDERS, DEVELOPMENTAL DELAYS, AND NEUROLOGIC IMPAIRMENTS

CROSS-REFERENCE

This application is a National Stage Entry of International Application No. PCT/US2020/049492, filed Sep. 4, 2020, which claims the benefit of U.S. Provisional Application No. 62/897,217, filed Sep. 6, 2019, each of which is hereby incorporated by reference in its entirety.

BACKGROUND

Numerous individuals including children suffer from behavioral disorders, developmental delays, and neurologic impairments. Examples of these conditions include attention deficit hyperactivity disorder ("ADHD"), autism (including autism spectrum disorder), and speech disorders.

Healthcare providers typically evaluate behavioral disorders, developmental delays, and neurologic impairments using traditional observational techniques.

SUMMARY

Described herein are methods, devices, systems, software, and platforms used to evaluate individuals such as children for behavioral disorders, developmental delays, and neurologic impairments. Specifically, described herein are methods, devices, systems, software, and platforms that are used to analyze video and/or audio of individuals having one or more behavioral disorders, developmental delays, and neurologic impairments. As compared to traditional techniques for evaluating individuals for one or more behavioral disorders, developmental delays, and neurologic impairments, the methods, devices, systems, software, and platforms described herein are highly efficient and accurate.

Traditionally, behavioral disorders, developmental delays, and neurologic impairments are difficult to evaluate and in particular difficult to evaluate accurately and efficiently because of the relatedness of these condition types. That is, each condition type category (e.g., behavioral disorders, developmental delays, and neurologic impairments) contain a plurality of condition types, and the condition types are typically related within the same condition type category and across different condition type categories so that the condition types have one or more overlapping symptoms or other identifiers.

The conditions within each single condition type category (e.g., behavioral disorders, developmental delays, or neurologic impairments) tend to be related so that they have one or more overlapping symptoms or other identifiers. For example, a first developmental delay such as autism has overlap with a second developmental delay such as speech delay. As a result, autism can be difficult to differentiate from speech delay using traditional techniques, which may result in an individual receiving an incorrect diagnosis. Similarly, an individual with both developmental delays (e.g., autism and speech delay) may only have one developmental delay diagnosed as opposed to both because the presence of one of the developmental delays may be missed in the presence of the other (e.g., speech delay may be missed in individual with diagnosis of autism and vice versa).

Likewise, the condition types within multiple condition type categories tend to be related so that they have one or more overlapping symptoms or other identifiers. For example, ADHD, a type of behavioral disorder, tends to have overlap with autism, a type of developmental delay. As a result, ADHD can be difficult to differentiate from autism using traditional techniques, which may result in an individual receiving an incorrect diagnosis. Similarly, an individual with both ADHD and autism may only have one diagnosed as opposed to both because the presence of one of the condition types may be missed in the presence of the other (e.g., autism may be missed in an individual with a diagnosis of ADHD and vice versa).

Traditional techniques for evaluating individuals with at least one condition type selected from the condition type categories of behavioral disorders, developmental delays, and neurologic impairments typically involve repeated assessment of individuals often with collection of multiple types of data including various test findings. For example, traditional techniques may involve relatively long question sets that are administered to individuals and/or their caretakers. As such, in addition to being inaccurate due to the relatedness of the condition types assessed (as explained above), traditional techniques are typically time consuming and inefficient.

In contrast to traditional techniques, described herein are methods, devices, systems, software, and platforms for accurately and efficiently assessing individuals for at least one condition type selected from the condition type categories of behavioral disorders, developmental delays, and neurologic impairments. More specifically, described herein are methods, devices, systems, software, and platforms for analyzing video and/or audio data of individuals for at least one condition type selected from the condition type categories of behavioral disorders, developmental delays, and neurologic impairments in order to determine if said at least one condition type is present or likely to be present in said individual.

Some embodiments described herein analyze an input source such as a video and/or audio source of an individual or related to said individual in order to identify a behavioral unit. For example, a video recorded using a mobile computing device is analyzed to identify a behavioral unit within the video and/or audio that is recorded. One or more behavioral units make up a higher order behavior. For example, a behavioral unit comprising a smile, in some situations, makes up the higher order behavior of happiness. In addition, in some embodiments, behavioral units are mapped over time to create a timeline that in some embodiments provides additional context with respect to one or more behavioral units. In some embodiments, a behavioral pattern comprises higher order behaviors and/or behavioral units mapped over time.

In some embodiments of a method as described herein, video and/or audio of an individual is recorded with a mobile computing device and analyzed using a machine learning software module which identifies one or more behavioral units within the video and/or audio that is recorded. In some embodiments, a behavioral unit is associated with one or more other behavioral units. In some embodiments, a behavioral unit is classified as making up a higher order behavior using a machine learning classifier or other type of machine learning modeling.

In some embodiments, a behavioral unit that is identified is tagged or labeled with respect to, for example, the timing of the occurrence of the behavioral unit within the video and/or audio that is recorded. In some embodiments, a tag or label is used by a machine learning software module to contextualize a behavioral unit.

In general, some embodiments described herein, include a machine learning software module trained to receive input comprising video and/or audio data, analyze the video and/or audio data, and generate an output comprising at least one of an identified behavioral unit, an identified plurality of behavioral units, a map of a plurality of behavioral units, an identified higher order behavior, an identified plurality of higher order behaviors, and a map of a plurality of higher order behaviors.

Disclosed herein is a computer-implemented method for automated video assessment of an individual, said method comprising: receiving, with a computing device, input data comprising at least one of audio or video information for said individual on which is performed said automated video assessment; identifying, with said computing device, a plurality of behavioral units within said input data, wherein each behavioral unit of said plurality of behavioral units comprises a behavior that makes up a higher order behavior; and identifying, with said computing device, said higher order behavior based on at least one behavioral unit from said plurality of behavioral units. In some embodiments, at least one of said plurality of behavioral units comprises a machine detectable movement or sound made by the individual. In some embodiments, at least one of said plurality of behavioral units comprises a facial movement, body movement, or sound made by the individual. In some embodiments, at least one of said higher order behaviors comprise a verbal or non-verbal communication. In some embodiments, said non-verbal communication comprises a facial expression, posture, gesture, eye contact, or touch. In some embodiments, identifying said plurality of behavioral units comprises analyzing said video information using facial recognition to detect one or more facial movement. In some embodiments, identifying said plurality of behavioral units comprises analyzing said audio information using audio recognition to detect one or more sounds, words, or phrases. In some embodiments, identifying higher order behavior comprises generating a timeline of a plurality of behavioral units. In some embodiments, said method further comprises generating said behavioral pattern based on said timeline of said plurality of behavioral units or higher order behaviors. In some embodiments, said input data further comprises information or responses provided by a caretaker of said individual. In some embodiments, said information or responses comprises answers to questions. In some embodiments, said method further comprises generating a prediction comprising a positive classification, a negative classification, or an inconclusive classification with respect to a behavioral disorder, developmental delay, or neurologic impairment. In some embodiments, the method further comprises obtaining said at least one of audio or video information through a mobile computing device. In some embodiments, said mobile computing device comprises a smartphone, tablet computer, laptop, smartwatch or other wearable computing device. In some embodiments, obtaining said at least one of audio or video information comprises capturing video footage or an audio recording of said individual or of interactions between a person and said individual. In some embodiments, said behavioral disorder, developmental delay, or neurologic impairment comprises pervasive development disorder (PDD), autism spectrum disorder (ASD), social communication disorder, restricted repetitive behaviors, interests, and activities (RRBs), autism ("classical autism"), Asperger's Syndrome ("high functioning autism), PDD-not otherwise specified (PDD-NOS, "atypical autism"), attention deficit disorder (ADD), attention deficit and hyperactivity disorder (ADHD), speech and language delay, obsessive compulsive disorder (OCD), depression, schizophrenia, Alzheimer's disease, dementia, intellectual disability, or learning disability. In some embodiments, said behavioral disorder, developmental delay, or neurologic impairment is autism spectrum disorder or autism. In some embodiments, identifying said plurality of behavioral units within said input data and/or identifying said higher order behavior is done using a machine learning software module. In some embodiments, said machine learning algorithm is a supervised learning algorithm. In some embodiments, said machine learning software module is selected from nearest neighbor, naive Bayes, decision tree, linear regression, support vector machine, or neural network. In some embodiments, the method further comprises providing an activity configured to elicit a response by said individual, said response comprising said input data comprising at least one of said audio or said video information. In some embodiments, said activity provides a virtual character guiding said individual through the activity. In some embodiments, said higher order behavior or a pattern of behavior of the individual comprises articulation of speech sounds, fluency, voice, ability to understand and decode language, ability to produce and use language, or any combination thereof. In some embodiments, identifying said plurality of behavioral units comprises analyzing said audio information using audio recognition to detect one or more sounds, words, or phrases. In some embodiments, the method further comprises adjusting said activity based on said higher order behavior identified for said individual. In some embodiments, said activity is dynamically adjusted while the individual is engaged with the activity.

Disclosed herein is a device for automated assessment of an individual, said device comprising: a display; and a processor configured with instructions to: receive input data comprising at least one of audio or video information for said individual on which is performed said automated video assessment; identify a plurality of behavioral units within said input data, wherein each behavioral unit of said plurality of behavioral units comprises a behavior that makes up a higher order behavior; and identify said higher order behavior based on at least one behavioral unit from said plurality of behavioral units. In some embodiments, at least one of said plurality of behavioral units comprises a machine detectable movement or sound made by the individual. In some embodiments, at least one of said plurality of behavioral units comprises a facial movement, body movement, or sound made by the individual. In some embodiments, at least one of said higher order behaviors comprise a verbal or non-verbal communication. In some embodiments, said non-verbal communication comprises a facial expression, posture, gesture, eye contact, or touch. In some embodiments, identify said plurality of behavioral units comprises analyzing said video information using facial recognition to detect one or more facial movement. In some embodiments, identify said plurality of behavioral units comprises analyzing said audio information using audio recognition to detect one or more sounds, words, or phrases. In some embodiments, identify higher order behavior comprises generating a timeline of a plurality of behavioral units. In some embodiments, said processor is further configured with instructions to generate said behavioral pattern based on said timeline of said plurality of behavioral units or higher order behaviors. In some embodiments, said input data further comprises information or responses provided by a caretaker of said individual. In some embodiments, said information or responses comprises answers to questions. In some embodiments, said processor is further configured with instructions to generate a prediction comprising a positive classification, a negative classification, or an inconclusive classification with respect to a behavioral disorder, developmental delay, or neurologic impairment. In some embodiments, said device is a mobile computing device. In some embodiments, said mobile computing device comprises a smartphone, tablet computer, laptop, smartwatch or other wearable computing device. In some embodiments, obtain said at least one of audio or video information comprises capturing video footage or an audio recording of said individual or of interactions between a person and said individual. In some embodiments, said behavioral disorder, developmental delay, or neurologic impairment comprises pervasive development disorder (PDD), autism spectrum disorder (ASD), social communication disorder, restricted repetitive behaviors, interests, and activities (RRBs), autism ("classical autism"), Asperger's Syndrome ("high functioning autism), PDD-not otherwise specified (PDD-NOS, "atypical autism"), attention deficit disorder (ADD), attention deficit and hyperactivity disorder (ADHD), speech and language delay, obsessive compulsive disorder (OCD), depression, schizophrenia, Alzheimer's disease, dementia, intellectual disability, or learning disability. In some embodiments, said behavioral disorder, developmental delay, or neurologic impairment is autism spectrum disorder or autism. In some embodiments, identify said plurality of behavioral units within said input data and/or identify said higher order behavior is done using a machine learning software module. In some embodiments, said machine learning algorithm is a supervised learning algorithm. In some embodiments, said machine learning software module is selected from nearest neighbor, naive Bayes, decision tree, linear regression, support vector machine, or neural network. In some embodiments, said processor is further configured with instructions to provide an activity configured to elicit a response by said individual, said response comprising said input data comprising at least one of said audio or said video information. In some embodiments, said activity provides a virtual character guiding said individual through the activity. In some embodiments, said higher order behavior or a pattern of behavior of the individual comprises articulation of speech sounds, fluency, voice, ability to understand and decode language, ability to produce and use language, or any combination thereof. In some embodiments, identify said plurality of behavioral units comprises analyzing said audio information using audio recognition to detect one or more sounds, words, or phrases. In some embodiments, said processor is further configured with instructions to adjust said activity based on said higher order behavior identified for said individual. In some embodiments, said activity is dynamically adjusted while the individual is engaged with the activity.

Disclosed herein is a platform for automated behavior assessment of an individual, said platform comprising: a capturing application comprising video and/or audio recording software for use on a device capable of capturing one or more video or audio recordings of the individual; an assessment application configured to receive video and/or audio recordings from the capturing application and analyze the video and/or audio recordings with one or more machine learning algorithms configured to: receive input data comprising at least one of audio or video information for said individual on which is performed said automated video assessment; identify a plurality of behavioral units within said input data, wherein each behavioral unit of said plurality of behavioral units comprises a behavior that makes up a higher order behavior; and identify said higher order behavior based on at least one behavioral unit from said plurality of behavioral units. In some embodiments, at least one of said plurality of behavioral units comprises a machine detectable movement or sound made by the individual. In some embodiments, at least one of said plurality of behavioral units comprises a facial movement, body movement, or sound made by the individual. In some embodiments, at least one of said higher order behaviors comprise a verbal or non-verbal communication. In some embodiments, said non-verbal communication comprises a facial expression, posture, gesture, eye contact, or touch. In some embodiments, identify said plurality of behavioral units comprises analyzing said video information using facial recognition to detect one or more facial movement. In some embodiments, identify said plurality of behavioral units comprises analyzing said audio information using audio recognition to detect one or more sounds, words, or phrases. In some embodiments, identify higher order behavior comprises generating a timeline of a plurality of behavioral units. In some embodiments, said assessment application is configured to generate said behavioral pattern based on said timeline of said plurality of behavioral units or higher order behaviors. In some embodiments, said input data further comprises information or responses provided by a caretaker of said individual. In some embodiments, said information or responses comprises answers to questions. In some embodiments, said assessment application is configured to generate a prediction comprising a positive classification, a negative classification, or an inconclusive classification with respect to a behavioral disorder, developmental delay, or neurologic impairment. In some embodiments, said device is a mobile computing device. In some embodiments, said mobile computing device comprises a smartphone, tablet computer, laptop, smartwatch or other wearable computing device. In some embodiments, obtain said at least one of audio or video information comprises capturing video footage or an audio recording of said individual or of interactions between a person and said individual. In some embodiments, said behavioral disorder, developmental delay, or neurologic impairment comprises pervasive development disorder (PDD), autism spectrum disorder (ASD), social communication disorder, restricted repetitive behaviors, interests, and activities (RRBs), autism ("classical autism"), Asperger's Syndrome ("high functioning autism), PDD-not otherwise specified (PDD-NOS, "atypical autism"), attention deficit disorder (ADD), attention deficit and hyperactivity disorder (ADHD), speech and language delay, obsessive compulsive disorder (OCD), depression, schizophrenia, Alzheimer's disease, dementia, intellectual disability, or learning disability. In some embodiments, said behavioral disorder, developmental delay, or neurologic impairment is autism spectrum disorder or autism. In some embodiments, identify said plurality of behavioral units within said input data and/or identify said higher order behavior is done using a machine learning software module. In some embodiments, said machine learning algorithm is a supervised learning algorithm. In some embodiments, said machine learning software module is selected from nearest neighbor, naive Bayes, decision tree, linear regression, support vector machine, or neural network. In some embodiments, said assessment application is configured to provide an activity configured to elicit a response by said individual, said response comprising said input data comprising at least one of said audio or said video information. In some embodiments, said activity provides a virtual character guiding said individual through the activity. In some embodiments, said higher order behavior or a pattern of behavior of the individual comprises articulation of speech sounds, fluency, voice, ability to understand and decode language, ability to produce and use language, or any combination thereof. In some embodiments, identify said plurality of behavioral units comprises analyzing said audio information using audio recognition to detect one or more sounds, words, or phrases. In some embodiments, said assessment application is configured to adjust said activity based on said higher order behavior identified for said individual. In some embodiments, said activity is dynamically adjusted while the individual is engaged with the activity.

Disclosed herein is a computer-implemented method for automated behavior assessment of an individual, said method comprising: receiving, with a computer device, input data comprising at least one of audio or video information for said individual; processing, with said computer device, said input data to identify a plurality of behavioral units; evaluating, with said computer device, said plurality of behavioral units to determine one or more higher order behaviors; evaluating, with said computer device, said plurality of behavioral units and higher order behaviors over time to determine one or more behavioral patterns; and generating, with said computer device, a prediction of a behavioral disorder, developmental delay, or neurologic impairment based on one or more behavioral patterns. In some embodiments, at least one of said plurality of behavioral units comprises an observable movement or sound made by the individual. In some embodiments, at least one of said plurality of behavioral units comprises a facial movement, body movement, or sound made by the individual. In some embodiments, at least one of said higher order behavior corresponds to a verbal or non-verbal communication. In some embodiments, said non-verbal communication comprises a facial expression, posture, gesture, eye contact, or touch. In some embodiments, evaluating said plurality of behavioral units comprises analyzing said video information using facial recognition to detect one or more facial movement. In some embodiments, identifying said plurality of behavioral units comprises analyzing said audio information using audio recognition to detect one or more sounds, words, or phrases. In some embodiments, identifying one or more higher order behaviors comprises generating a timeline of a plurality of behavioral units. In some embodiments, the behavioral pattern is generated based on a timeline of said plurality of behavioral units and/or higher order behaviors. In some embodiments, said input data further comprises information or responses provided by a caretaker of said individual. In some embodiments, said information or responses comprises answers to questions. In some embodiments, said prediction comprises a positive classification, a negative classification, or an inconclusive classification with respect to said behavioral disorder, developmental delay, or neurologic impairment. In some embodiments, the device obtains said at least one of audio or video information through a mobile computing device. In some embodiments, said mobile computing device comprises a smartphone, tablet computer, laptop, smartwatch or other wearable computing device. In some embodiments, obtaining said at least one of audio or video information comprises capturing video footage or an audio recording of said individual or of interactions between a person and said individual. In some embodiments, said behavioral disorder, developmental delay, or neurologic impairment comprises pervasive development disorder (PDD), autism spectrum disorder (ASD), social communication disorder, restricted repetitive behaviors, interests, and activities (RRBs), autism ("classical autism"), Asperger's Syndrome ("high functioning autism"), PDD-not otherwise specified (PDD-NOS, "atypical autism"), attention deficit disorder (ADD), attention deficit and hyperactivity disorder (ADHD), speech and language delay, obsessive compulsive disorder (OCD), depression, schizophrenia, Alzheimer's disease, dementia, intellectual disability, or learning disability. In some embodiments, said behavioral disorder, developmental delay, or neurologic impairment is autism spectrum disorder or autism. In some embodiments, one or more of the feature detection algorithm, higher order behavior detection algorithm, behavioral pattern detection algorithm or assessment algorithm is a supervised learning algorithm. In some embodiments, one or more of the feature detection algorithm, higher order behavior detection algorithm, behavioral pattern detection algorithm or assessment algorithm is a supervised learning algorithm is selected from nearest neighbor, naive Bayes, decision tree, linear regression, support vector machine, or neural network. In some embodiments, the device further comprises a camera or microphone capable of capturing audio or video recordings. In some embodiments, the processor is further configured with instructions to provide an activity configured to elicit a response by said individual, said response comprising said input data comprising at least one of said audio or said video information. In some embodiments, said activity provides a virtual character guiding said individual through the activity. In some embodiments, said higher order behaviors or behavioral patterns of said individual comprises articulation of speech sounds, fluency, voice, ability to understand and decode language, ability to produce and use language, or any combination thereof. In some embodiments, the processor is further configured with instructions to identify said plurality of behavioral units by analyzing said audio information using audio recognition to detect one or more sounds, words, or phrases. In some embodiments, the processor is further configured with instructions to adjust said activity based on said higher order behaviors or behavioral patterns determined for said individual. In some embodiments, said activity is dynamically adjusted while the individual is engaged with the activity.

Disclosed herein is a device for automated behavior assessment of an individual, said device comprising: a display; and a processor configured with instructions to: receive input data comprising at least one of audio or video information for said individual; process said input data to identify a plurality of behavioral units; evaluate said plurality of behavioral units to determine one or more higher order behaviors; evaluate said plurality of behavioral units and higher order behaviors over time to determine one or more behavioral patterns; and generate a prediction of a behavioral disorder, developmental delay, or neurologic impairment based on one or more behavioral patterns. In some embodiments, at least one of said plurality of behavioral units comprises an observable movement or sound made by the individual. In some embodiments, at least one of said plurality of behavioral units comprises a facial movement, body movement, or sound made by the individual. In some embodiments, at least one of said higher order behavior corresponds to a verbal or non-verbal communication. In some embodiments, said non-verbal communication comprises a facial expression, posture, gesture, eye contact, or touch. In some embodiments, evaluating said plurality of behavioral units comprises analyzing said video information using facial recognition to detect one or more facial movement. In some embodiments, identifying said plurality of behavioral units comprises analyzing said audio information using audio recognition to detect one or more sounds, words, or phrases. In some embodiments, identifying one or more higher order behaviors comprises generating a timeline of a plurality of behavioral units. In some embodiments, the behavioral pattern is generated based on a timeline of said plurality of behavioral units and/or higher order behaviors. In some embodiments, said input data further comprises information or responses provided by a caretaker of said individual. In some embodiments, said information or responses comprises answers to questions. In some embodiments, said prediction comprises a positive classification, a negative classification, or an inconclusive classification with respect to said behavioral disorder, developmental delay, or neurologic impairment. In some embodiments, the device obtains said at least one of audio or video information through a mobile computing device. In some embodiments, said mobile computing device comprises a smartphone, tablet computer, laptop, smartwatch or other wearable computing device. In some embodiments, obtaining said at least one of audio or video information comprises capturing video footage or an audio recording of said individual or of interactions between a person and said individual. In some embodiments, said behavioral disorder, developmental delay, or neurologic impairment comprises pervasive development disorder (PDD), autism spectrum disorder (ASD), social communication disorder, restricted repetitive behaviors, interests, and activities (RRBs), autism ("classical autism"), Asperger's Syndrome ("high functioning autism), PDD-not otherwise specified (PDD-NOS, "atypical autism"), attention deficit disorder (ADD), attention deficit and hyperactivity disorder (ADHD), speech and language delay, obsessive compulsive disorder (OCD), depression, schizophrenia, Alzheimer's disease, dementia, intellectual disability, or learning disability. In some embodiments, said behavioral disorder, developmental delay, or neurologic impairment is autism spectrum disorder or autism. In some embodiments, one or more of the feature detection algorithm, higher order behavior detection algorithm, behavioral pattern detection algorithm or assessment algorithm is a supervised learning algorithm. In some embodiments, one or more of the feature detection algorithm, higher order behavior detection algorithm, behavioral pattern detection algorithm or assessment algorithm is a supervised learning algorithm is selected from nearest neighbor, naive Bayes, decision tree, linear regression, support vector machine, or neural network. In some embodiments, the device further comprises a camera or microphone capable of capturing audio or video recordings. In some embodiments, the processor is further configured with instructions to provide an activity configured to elicit a response by said individual, said response comprising said input data comprising at least one of said audio or said video information. In some embodiments, said activity provides a virtual character guiding said individual through the activity. In some embodiments, said higher order behaviors or behavioral patterns of said individual comprises articulation of speech sounds, fluency, voice, ability to understand and decode language, ability to produce and use language, or any combination thereof. In some embodiments, the processor is further configured with instructions to identify said plurality of behavioral units by analyzing said audio information using audio recognition to detect one or more sounds, words, or phrases. In some embodiments, the processor is further configured with instructions to adjust said activity based on said higher order behaviors or behavioral patterns determined for said individual. In some embodiments, said activity is dynamically adjusted while the individual is engaged with the activity.

Disclosed herein is a platform for automated behavior assessment of an individual, said platform comprising: a capturing application comprising video and/or audio recording software for use on a device capable of capturing one or more video or audio recordings of the individual; an assessment application configured to receive video and/or audio recordings from the capturing application and analyze the video and/or audio recordings with one or more machine learning algorithms configured to: receive input data comprising at least one of audio or video information for said individual; process said input data and identify a plurality of behavioral units; evaluate said plurality of behavioral units to determine one or more higher order behaviors; evaluate said plurality of behavioral units and higher order behaviors over time to determine one or more behavioral patterns; generate a prediction of a behavioral disorder, developmental delay, or neurologic impairment based on one or more behavioral patterns; and provide a user with the prediction of behavioral disorder, developmental delay, or neurologic impairment present in the individual; a health care provider application configured to receive data from the assessment application and display recommendations for treatment. In some embodiments, at least one of said plurality of behavioral units comprises an observable movement or sound made by the individual. In some embodiments, at least one of said plurality of behavioral units comprises a facial movement, body movement, or sound made by the individual. In some embodiments, at least one of said higher order behavior corresponds to a verbal or non-verbal communication. In some embodiments, said non-verbal communication comprises a facial expression, posture, gesture, eye contact, or touch. In some embodiments, evaluating said plurality of behavioral units comprises analyzing said video information using facial recognition to detect one or more facial movement. In some embodiments, identifying said plurality of behavioral units comprises analyzing said audio information using audio recognition to detect one or more sounds, words, or phrases. In some embodiments, identifying one or more higher order behaviors comprises generating a timeline of a plurality of behavioral units. In some embodiments, the behavioral pattern is generated based on a timeline of said plurality of behavioral units and/or higher order behaviors. In some embodiments, said input data further comprises information or responses provided by a caretaker of said individual. In some embodiments, said information or responses comprises answers to questions. In some embodiments, said prediction comprises a positive classification, a negative classification, or an inconclusive classification with respect to said behavioral disorder, developmental delay, or neurologic impairment. In some embodiments, the platforms obtains said at least one of audio or video information through a mobile computing device. In some embodiments, said mobile computing device comprises a smartphone, tablet computer, laptop, smartwatch or other wearable computing device. In some embodiments, obtaining said at least one of audio or video information comprises capturing video footage or an audio recording of said individual or of interactions between a person and said individual. In some embodiments, said behavioral disorder, developmental delay, or neurologic impairment comprises pervasive development disorder (PDD), autism spectrum disorder (ASD), social communication disorder, restricted repetitive behaviors, interests, and activities (RRBs), autism ("classical autism"), Asperger's Syndrome ("high functioning autism), PDD-not otherwise specified (PDD-NOS, "atypical autism"), attention deficit disorder (ADD), attention deficit and hyperactivity disorder (ADHD), speech and language delay, obsessive compulsive disorder (OCD), depression, schizophrenia, Alzheimer's disease, dementia, intellectual disability, or learning disability. In some embodiments, said behavioral disorder, developmental delay, or neurologic impairment is autism spectrum disorder or autism. In some embodiments, one or more of the feature detection algorithm, higher order behavior detection algorithm, behavioral pattern detection algorithm or assessment algorithm is a supervised learning algorithm. In some embodiments, one or more of the feature detection algorithm, higher order behavior detection algorithm, behavioral pattern detection algorithm or assessment algorithm is a supervised learning algorithm is selected from nearest neighbor, naive Bayes, decision tree, linear regression, support vector machine, or neural network. In some embodiments, the platform is capable of capturing one or more video or audio recordings of the individual is equipped with the capturing application and assessment application. In some embodiments, the assessment application is configured to provide an interactive module comprising an activity configured to elicit a response by said individual, said response comprising said input data comprising at least one of said audio or said video information. In some embodiments, said activity provides a virtual character guiding said individual through the activity. In some embodiments, said higher order behaviors or behavioral patterns of said individual comprises articulation of speech sounds, fluency, voice, ability to understand and decode language, ability to produce and use language, or any combination thereof. In some embodiments, the assessment application is configured to identify said plurality of behavioral units by analyzing said audio information using audio recognition to detect one or more sounds, words, or phrases. In some embodiments, the interactive module is configured to adjust said activity based on said higher order behaviors or behavioral patterns determined for said individual. In some embodiments, said activity is dynamically adjusted while the individual is engaged with the activity.

Disclosed herein is a computer-implemented method for automated assessment and therapy for speech or language of an individual, said method comprising: (a) providing, with one or more computer devices, an interactive module prompting said individual to engage in one or more digital therapeutic activities; (b) receiving, with said one or more computer devices, input data comprising at least one of audio or video information for said individual engaged in said one or more digital therapeutic activities; (c) identifying, with said one or more computer devices, a plurality of behavioral units within said input data, wherein each behavioral unit of said plurality of behavioral units comprises a behavior that makes up a higher order behavior; (d) identifying, with said one or more computer devices, said higher order behavior based on at least one behavioral unit from said plurality of behavioral units; and (e) adjusting, with said one or more computer devices, at least one of said one or more digital therapeutic activities based on said higher order behavior. In some embodiments, at least one of said plurality of behavioral units comprises a machine detectable movement or sound made by the individual. In some embodiments, at least one of said plurality of behavioral units comprises a facial movement, body movement, or sound made by the individual. In some embodiments, at least one of said higher order behaviors comprise a verbal or non-verbal communication. In some embodiments, said non-verbal communication comprises a facial expression, posture, gesture, eye contact, or touch. In some embodiments, identifying said plurality of behavioral units comprises analyzing said video information using facial recognition to detect one or more facial movement. In some embodiments, identifying said plurality of behavioral units comprises analyzing said audio information using audio recognition to detect one or more sounds, words, or phrases. In some embodiments, identifying higher order behavior comprises generating a timeline of a plurality of behavioral units. In some embodiments, the method further comprises generating a behavioral pattern based on said timeline of said plurality of behavioral units or higher order behaviors. In some embodiments, said input data further comprises information or responses provided by a caretaker of said individual. In some embodiments, said information or responses comprises answers to questions. In some embodiments, the method further comprises generating a prediction comprising a positive classification, a negative classification, or an inconclusive classification with respect to a behavioral disorder, developmental delay, or neurologic impairment. In some embodiments, the method further comprises obtaining said at least one of audio or video information through a mobile computing device. In some embodiments, said mobile computing device comprises a smartphone, tablet computer, laptop, smartwatch or other wearable computing device. In some embodiments, obtaining said at least one of audio or video information comprises capturing video footage or an audio recording of said individual or of interactions between a person and said individual. In some embodiments, said behavioral disorder, developmental delay, or neurologic impairment comprises pervasive development disorder (PDD), autism spectrum disorder (ASD), social communication disorder, restricted repetitive behaviors, interests, and activities (RRBs), autism ("classical autism"), Asperger's Syndrome ("high functioning autism), PDD-not otherwise specified (PDD-NOS, "atypical autism"), attention deficit disorder (ADD), attention deficit and hyperactivity disorder (ADHD), speech and language delay, obsessive compulsive disorder (OCD), depression, schizophrenia, Alzheimer's disease, dementia, intellectual disability, or learning disability. In some embodiments, said behavioral disorder, developmental delay, or neurologic impairment is autism spectrum disorder or autism. In some embodiments, identifying said plurality of behavioral units within said input data and/or identifying said higher order behavior is done using a machine learning software module. In some embodiments, said machine learning algorithm is a supervised learning algorithm. In some embodiments, said machine learning software module is selected from nearest neighbor, naive Bayes, decision tree, linear regression, support vector machine, or neural network. In some embodiments, said one or more digital therapeutic activities are configured to elicit a response by said individual, wherein said response is detected as said input data comprising at least one of said audio or said video information. In some embodiments, said activity provides a virtual character guiding said individual through the activity. In some embodiments, said higher order behavior or a pattern of behavior of the individual comprises articulation of speech sounds, fluency, voice, ability to understand and decode language, ability to produce and use language, or any combination thereof. In some embodiments, identifying said plurality of behavioral units comprises analyzing said audio information using audio recognition to detect one or more sounds, words, or phrases. In some embodiments, said activity is dynamically adjusted while the individual is engaged with the activity.

Disclosed herein is a device for automated assessment and therapy for speech or language of an individual, said device comprising: (a) a display; and (b) a processor configured with instructions to: (i) provide an interactive module prompting said individual to engage in one or more digital therapeutic activities; (ii) receive input data comprising at least one of audio or video information for said individual engaged in said one or more digital therapeutic activities; (iii) identify a plurality of behavioral units within said input data, wherein each behavioral unit of said plurality of behavioral units comprises a behavior that makes up a higher order behavior; (iv) identify said higher order behavior based on at least one behavioral unit from said plurality of behavioral units; and (v) adjust at least one of said one or more digital therapeutic activities based on said higher order behavior. In some embodiments, at least one of said plurality of behavioral units comprises a machine detectable movement or sound made by the individual. In some embodiments, at least one of said plurality of behavioral units comprises a facial movement, body movement, or sound made by the individual. In some embodiments, at least one of said higher order behaviors comprise a verbal or non-verbal communication. In some embodiments, said non-verbal communication comprises a facial expression, posture, gesture, eye contact, or touch. In some embodiments, identify said plurality of behavioral units comprises analyzing said video information using facial recognition to detect one or more facial movement. In some embodiments, identify said plurality of behavioral units comprises analyzing said audio information using audio recognition to detect one or more sounds, words, or phrases. In some embodiments, identify higher order behavior comprises generating a timeline of a plurality of behavioral units. In some embodiments, the processor is further configured with instructions to generate a behavioral pattern based on said timeline of said plurality of behavioral units or higher order behaviors. In some embodiments, said input data further comprises information or responses provided by a caretaker of said individual. In some embodiments, said information or responses comprises answers to questions. In some embodiments, the processor is further configured with instructions to generate a prediction comprising a positive classification, a negative classification, or an inconclusive classification with respect to a behavioral disorder, developmental delay, or neurologic impairment. In some embodiments, the processor is further configured with instructions to obtain said at least one of audio or video information through a mobile computing device. In some embodiments, said mobile computing device comprises a smartphone, tablet computer, laptop, smartwatch or other wearable computing device. In some embodiments, obtain said at least one of audio or video information comprises capturing video footage or an audio recording of said individual or of interactions between a person and said individual. In some embodiments, said behavioral disorder, developmental delay, or neurologic impairment comprises pervasive development disorder (PDD), autism spectrum disorder (ASD), social communication disorder, restricted repetitive behaviors, interests, and activities (RRBs), autism ("classical autism"), Asperger's Syndrome ("high functioning autism), PDD-not otherwise specified (PDD-NOS, "atypical autism"), attention deficit disorder (ADD), attention deficit and hyperactivity disorder (ADHD), speech and language delay, obsessive compulsive disorder (OCD), depression, schizophrenia, Alzheimer's disease, dementia, intellectual disability, or learning disability. In some embodiments, said behavioral disorder, developmental delay, or neurologic impairment is autism spectrum disorder or autism. In some embodiments, identify said plurality of behavioral units within said input data and/or identify said higher order behavior is done using a machine learning software module. In some embodiments, said machine learning algorithm is a supervised learning algorithm. In some embodiments, said machine learning software module is selected from nearest neighbor, naive Bayes, decision tree, linear regression, support vector machine, or neural network. In some embodiments, said one or more digital therapeutic activities are configured to elicit a response by said individual, wherein said response is detected as said input data comprising at least one of said audio or said video information. In some embodiments, said activity provides a virtual character guiding said individual through the activity. In some embodiments, said higher order behavior or a pattern of behavior of the individual comprises articulation of speech sounds, fluency, voice, ability to understand and decode language, ability to produce and use language, or any combination thereof. In some embodiments, identify said plurality of behavioral units comprises analyzing said audio information using audio recognition to detect one or more sounds, words, or phrases. In some embodiments, said activity is dynamically adjusted while the individual is engaged with the activity.

Disclosed herein is a platform for automated assessment and therapy for speech or language of an individual, said platform comprising: (a) a capturing application comprising video and/or audio recording software for use on a device capable of capturing one or more video or audio recordings of the individual; (b) an assessment and therapy application configured to: (i) provide an interactive module prompting said individual to engage in one or more digital therapeutic activities; (ii) receive input data comprising said one or more video or audio recordings for said individual engaged in said one or more digital therapeutic activities; (iii) identify a plurality of behavioral units within said input data, wherein each behavioral unit of said plurality of behavioral units comprises a behavior that makes up a higher order behavior; (iv) identify said higher order behavior based on at least one behavioral unit from said plurality of behavioral units; and (v) adjust at least one of said one or more digital therapeutic activities based on said higher order behavior. In some embodiments, at least one of said plurality of behavioral units comprises a machine detectable movement or sound made by the individual. In some embodiments, at least one of said plurality of behavioral units comprises a facial movement, body movement, or sound made by the individual. In some embodiments, at least one of said higher order behaviors comprise a verbal or non-verbal communication. In some embodiments, said non-verbal communication comprises a facial expression, posture, gesture, eye contact, or touch. In some embodiments, identify said plurality of behavioral units comprises analyzing said video information using facial recognition to detect one or more facial movement. In some embodiments, identify said plurality of behavioral units comprises analyzing said audio information using audio recognition to detect one or more sounds, words, or phrases. In some embodiments, identify higher order behavior comprises generating a timeline of a plurality of behavioral units. In some embodiments, the processor is further configured with instructions to generate a behavioral pattern based on said timeline of said plurality of behavioral units or higher order behaviors. In some embodiments, said input data further comprises information or responses provided by a caretaker of said individual. In some embodiments, said information or responses comprises answers to questions. In some embodiments, the processor is further configured with instructions to generate a prediction comprising a positive classification, a negative classification, or an inconclusive classification with respect to a behavioral disorder, developmental delay, or neurologic impairment. In some embodiments, the processor is further configured with instructions to obtain said at least one of audio or video information through a mobile computing device. In some embodiments, said mobile computing device comprises a smartphone, tablet computer, laptop, smartwatch or other wearable computing device. In some embodiments, obtain said at least one of audio or video information comprises capturing video footage or an audio recording of said individual or of interactions between a person and said individual. In some embodiments, said behavioral disorder, developmental delay, or neurologic impairment comprises pervasive development disorder (PDD), autism spectrum disorder (ASD), social communication disorder, restricted repetitive behaviors, interests, and activities (RRBs), autism ("classical autism"), Asperger's Syndrome ("high functioning autism), PDD-not otherwise specified (PDD-NOS, "atypical autism"), attention deficit disorder (ADD), attention deficit and hyperactivity disorder (ADHD), speech and language delay, obsessive compulsive disorder (OCD), depression, schizophrenia, Alzheimer's disease, dementia, intellectual disability, or learning disability. In some embodiments, said behavioral disorder, developmental delay, or neurologic impairment is autism spectrum disorder or autism. In some embodiments, identify said plurality of behavioral units within said input data and/or identify said higher order behavior is done using a machine learning software module. In some embodiments, said machine learning algorithm is a supervised learning algorithm. In some embodiments, said machine learning software module is selected from nearest neighbor, naive Bayes, decision tree, linear regression, support vector machine, or neural network. In some embodiments, said one or more digital therapeutic activities are configured to elicit a response by said individual, wherein said response is detected as said input data comprising at least one of said audio or said video information. In some embodiments, said activity provides a virtual character guiding said individual through the activity. In some embodiments, said higher order behavior or a pattern of behavior of the individual comprises articulation of speech sounds, fluency, voice, ability to understand and decode language, ability to produce and use language, or any combination thereof. In some embodiments, identify said plurality of behavioral units comprises analyzing said audio information using audio recognition to detect one or more sounds, words, or phrases. In some embodiments, said activity is dynamically adjusted while the individual is engaged with the activity.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

Figure 1:
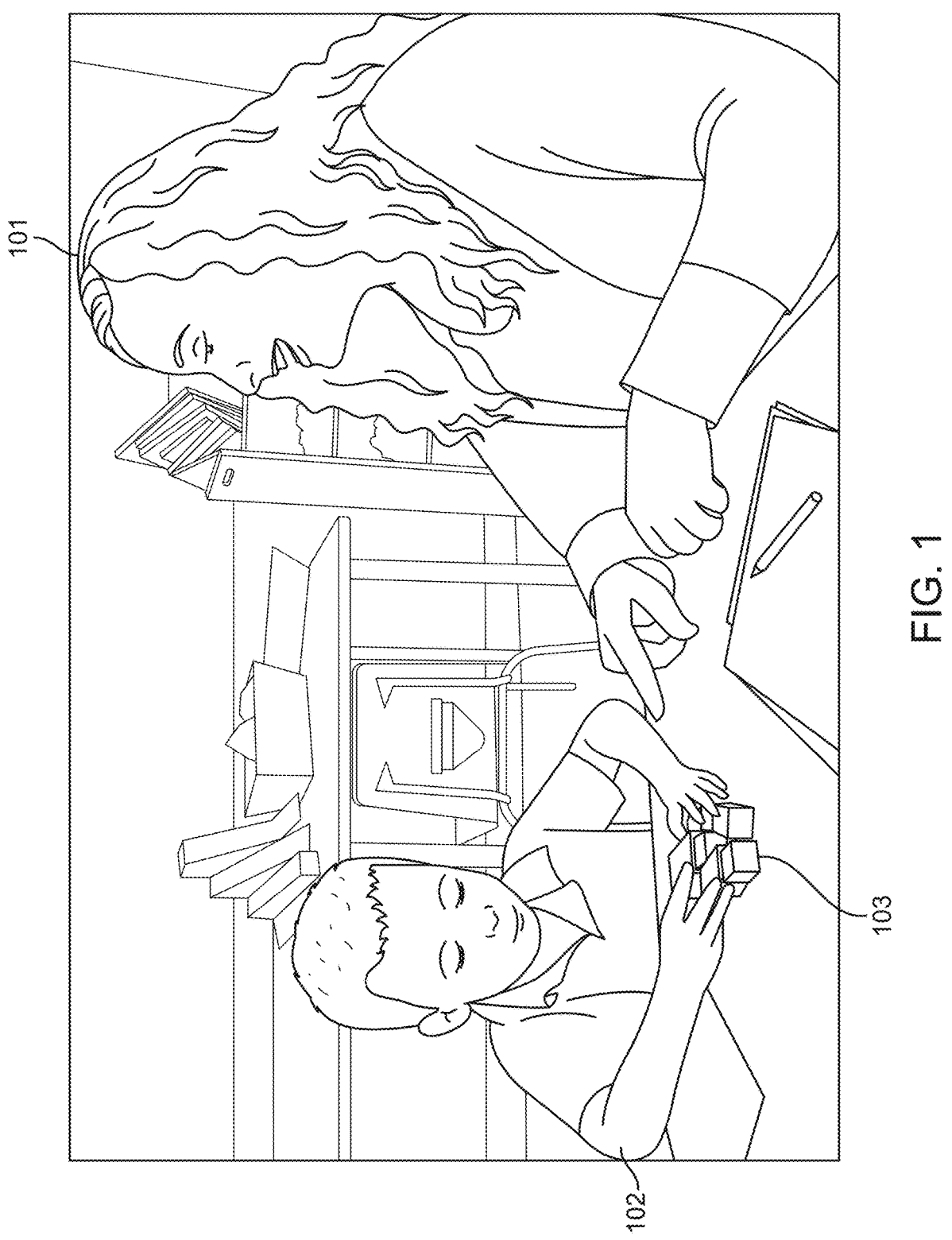
FIG. 1 shows a representation of an image in which behavioral units are extracted.

Described herein are methods, devices, systems, software, and platforms used to evaluate individuals, such as children, for behavioral disorders, developmental delays, and neurologic impairments.

In embodiments described herein at least one video and/or audio input is analyzed and at least one behavioral unit is identified therein. A behavioral unit, in some embodiments, is paired or associated with one or more other behavioral units.

In some embodiments, one or more behavioral units make up a higher order behavior that is identified.

In some embodiments, a timeline representation is generated showing a position of at least one behavioral unit within said timeline.

Behavioral Unit

In general, a behavioral unit is an observable feature or parameter displayed by an individual being assessed for a particular condition and/or an individual interacting with said individual. In addition, a behavioral unit, is typically a particular feature or parameter that is useful in assessing an individual being assessed for a particular condition. That is, one or more behavioral units that are observed or determined are then used in embodiments of the methods, devices, systems, software, and platforms described herein to reach an assessment with respect to a presence of a condition in an individual being assessed.

In some embodiments, a behavioral unit is a movement or a sound of an individual that is detectable and clinically relevant to the likely presence or absence of a condition such as a behavioral disorder, developmental delay, or neurologic impairment.

In general, in embodiments of the methods, devices, systems, software, and platforms described herein one or more behavioral units are used in the evaluation of an individual to determine the likelihood of the presence or absence of one or more behavioral disorders, developmental delays, and neurologic impairments in said individual.

In some embodiments, a behavioral unit is a movement or sound of the individual under analysis. In some embodiments, the movement or sound is observed by a human watching a video or audio recording of the individual. In some embodiments, the movement or sound is detected by a software module analyzing a video or audio recording of the individual. In some embodiments, the behavior is in response to a stimulus such as a question, game, or event.

For example, a child being assessed for a behavioral disorder, developmental delay, and/or a neurologic impairment is asked a question and responds with a smile, a shrug and an audible "I don't know." In some embodiments, the smile, shrug and verbal communication are each individual behavioral units.

In some embodiments, a behavioral unit is a facial movement made by the individual being assessed or another individual interacting with the individual being assessed. In some embodiments, behavior units, such as facial movements, used to determine higher order behavior, such as facial expressions.

Non-liming examples of facial movements that make up a behavioral unit include smiling, frowning, moving the lips, raising or lowering lip elevation, tightening of the lips, biting the lips, opening or closing the mouth, pursing the lips, puckering the lips, licking of the lips, showing teeth, showing the inside of the mouth, moving the face in association with speech or verbal noise, furrowing the brow, a relaxing the brow, sucking or buffing of the cheeks, raising the brow, lowering the brow, raising the inner brow, lowering the inner brow, raising the outer brow, lowering the outer brow, raising on or both cheeks, raising one or both eyelids, lowering one or both eyelids, tightening one or both eyelids, pulling the lip corners, depressing the lip corners, raising the chin, showing the tongue, stretching the lips, pressing the lips, parting the lips, dropping the jaw, stretching the mouth, looking in any direction, rolling the eyes, crossing the eyes, widening the eyes, focusing the eyes, looking past someone or something, quickly moving the eyes, blinking, fluttering of the eyelids, winking, closing the eyes, opening the eyes, squinting or slitting the eyes, moving the nose, dilating the nostrils, constricting the nostrils, sniffing, puffing the cheeks, blowing air out the mouth, sucking in the cheeks, bulging the cheeks with the tongue, clenching the jaw, moving the jaw sideways, thrusting the jaw out or in, swallowing, chewing, moving the ears, or twitching the face. In some embodiments, some examples, such as a smile, can be a behavior units it their own right, while being a combination of other individual behavior units. For example, a smile may comprise individual behavioral units such as the showing of teeth, squinting eyes, raising of the eyebrows, dimpling cheeks, raising of skin lines on the forehead, and skin coloration.

In some embodiments, a behavioral unit is a body movement made by an individual being assessed or an individual interacting with the individual being assessed.

Non-liming examples of body movements that make up a behavioral unit include turning of the head left or right, turning the head up or down, tilting the head, thrusting the head forward, pulling the head back, shaking the head back and forth, nodding, shaking the head up and down, tilting the head side to side, shrugging the shoulders, shivering, trembling, moving the arms, moving the legs, moving the hands, moving the feet, moving the abdomen, moving the neck, moving the shoulders, moving the pelvis, craning the neck, stretching the neck, whipping of the head and neck, moving repetitively, tapping the fingers, opening and closing hands repetitively, gesturing with one or both hands, waiving with one or both hands, pointing with fingers, moving involuntarily, losing balance, compensating for lost balance, writhing of the face or extremities, jerking of the body or extremities, rocking of the body, flapping of the arms, spinning of the body, running or walking back and forth, staring at lights, biting of the lips or body, banging of the head, the inability to move one side of the body without moving the other, moving with slowness or lethargy, shifting eye gaze frequently, bending joints, striking another person or object, controlling an object in an unusual manner, or tensing of the muscles. In some embodiments, some examples, such as rocking of the body, can be a behavior units it their own right, while being a combination of other individual behavior units. For example, rocking of the body may comprise individual behavioral units such as moving the body, thrusting the head forward, and pulling the head back.

In some embodiments, a behavioral unit is a sound made by an individual being assessed or an individual interacting with the individual being assessed. In some embodiments, the sound is made by the mouth, body, or object in the individual's control.

Non-liming examples of sounds made by mouth that make up a behavioral unit include verbal communication, clearly audible and understandable speech, unclear speech, whispering, muttering, speech directed toward or away from the recording device, talking, shouting, singing, humming, speech elevated in volume, speech that modulates in volume or tone, speech with voice quivers, quick speech, slow speech, babbling, crying, coughing, sneezing, snorting, burping, groaning, giggling, panting, hiccuping, audible exhaling or inhaling, clicking of the tongue, whistling, wheezing, imitations of noises, imitations of flatulence, imitations of animals, musical or rhythmic noise, speaking of various languages, snoring, sighing, slurping, or yawning. In some embodiments, sound made by the body comprises clapping of hands, slapping or striking of one or both hands against a body part or object, cracking bones such as fingers or neck, tapping of fingers or feet, or flapping arms.

In some embodiments, the sounds, words, or phrases made by an individual are used to determine a level of speech and/or language development. Such sounds can include speech sounds or phonemes that make up the units of words. The sounds can be detected and/or analyzed based on the specific language settings (e.g., speech detection is customized for the language). Non-limiting examples of speech sounds or phonemes in English include /b/, /pbp/, /m/, /n/, /t/, /d/, /k/, /g/, /f/, /s/, /y/, /æ/, /e/, and /oʊ/. English can include 24 consonant phonemes and 20 vowel phonemes. Alternatively, non-English speech sounds or phonemes are used to determine a level of speech and/or language development.

Non-liming examples of sounds made by one or more objects in an individual's control and that make up a behavioral unit include striking an object against another object, another being, or the individual, or causing an object to otherwise make a noise. In some embodiments, the behavioral unit is a qualitative observation about a sound made by the individual. For example, the presence of a stutter, slur, or lisp, monotonic speech, or abnormal intonation.

In some embodiments, a behavioral unit comprises a lack of facial movement, body movement or sound by the individual. For example, if the individual is asked a question directly, and does not respond with a facial movement, body movement, or sound, the unresponsiveness to a stimulus may be a behavioral unit.

Behavioral Unit Identification

Behavioral units are identified from observable analysis sessions with individuals being evaluated for certain conditions. Observable analysis sessions may comprise one or more question sessions where an individual being evaluated is asked diagnostic questions. Observable analysis sessions may comprise one or more sessions where an individual being evaluated is observed in an interaction with another individual. In some cases, observable analysis sessions comprise an interactive activity (e.g., a storytelling activity) during which an individual is guided through the activity and prompted or otherwise elicited to provide feedback, which serves as input data that is analyzed to identify behavioral units.

Observation may be of a live or real-time session or of a recording of an observable session. For example, a human may observe a live session. For example, a machine may carry out real-time video and/or audio analysis of a session using video or audio recording technology, wherein the video and/or audio that is inputted into the machine via the video and/or audio recording technology is analyzed by a software module in real time, wherein the software module is a component of the machine. Similarly, a human or machine may be used to analyze a recorded video or audio session that was recorded at another time.

Analysis of observable sessions includes the identification of one or more behavioral units. One or more behavioral units, in some embodiments, are used to determine a presence or absence of a behavioral disorder, developmental delay, or neurologic impairment.

In some embodiments, behavioral units are identified by a human (referred to as a "human identifier"). In some embodiments, behavioral units are created by human identification of facial movements, body movements, or sounds in video and audio data of an individual. In some embodiments, a human analyzes images of individuals and identifies the location of the behavioral unit in each image. In some embodiments, the human watches a video of an individual and identifies the location of the behavioral unit in the video with respect to location in the frame and time of appearance. In some embodiments, image analysis software is used by the human to provide clearer image data on which to base the behavioral unit. In some embodiments, a human analyses a sound of an individual and identifies the time period in which the behavioral unit is present. In some embodiments, audio extraction and analysis software is used to aid in filtering out background noise and unrelated noise to provide clearer behavioral unit data.

In some embodiments, behavioral units are identified by a software module. In some embodiments, behavioral units are created by software module identification of facial movements, body movements, or sounds in video and audio data of an individual. In some embodiments, a software module analyzes images of individuals and identifies the location of the behavioral unit in each image. In some embodiments, a software module analyzes images of individuals and identifies the location of the behavioral unit in each sound. In some embodiments, a software module utilizes recognition software to determine the faces and bodies of individuals. In some embodiments, identifying said plurality of behavioral units comprises analyzing said video information using facial recognition to detect one or more facial movement. In some embodiments, identifying said plurality of behavioral units comprises analyzing said audio information using audio recognition to detect one or more sounds, words, or phrases.

In some embodiments, a behavioral unit is any visible or audible observation determinable by a computerized algorithm analyzing video data or audible. In some embodiments, the video or audio data has a temporal component, such the video or audio frames are timestamped and analyzed with relation to video and audio data within a certain temporal proximity of the timestamped video or audio data. In some embodiments, a behavioral unit may be a body movement or micro-expression that is imperceptible to a human observer but observable by an algorithm analyzing video or audio data over time. For example, a computer analysis of a video of an individual is conducted in which blinking has been identified as a behavior unit. A human observer does not identify any abnormalities in the eyes, while the computer algorithm indicates that the individual blinks at an abnormal rate or blinking rate increases when the individual is asked certain questions. Alternatively, in some embodiments, one or more behavioral units in an audio or video data are analyzed by each image or sound clip without relation to other images or sound clips. For example, a particular grimacing facial movement has been previously identified as a behavioral unit associated with individuals with an autism disorder. A computer analysis of an image of the individual indicates the presence or absence of the behavioral unit without respect to the time the grimace occurs, and the data is used in subsequent analysis or the individual to determine a diagnosis.

In some embodiments, behavioral units are identified by both human and software module identification. In some embodiments, behavioral units are identified by software or a human identifier, and the identified behavioral units are then used as training data for the training of a machine learning software module, so that the trained machine learning software module is then used to identify behavioral units in new images and sounds. For example, in some embodiments, software (or a human) is utilized to identify the form of an individual in a video or image and associate a behavioral unit that is identified with a location on the body of an individual. For example, software (or a human) may be used to determine whether or not a human face is present in a video or image being analyzed. If a human face is present, and a behavioral unit is identified in an area identified as a human face, the behavioral unit may be mapped with the location on the face. For example, software (or a human) identifies eyebrow movement across many videos images as behavioral units using software that then selects the location in the video images in which the eyebrow movements are present. The software (or a human) determines that the images contain human faces and maps the eyebrow locations onto the human faces. The identified and mapped images are used to train a machine learning algorithm. As eyebrows must be mapped to a location on a face, the algorithm is better able to determine whether new video images containing objects that appear similar to eyebrows are to be recognized as such.

In some embodiments, identifying behavioral units comprises analyzing video information using facial recognition software to detect one or more facial movements. In some embodiments, identifying said behavioral units comprises analyzing audio information using audio recognition software to detect one or more sounds, words, or phrases. In some embodiments, said audio recognition software analyzes said audio information to detect sounds, words, or phrases corresponding to speech activity. A speech detection algorithm can be utilized to detect speech activity by performing one or more steps such as pre-processing the audio information to remove background noise (e.g., spectral subtraction), identifying behavioral units that correspond to sounds, words, or phrases indicative of speech activity, or classifying a portion of the audio information as speech or non-speech activity. In some embodiments, the speech detection algorithm detects the phonemes that make up spoken words, analyzes the sequence of phonemes to identify words and phrases, and identifies the presence or absence of any speech and/or language impairments or defects via assessment of aspects of speech and/or language such as, for example, articulation of speech sounds, fluency, voice, ability to understand and decode language, and the ability to produce and use language. In some embodiments, speech that is detected is parsed into constituent units and compared to a baseline or reference standard and/or evaluated using one or more speech or language metrics to generate an assessment or determine a level of the speech or language of a subject.

Evaluation of Individuals for Specific Conditions Using One or More Identified Behavioral Units In some embodiments, a software module uses the one or more behavioral units that are identified to determine whether one or more conditions are likely to be present in an individual being evaluated. A condition that is determined to be present may comprise one or more behavioral disorders, developmental delays, and neurologic impairments.

In some embodiments, the software module is configured to identify the likelihood of a presence of one or more behavioral disorders comprising Attention Deficit Hyperactivity Disorder (ADHD), Oppositional Defiant Disorder (ODD), Autism Spectrum Disorder (ASD), Anxiety Disorders, Depression, Bipolar Disorders, Learning Disorders or Disabilities, or Conduct Disorder. In some embodiments, an Attention Deficit Hyperactivity Disorder comprises Predominantly Inattentive ADHD, Predominantly Hyperactive-impulsive type ADHD, or Combined Hyperactive-impulsive and Inattentive type ADHD. In some embodiments, Autism Spectrum Disorder comprises Autistic Disorder (classic autism), Asperger Syndrome, Pervasive Developmental Disorder (atypical autism), or Childhood disintegrative disorder. In some embodiments, Anxiety Disorders comprise Panic Disorder, Phobia, Social Anxiety Disorder, Obsessive-Compulsive Disorder, Separation Anxiety Disorder, Illness Anxiety Disorder (Hypochondria), or Post-Traumatic Stress Disorder. In some embodiments, Depression comprises Major Depression, Persistent Depressive Disorder, Bipolar Disorder, Seasonal Affective Disorder, Psychotic Depression, Peripartum (Postpartum) Depression, Premenstrual Dysphoric Disorder, 'Situational' Depression, or Atypical Depression. In some embodiments, Bipolar Disorders comprise Bipolar I Disorder, Bipolar II Disorder, Cyclothymic Disorder or Bipolar Disorder due to another medical or substance abuse disorder. In some embodiments, learning disorders comprise Dyslexia, Dyscalculia, Dysgraphia, Dyspraxia (Sensory Integration Disorder), Dysphasia/Aphasia, Auditory Processing Disorder, or Visual Processing Disorder. In some embodiments, behavioral disorder is a disorder defined in any edition of the Diagnostic and Statistical Manual of Mental Disorders (DSM).

In some embodiments, the software module is configured to determine the likelihood of the presence or absence of one or more developmental delays comprising Autism Spectrum Disorder, Mental Retardation, Cerebral Palsy, Down Syndrome, Failure to Thrive, Muscular Dystrophy, Hydrocephalus, Developmental Coordination Disorder, Cystic Fibrosis, Fetal Alcohol Syndrome, Homocystinuria, Tuberous Sclerosis, Abetalipoproteinemia, Phenylketonuria, speech delays, gross motor delays, fine motor delays, social delays, emotional delays, behavioral delays, or cognitive delays. In some embodiments, Mental Retardation comprises Adrenoleukodystrophy, Ito Syndrome, Acrodysostosis, Huntington's Disease, Aarskog Syndrome, Aicardi Syndrome or Tay-Sachs Disease. In some embodiments, Cerebral Palsy comprises Spastic Cerebral Palsy, Dyskinetic Cerebral Palsy, Hypotonic Cerebral Palsy, Ataxic Cerebral Palsy, or Mixed Cerebral Palsy. In some embodiments, Autism Spectrum Disorder comprises Autistic Disorder (classic autism), Asperger Syndrome, Pervasive Developmental Disorder (atypical autism), or Childhood disintegrative disorder. In some embodiments, Down Syndrome comprises Trisomy 21, Mosaicism, or Translocation. In some embodiments, Muscular Dystrophy comprises Duchenne muscular dystrophy, Becker muscular dystrophy, Congenital muscular dystrophy, Myotonic dystrophy, Facioscapulohumeral muscular dystrophy, Oculopharyngeal muscular dystrophy, Distal muscular dystrophy, or Emery-Dreifuss muscular dystrophy.

In some embodiments, the software module is configured to determine the likelihood of the presence or absence of one or more neurological impairments comprising Amyotrophic Lateral Sclerosis, Arteriovenous Malformation, brain aneurysm, brain tumors, Dural Arteriovenous Fistulae, Epilepsy, headache, memory disorders, Multiple Sclerosis, Parkinson's Disease, Peripheral Neuropathy, Post-Herpetic Neuralgia, spinal cord tumor, stroke, Alzheimer's Disease, Corticobasal Degeneration, Creutzfeldt-Jakob Disease, Frontotemporal Dementia, Lewy Body Dementia, Mild Cognitive Impairment, Progressive Supranuclear Palsy, or Vascular Dementia.

In some embodiments, the behavioral disorder, developmental delay, or neurologic impairment comprises pervasive development disorder (PDD), autism spectrum disorder (ASD), social communication disorder, restricted repetitive behaviors, interests, and activities (RRBs), autism ("classical autism"), Asperger's Syndrome ("high functioning autism), PDD-not otherwise specified (PDD-NOS, "atypical autism"), attention deficit disorder (ADD), attention deficit and hyperactivity disorder (ADHD), speech and language delay, obsessive compulsive disorder (OCD), depression, schizophrenia, Alzheimer's disease, dementia, intellectual disability, or learning disability. In some embodiments, the behavioral disorder, developmental delay, or neurologic impairment is autism spectrum disorder or autism.

FIG. 1 shows a representation of an image in which behavioral units are extracted. A questioner or caretaker 101 interacts with the individual 102 under examination. The questioner or caretaker may ask the individual to interact with an object 103 or accomplish a task. Alternatively, the questioner or caretaker may seek responses from the subject. A movement or sound of an individual that is software module detectable and clinically relevant to the likely presence or absence of a behavioral disorder, developmental delay, or neurologic impairment is registered as a behavioral unit. For example, the child's eye movements, the child's verbal communication, and the child's face and hand movements may be behavioral units. In some cases, a child provides responses through an automated assessment and/or therapeutic process. For example, a child may be provided a digital device comprising an interactive module (e.g., storytime) that provides an interactive digital experience and elicits and/or solicits response or feedback from the child (e.g., video, audio, or other user input such as via buttons/touchscreen), which can be analyzed to identify behavioral units used to determine higher order behavior and/or evaluate the child's status or progress (e.g., level of speech or language development with respect to expected development at a given age).

Higher Order Behaviors

In some embodiments, a higher order behavior is determined by compiling a plurality of behavioral units. Higher order behavior that is identified by the methods, devices, systems, software, and platforms described herein, in some embodiments, is an output that is provided and serves as at least a portion of an evaluation that is generated for an individual being evaluated. In some embodiments, identifying higher order behavior from collections of behavioral units observed provides a way to organize, contextualize, and/or better evaluate individual behavioral units.

In some embodiments, a higher order behavior comprises a verbal communication, non-verbal communication, lack of communication, display of thoughts or emotion, control over movement, direction of gaze or attention, or direction of verbal communication. For example, the video of an individual may comprise the behavioral units of a smile, laughter and clapping. The higher order behavior displayed may be happiness or joy. In some embodiments, a verbal communication can include signs or symptoms of speech or language impairment, delay, or disorder. Examples include impairments or defects in articulation of speech sounds, fluency, voice, ability to understand and decode language, and the ability to produce and use language. In some embodiments, the higher order behavior comprising verbal communication of an individual is analyzed using an algorithm (e.g., a machine learning algorithm) to determine whether the individual has one or more behavioral disorders, developmental delays, and neurologic impairments or a sign or symptom thereof, for example, a speech or language defect or delay relative to the individual's expected level of development (e.g., based on age). A determination of the individual's actual level of development (e.g., evaluated using speech and/or language metrics) can be compared to the expected level of development to determine whether the individual has one or more behavioral disorders, developmental delays, and neurologic impairments, for example, speech and/or language delay, In some embodiments, verbal communication comprises recognizable words and phrases, near recognizable words and phrases, gibberish, babbling, laughing, grunting, crying, or any audible communication that conveys emotion, thought, intent, or request. In some embodiments, behavioral units corresponding to speech are analyzed to determine metrics of speech and/or language development. For example, these metrics can include speech metrics such as articulation of speech sounds, fluency, and voice, and language metrics such as receptive skills (e.g., ability to understand and decode language) and expressive skills (e.g., ability to produce and use language). As an illustrative example, audio may be parsed to identify specific speech sounds (e.g., individual phonemes or a collection of phonemes that make up a word) that make up a verbal input or feedback from a subject, and the parsed speech sounds may be compared against a baseline or reference standard speech sound to determine a score. As another illustrative example, a collection of words may be evaluated for acoustic features such as the presence of pauses.

In some embodiments, non-verbal communication comprises pointing to direct another's attention, touching a person or object, waving, clapping, taking another by the hand or body and leading, making noise with an object, indicating emotion or thoughts with facial expression or body movement., or eye contract. In some embodiments, non-verbal communication comprises facial expression, posture, gesture, eye contact, or touch.

In some embodiments, displays of thought or emotion occur through the use of body language and facial expression. In some embodiments, the emotion comprises anger, anticipation, anxiety, apathy, annoyance, boredom, unhappiness, calm, carefree, cheerfulness, nervousness, comfort, compassion, concentration, confidence, contentment, curiosity, delight, desire , despair, disappointment, determination, disgruntlement, disgust, dismay, dread, embarrassment, envy, excitement, fear, frustration, glee, gratitude, grief, guilt, happiness, hatred, hopefulness, impatience, irritation, jealousy, joy, loneliness, love, overwhelmed, panic, pain, paranoia, pride, rage, regret, relief, reluctance, remorse, resentment, sadness, satisfaction, self-pity, shame, shock, smugness, suspicion, wonder, or worry.

In some embodiments, a higher order behavior comprises control over movement. In some embodiments, control over movement is determined by analyzing the individual's movement and providing a likelihood that the individuals movements are abnormal within the context of the video. In some embodiments, control of movement is determined by the absence or presence of behavior units associated with movement control. In some embodiments, behavior units associated with movement control comprise twitching movements; stumbling movements, tripping movements, striking objects or people with extremities or body, dropping of objects, losing balance, a surprised facial expression, a frustrated facial expression, an angry facial expression, a concentrated facial expression, a pained facial expression, embarrassed facial expression, crying, yelling, or a verbal communication associated with a lack of control over movement. In some embodiments, the individuals age, disability, or injury is taken into account in determining the presence or absence of control over movement. In some embodiments, an individual's control over movement is determined as a percentage, for example, an individual may be in control of about 100%, 99%, 95%, 80%, 75%, 50%, or 25% of the individual's movements.

In some embodiments, direction of gaze or attention comprises evaluating the directionality of the subject's gaze and length of the gaze. In some embodiments, the directionality and length of gaze is associated with other movements, objects the individual is interacting with, or persons the individual is interacting with. For example, a video is evaluated wherein an adult is asking an individual questions and the individual is responding. The direction of the individual's gaze is evaluated to in order to determine whether the individual is making eye contact with the questioner or caretaker, and for how long. If additional stimuli are introduced, such as a second person or animal entering the proximity of the individual and the individual turns his or her gaze to the additional stimuli, the analysis accounts for such. In some embodiments, the individual's ability to maintain eye contact with the questioner or caretaker is a higher order behavior.

In some embodiments, direction of verbal communication comprises evaluating the directionality of the subject's verbal communication. In some embodiments, the directionality and context of the communication is associated with other movements, objects the individual is interacting with, or persons the individual is interacting with. For example, the volume of an individual's verbal communication may fluctuate in volume due to the individual directing their voice in multiple directions. If the intended recipient of the communication is static, the individual may not face the questioner or caretaker while responding. The individual may be walking around or turning away while responding to a question. In some embodiments, sustaining a particular direction while verbally communicating is a higher order behavior.

In some embodiments, machine learning algorithms are used to identify higher order behaviors.

Behavioral Patterns

One or more higher order behaviors and/or behavioral units observed over time may together make up one or more behavioral patterns. Behavioral patterns that are identified by the methods, devices, systems, software, and platforms described herein, in some embodiments, are an output that is provided and serves as at least a portion of an evaluation that is generated for an individual being evaluated. In some embodiments, identifying behavioral patterns from collections of higher order behaviors and/or behavioral units provides a way to organize, contextualize, and/or better evaluate individual higher order behaviors and behavioral units.

In some embodiments, a behavioral pattern comprises behavioral units or higher order behaviors mapped over time. In some embodiments, a behavioral pattern comprises two or more higher order behaviors that are associated with each other. For example, in response to a question, an individual gives a verbal response while shifting gaze continuously and walking around a room. The individual's response initially addresses the question but the response slowly trails off, diminishing in volume. The higher order behaviors are identified as avoiding eye contact when responding, avoiding facing the questioner or caretaker when responding and failing to answer the question. The behavioral pattern identified may indicate that the individual is unable to sufficiently focus on verbal communication long enough to answer a question. The behavioral pattern or higher order behaviors might be associated with both ADHD and a form of autism. However, due to differences in an individual's specific behavioral units, the machine learning algorithms described herein separate each condition and provide a probability score for each diagnosis.

In some embodiments, a behavior pattern comprises the ability to respond to a stimulus, the ability to carry out an assigned task, appropriate speech responses, appropriate movement, ability to focus, or the ability to perceive the world accurately.

In some embodiments, machine learning algorithms are used to recognize behavioral patterns.

Figure 2:
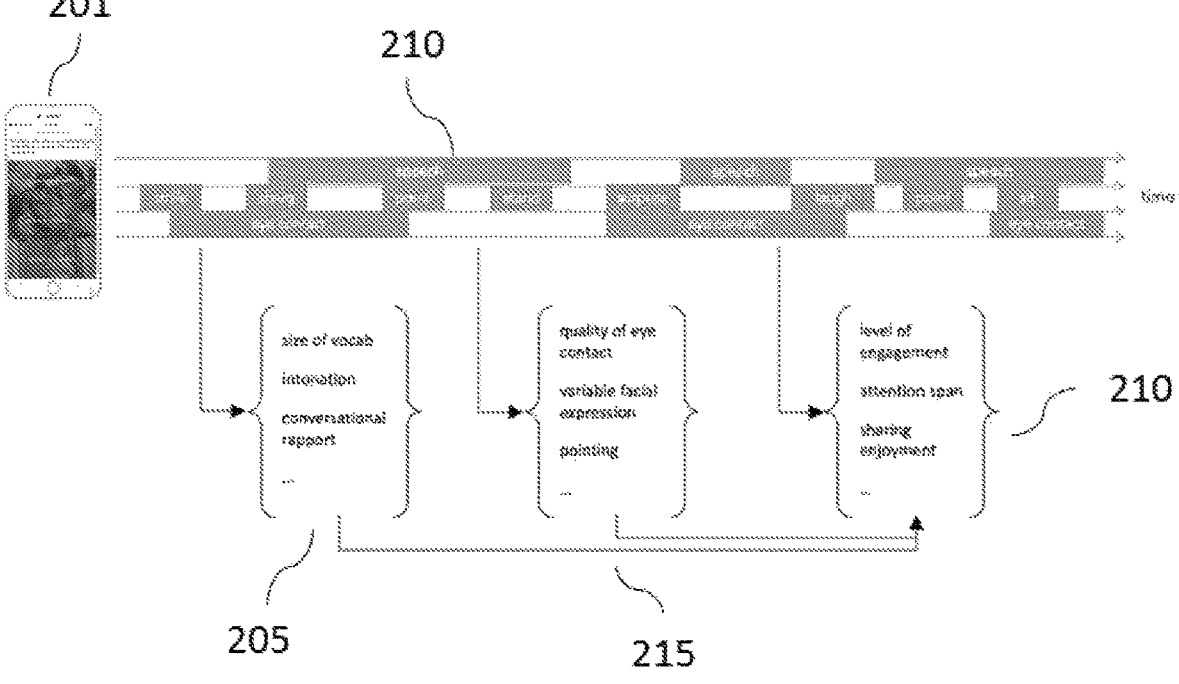
FIG. 2 shows a representation of how behavioral units and higher order behaviors are mapped over time to produce behavioral patterns.

FIG. 2 shows a representation of how behavioral units 205 and higher order behaviors 210 are mapped over time 215 to produce behavioral patterns 220. A mobile video and audio capturing device 201 records a video of the individual. The trained machine learning algorithm recognizes each behavior unit and maps the presence of each over time 215, exemplified as speech, a smile, a point, a shrug, standing, laughing, sitting, and eye contact. Higher order behaviors are constructed from the behavior units 210, exemplified as size of vocabulary, intonation of voice, conversational rapport, quality of eye contact, facial expression, and pointing toward an object. The machine learning algorithm utilizes the behavioral units and higher order behaviors mapped over time to produce behavioral patterns 220, exemplified as level of engagement, attention span, and enjoyment from sharing.

Methods for Evaluating Behavioral Disorders, Developmental Delays, and Neurologic Impairments In some embodiments, an individual is evaluated by recording video and/or audio data of the individual, wherein evaluating said video and/or audio data is performed with the machine learning algorithms described herein. In some embodiments, the individual is recorded answering questions asked by a human questioner or caretaker. In some embodiments, the individual remains seated while giving responses to the questioner or caretaker. In some embodiments, the individual is permitted to sit or move freely about a room while giving responses to the questioner or caretaker. In some embodiments, the individual remains in the frame of the recording device. In some embodiments, the individual remains within audible distance of the recording device. In some embodiments, the audible distance is within 25, 10, 5, or 3 meters or less of the recording device. In some embodiments, the individual is evaluated by responding to questions with verbal communication. In some embodiments, the individual is evaluated by responding to questions with non-verbal communication. For example a questioner may ask an individual to make facial expressions such as smiling or ask the individual to act out an emotion such as being excited. Responses to such questions may evaluate whether the individual can perceive other's behavior and appropriately replicate said behavior. In some embodiments, the questioner interacts with the individual to elicit a desired response. For example, the questioner may reward the individual with a favorite food or compliment the individual. The questioner may also ask questions to make the individual uncomfortable or emotional. In some embodiments, there is no questioner, and the individual is recorded without prompting or stimulation from a third party. In some embodiments, the recording is taken with guidance to the recorder. For example, the guidance may be given to the recorder to record the individual sleeping, playing, eating, communicating, or evoking a specific emotion.

In some embodiments, the video and/or audio recording is taken with a mobile device. In some embodiments, the mobile device is a smartphone, a tablet, a smartwatch, or any device with a mobile camera or recording feature. In some embodiments, the video and/or audio recording is taken with a stationary camera and/or microphone. For example, an individual may be asked questions in a clinician's office and have their responses recorded with a camera on a tripod with a mounted microphone. In some embodiments, the camera is a high-definition camera.

In some embodiments, the methods disclosed herein are used to aid in the diagnosis behavioral disorders, developmental delays, or neurological impairments.

In some embodiments, the methods disclosed herein are used to aid in the diagnosis of behavioral disorders. In some embodiments, behavioral disorders comprise Attention Deficit Hyperactivity Disorder (ADHD), Oppositional Defiant Disorder (ODD), Autism Spectrum Disorder (ASD), Anxiety Disorders, Depression, Bipolar Disorders, Learning Disorders or Disabilities, or Conduct Disorder. In some embodiments, an Attention Deficit Hyperactivity Disorder comprises Predominantly Inattentive ADHD, Predominantly Hyperactive-impulsive type ADHD, or Combined Hyperactive-impulsive and Inattentive type ADHD. In some embodiments, Autism Spectrum Disorder comprises Autistic Disorder (classic autism), Asperger Syndrome, Pervasive Developmental Disorder (atypical autism), or Childhood disintegrative disorder. In some embodiments, Anxiety Disorders comprise Panic Disorder, Phobia, Social Anxiety Disorder, Obsessive-Compulsive Disorder, Separation Anxiety Disorder, Illness Anxiety Disorder (Hypochondria), or Post-Traumatic Stress Disorder. In some embodiments, Depression comprises Major Depression, Persistent Depressive Disorder, Bipolar Disorder, Seasonal Affective Disorder, Psychotic Depression, Peripartum (Postpartum) Depression, Premenstrual Dysphoric Disorder, 'Situational' Depression, or Atypical Depression. In some embodiments, Bipolar Disorders comprise Bipolar I Disorder, Bipolar II Disorder, Cyclothymic Disorder or Bipolar Disorder due to another medical or substance abuse disorder. In some embodiments, learning disorders comprise Dyslexia, Dyscalculia, Dysgraphia, Dyspraxia (Sensory Integration Disorder), Dysphasia/Aphasia, Auditory Processing Disorder, or Visual Processing Disorder. In some embodiments, behavioral disorder is a disorder defined in any edition of the Diagnostic and Statistical Manual of Mental Disorders (DSM).

In some embodiments, the methods disclosed herein are used to aid in the diagnosis of developmental delays. In some embodiments, developmental delays comprise Autism Spectrum Disorder, Mental Retardation, Cerebral Palsy, Down Syndrome, Failure to Thrive, Muscular Dystrophy, Hydrocephalus, Developmental Coordination Disorder, Cystic Fibrosis, Fetal Alcohol Syndrome, Homocystinuria, Tuberous Sclerosis, Abetalipoproteinemia, Phenylketonuria, Aase Syndrome, speech delays, gross motor delays, fine motor delays, social delays, emotional delays, behavioral delays, or cognitive delays. In some embodiments, Mental Retardation comprises Adrenoleukodystrophy, Ito Syndrome, Acrodysostosis, Huntington's Disease, Aarskog Syndrome, Aicardi Syndrome or Tay-Sachs Disease. In some embodiments, Cerebral Palsy comprises Spastic Cerebral Palsy, Dyskinetic Cerebral Palsy, Hypotonic Cerebral Palsy, Ataxic Cerebral Palsy, or Mixed Cerebral Palsy. In some embodiments, Autism Spectrum Disorder comprises Autistic Disorder (classic autism), Asperger Syndrome, Pervasive Developmental Disorder (atypical autism), or Childhood disintegrative disorder. In some embodiments, Down Syndrome comprises Trisomy 21, Mosaicism, or Translocation. In some embodiments, Muscular Dystrophy comprises Duchenne muscular dystrophy, Becker muscular dystrophy, Congenital muscular dystrophy, Myotonic dystrophy, Facioscapulohumeral muscular dystrophy, Oculopharyngeal muscular dystrophy, Distal muscular dystrophy, or Emery-Dreifuss muscular dystrophy.

In some embodiments, the methods disclosed herein are used to aid in the diagnosis of neurological impairments. In some embodiments, neurological impairments comprise Amyotrophic Lateral Sclerosis, Arteriovenous Malformation, brain aneurysm, brain tumors, Dural Arteriovenous Fistulae, Epilepsy, headache, memory disorders, Multiple Sclerosis, Parkinson's Disease, Peripheral Neuropathy, Post-Herpetic Neuralgia, spinal cord tumor, stroke, Alzheimer's Disease, Corticobasal Degeneration, Creutzfeldt-Jakob Disease, Frontotemporal Dementia, Lewy Body Dementia, Mild Cognitive Impairment, Progressive Supranuclear Palsy, or Vascular Dementia.

In some embodiments, the methods disclosed herein are used to aid in the diagnosis behavioral disorders, developmental delays, or neurological impairments. In some embodiments, the methods described herein are used in conjunction with known techniques of diagnosing behavioral disorders, developmental delays, or neurological impairments. In some embodiments, the methods described herein are used in conjunction with the administration of questionnaires or video observation by a clinician. In some embodiments, the methods described herein enhance the accuracy of known methods of diagnosis, or reduce the time or recourses required for accurate diagnosis.

In some embodiments, the methods disclosed herein are used to monitor the progression or regression of behavioral disorders, developmental delays, and neurologic impairments. In some embodiments, the individual has been diagnosed with a behavioral disorder, developmental delay, or neurologic impairment and is undergoing treatment. In some embodiments, the methods disclosed herein are used to evaluate the efficacy of the treatment. In some embodiments, monitoring or evaluating the individuals condition involves the analysis of the number and/or frequency of relevant behavioral units, higher order behaviors, and behavioral patterns detected over the course of multiple analysis sessions. In some embodiments, the machine learning modules disclosed herein are used to analyze the recording of each analysis session and provide a progress value. In some embodiments, the progress value is derived from comparing the probability score (vide infra) of each analysis session over time. For example, a child undergoing treatment for autism may be evaluated for autism over the course of 3 analysis sessions. Each evaluation by the machine learning module produces a probability score used to indicate the likelihood that the individual is autistic. The probability scores decrease over the three sessions. These results would suggest that the prescribed treatment is effective, and the initial diagnosis correct. The machine learning algorithm provides a suggestion that the treatment is continued. In some embodiments, the progress value is obtained from a machine learning module trained on progression data. In some embodiments, progression data are recordings of analysis sessions of individual patients whose behavioral disorders, developmental delays, and neurologic impairments have regressed or progressed, as determined by a clinician. The clinician determination is included in the progression data. For example, the machine learning module is trained on series of recordings in which individuals have been treated for ADHD, the training data including a clinical determination on whether the condition is progressing or regressing. The machine learning module analyses a series of recordings of an individual diagnosed with ADHD to determine whether a given treatment regimen is efficacious. The machine learning algorithm determines that the condition is progressing. The machine learning algorithm provides a recommendation that the individuals treatment is changed, and/or the ADHD diagnosis is re-evaluated.

In some embodiments, behavioral patterns are monitored over time. For example, an individual with ADHD might be evaluated for energy level, sociability, and vocabulary over the course of multiple years.

Figure 5A:
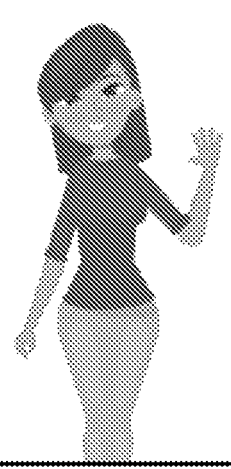
FIG. 5A shows a non-limiting illustration of a graphical display with a virtual character providing guidance to a user during an activity.
Figure 5B:
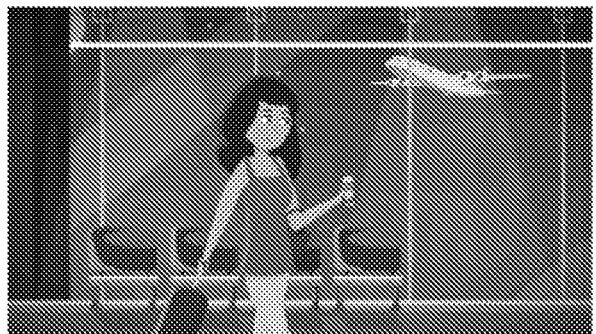
FIG. 5B shows a non-limiting illustration of a graphical display with a story sequence provided during an activity.
Figure 5C:
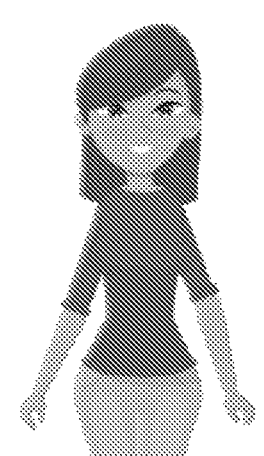
FIG. 5C shows a non-limiting illustration of a graphical display with a question provided by a virtual character during an activity.

Interactive Modules for Evaluating and Treating Behavioral Disorders, Developmental Delays, and Neurologic Impairments In some embodiments, the systems and methods disclosed herein comprise one or more interactive modules for evaluating and/or treating behavioral disorders, developmental delays, and neurologic impairments. An interactive module can provide one or more activities to an individual for assessing or evaluating and/or treating behavioral disorders, developmental delays, or neurologic impairments, or a symptom or cognitive function associated with said disorders, delays, or impairments. The activities can be interactive activities in which the individual is presented with stimulus and a corresponding prompt, for example, a portion of a story along with question relating to that portion of the story. For example, FIG. 5A shows an example of a GUI display with a virtual character providing guidance for a story. The story sequence then begins (see FIG. 5B). Once the story sequence is complete (FIG. 6B shows an example of a story sequence), the virtual character may prompt the individual or user to answer a question (see FIG. 5C) or provide instructions (see FIG. 6A). The feedback or response by the individual prompted by the activity can be detected and stored, for example, audio and/or video data detected by the microphone and/or camera of the computing device. The detection of audio and/or video information of the individual, processing of this information to identify behavioral units, and analysis of the behavioral units to determine higher level behavior and/or behavioral pattern can be implemented as described throughout this specification. Another illustrative example of interactive activities is an emotion guessing game in which a user is prompted to guess the emotion of one or more characters in an image by providing a verbal response that can be recorded as audio information. Another illustrative example of interactive activities is an exploration game in which a user is prompted to point a camera at different objects and describe them. Accordingly, the present platforms, devices, and methods can incorporate a variety of interactive activities.

In some embodiments, the interactive module is configured to dynamically prompt the user to adjust the context until it is appropriate for assessment. For example, the interactive module automatically asks the user to move their face until it is visible to the camera, ask the user to speak louder if not audible, or to turn on the lights if the video/camera image is too dark.

Figure 7A:
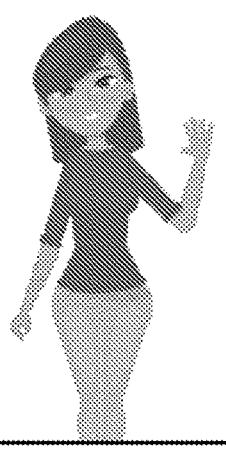
FIG. 7A shows a non-limiting illustration of a graphical display with a virtual character prompting a user to review a visual story sequence and come up with a narrative corresponding to the story sequence.
Figure 7B:
FIG. 7B shows a non-limiting illustration of the visual story sequence of FIG. 7A that consists of a picture.

Various activities can be used to provide digital therapy and/or assessment/evaluation of the individual in addition to the examples disclosed herein. For example, non-limiting examples of activities include displaying a picture and prompting the individual to come up with a narrative or story describing the picture (see FIG. 7A-7B). Another example is an activity providing a sequence of pictures or images and prompting the individual to arrange them in order or the appropriate sequence (see FIG. 8). Yet another example is an activity that provides GUI tools allowing an individual to create their own story using graphic and/or audio elements (see FIG. 9). Yet another example is an activity that provides embedding intervention through social stories (see FIG. 10) or game-based life skill training (see FIG. 11).

A significant advantage of an interactive module disclosed herein is that it can facilitate a dynamic process by which an individual is both treated and re-evaluated or assessed over the course of the activity. This enables the interactive module to be adjusted or modified in real-time in response to input, feedback, or other collected user information. The interactive module can be configured to modify the difficulty of one or more activities based on ongoing assessment of the user, for example, increasing difficulty as the child becomes more proficient according to speech and/or language proficiency metrics (e.g., measures of articulation of speech sounds, fluency, etc.) or decreasing difficulty if the child's proficiency is falling below a minimum threshold. For example, if the current difficulty of the activity is determined to be too high (e.g., child is having trouble answering questions or articulating verbal responses, resulting in above 50% error rate in articulation of speech sounds), then the difficulty may be adjusted downward during the same session while the individual is still engaged in the activity. Alternatively or in combination, the activity is modified or adjusted after the session is over so that any changes such as difficulty are incorporated for the next session. This process can occur repeatedly (e.g., periodically or continuously) between activities or during the same activity. In some embodiments, the interactive module modifies or adjusts the activity over time based on evaluation of the user information collected during the activity (or, in some cases, information collected from follow-up tests or assessments after the activity ends). The modification of the activity can be based on progress of the individual. For example, the individual may be successfully meeting target metrics for speech and/or language proficiency (e.g., threshold percentage of success in verbalizing sounds, etc.), which may cause the activity or a next activity to be adjusted to increase the difficulty or challenge for the individual user.

The speech assessment carried out using the interactive module can include various conditions. Non-limiting examples of conditions that can be evaluated with respect to speech assessment include apraxia dysarthria, and articulation for sound. Non-limiting examples of conditions that can be evaluated with respect to speech assessment include phonological and phonemic for phonetic. Non-limiting examples of conditions that can be evaluated with respect to speech assessment include stuttering, prolongations, repetitions, blocks, and cluttering for fluency. Non-limiting examples of conditions that can be evaluated with respect to speech assessment include structural, neurogenic, and functional for voice.

In some embodiments, the interactive module is configured to evaluate and/or treat the behavioral disorders, developmental delays, or neurologic impairments. For example, autism spectrum disorder has core characteristics such as communication and social pragmatic deficits. These characteristics can include less frequent narration in conversations, reduced cohesiveness, difficulty referencing mental states in narratives, and difficulty using causal language. Attention deficient hyperactivity disorder is frequently characterized by language impairments including, for example, shorter utterances, less organized and coherent speech, more sequence errors, and misinterpretations and word substitutions. Accordingly, the interactive module provides activities that act as digital therapies that can help individuals improve upon these characteristics.

The systems and methods disclosed herein offer an improvement over traditional assessments that include SSR, which includes a parent interview, observation of reading sessions, and a video recording of the individual, and clinical evaluation which includes a parent interview, standardized testing (Wh-question, vocabulary, picture books), and informal probes. These traditional assessments are time consuming and expensive. By contrast, disclosed herein are systems and methods that provide automated activities such as an automated storytelling activity or mode in which the individual is guided through a story while evaluating feedback or other data for the individual to assess various speech and/or language metrics, including, for example, story comprehension, story recall or story retell, and picture-elicited narrative. In some cases, a parent questionnaire may be provided to obtain additional relevant input data.

In some embodiments, the interactive module both provides the activity and receives or obtains user input or response to the activity. For example, the user input or response can include answers to questions or prompts, selection of available options or changes to the activity, audio/visual information obtained through microphone/ camera recordings of the individual during the activity, and other forms of information that can be gathered during the duration of the activity. The input or response can be actively collected, for example, the user is prompted to provide the input or response by the module, which may include written or typed responses via the graphic user interface of the user device or alternatively via spoken audio (optionally including video) detected by the microphone and/or camera of the user device. Alternatively, the input or response can be passively collected, for example, audio and video information collected without requiring active instructions or prompting of the individual. Examples of collected data include microphone and/or camera automatically collect audio and/or video data relating to spoken words, facial expressions, or other data that can be used to determine behavioral units and/or patterns. In some embodiments, the activity is dynamic depending on the user engagement or input/feedback. As an example, the activity is a storytelling mode that guides the individual or user through a story while actively asking questions and receiving user input. The activity may include active participation by the individual, for example, allowing the individual to assume the role or perspective of a character in the story in which verbal or audio words or sounds made by the individual are recorded.

In some embodiments, a software module is configured to evaluate the user input, response, feedback, or other collected user data during the course of the activity. In some embodiments, the data is analyzed to determine or assess the behavioral disorder, developmental delay, or cognitive impairment, or some associated sign, symptom, or cognitive function. In some cases, the behavioral unit and/or higher level behavior or behavioral pattern is identified or evaluated. The behavioral unit can include spoken sounds, words, or phrases that are identified as speech (or attempts at speech). In some cases, the behavioral unit comprises the elements of speech such as speech sounds or phonemes, which are analyzed to identify the words or phrases that make up speech.

In some embodiments, the systems and methods disclosed herein comprise an interactive module configured to collect data (e.g., audio of the user's speech) and a diagnostic or evaluation module configured to analyze the data to detect a speech or language delay or disorder, or a sign or symptom thereof. In some embodiments, the evaluation module is configured to determine a severity level of one or more developmental delays or a symptom or cognitive function associated with the one or more developmental delays (e.g., speech or language delay). Non-limiting examples include the level of speech and/or language, emotion recognition, nonverbal communication (e.g., degree of vocal development deficit), reading comprehension, word acquisition, and other signs, symptoms, or cognitive functions. The severity level can be a score, a category (e.g., low, moderate, or high severity of the impairment or deficit), or other suitable metric for evaluating these signs, symptoms, or cognitive functions. In some embodiments, a speech disorder or delay comprises specific symptoms or cognitive metrics. For example, a speech disorder may encompass articulation of speech sounds (e.g., how well a child can articulate the specific speech sounds), fluency (e.g., stuttering indicates a lack of fluency), and voice. Articulation errors include substitution errors in which a sound or phoneme the child is able to make is substituted for a sound or phoneme the child cannot yet make, omission errors in which a sound is left out that is too hard to make (e.g., the "r" consonant is left out of "red"), distortion errors in which the sound or phoneme is used but not articulated correctly, and addition errors in which extra sound(s) or phoneme(s) is added.

In some embodiments, the systems and methods disclosed herein provide an interactive module comprising an interactive activity. The interactive activity can be personalized or customized based on a target demographic (e.g., age of the individual). For example, the activity may have a difficulty level that is adjusted depending on the individual's age (e.g., difficulty or complexity of the activity can be categorized into various ages such as 3, 4, 5, 6, 7, or 8 years of age). In some embodiments, input or responses of the individual are obtained, for example, audio clips (audio data) collected of the individual.

In some embodiments, the interactive module provides the results of an assessment to the individual or user. The results of the assessment can include evaluations or performance metrics or scores thereof that correspond to fine motor, cognitive, gross motor, speech & language, social & emotional, and behavioral categories (see FIG. 11A). The categories can be selectable within the graphic user interface of the interactive module to reveal additional subcategories or metrics such as, for example, speech, fluency, voice, and language for the speech & language category (see FIG. 11B). An explanation of the individual's evaluation results can be provided (see FIG. 11C).

Speech and Language Analysis

In some embodiments of the methods, devices, systems, software, and platforms described herein, a software module is utilized to analyze audio information for an individual to identify behavioral units, and/or higher order behaviors, and/or behavioral patterns relating to speech and/or language. In some embodiments, the software module utilizes one or more machine learning algorithms or models to engage in automated speech recognition and speech/language analysis using audio data obtained for the individual.

In some embodiments, the audio data is obtained using interactive activities such as those provided by an interactive module as described herein. The interactive module can be provided through a computer device such as a smartphone or tablet computer. The interactive activities can include stories and picture description tasks that elicit speech and language production from children while requiring minimal assistance from parents. The speech and language data can then be analyzed by the software module for feature extraction and automatic diagnostic evaluation, for example, of speech and/or language proficiency. The audio data can be processed to identify elements of speech. For example, an audio clip can be processed to identify phonemes that represent distinct units of sound in a particular language (e.g., English).

In some embodiments, video or camera data is also obtained and used alone or in combination with audio data for feature extraction and automatic diagnostic evaluation. The video or camera data can be used to detect facial features or other features through a built-in camera of a smartphone or tablet.

In some embodiments, the audio data is processed to identify sounds correspond to speech. In some embodiments, audio data is processed or analyzed to identify spoken sounds, words, or phrases. The spoken sounds, words, or phrases can be analyzed to determine one or more performance metrics or parameters relating to speech and/or language. In some embodiments, the software module identifies acoustic features that are relevant to speech and/or language. For example, acoustic features can include features relating to speech pause such as the number of short and/or long pauses, the average length of the pauses, the variability of their length, and other similar statistics on uninterrupted utterances. In some embodiments, the software module engages in automated speech, prosody, and morphosyntax analysis. For example, the analyses can include automated measurement of dialogue structure, discriminative syntactic analysis based on speech recognition, and automatic measurement of affective valence and emotional arousal in speech. In some embodiments, the software module determines semantic similarity measures, for example, word overlap measures that correspond to a simple word overlap measure between a pair of narratives defined as the size of intersection of the words in narratives. Such measures can be useful, for example, in determining how much of an individual's retelling of a story during an interactive activity corresponds to the original story, thus providing a metric for proficiency in story retelling.

The speech and/or language data can be analyzed using the algorithms or models disclosed herein to determine an individual's proficiency in speech and language. Speech proficiency can be measured in terms of articulation (e.g., production of age-appropriate speech sounds), fluency (e.g., production of speech with age-appropriate continuity, which can be measured using number and duration of unnecessary pauses), and voice (e.g., production of normal voice quality). Language proficiency can be measured in terms of receptive and expressive language (e.g., whether the child understands spoken language and produces speech to communicate), and narrative skills (e.g., whether the child can understand, retell, and create a cohesive story using language).

Machine Learning Software Modules

In some embodiments of the methods, devices, systems, software, and platforms described herein, a machine learning software module is utilized to identify one or more behavioral units, and/or higher order behaviors, and/or behavioral patterns, and/or an indication of a likelihood of whether a particular condition is present in an individual being evaluated. A machine learning software module in some embodiments comprises a machine learning model (or data model). It should be understood that machine learning encompasses numerous architectures and arrangements of data and that the teachings herein are not limited to any one single type of machine learning.

A machine learning software module described herein is generally trained using a video and/or audio dataset. In some embodiments, a video and/or audio dataset comprises previously identified behavioral units. In some embodiments, the video and/or audio dataset comprises previously identified behavioral units and a diagnosis of behavioral disorder, developmental delay, or neurological impairment. In some embodiments, a video and/or audio dataset comprises previously identified higher order behaviors. In some embodiments, a video and/or audio dataset comprises previously identified higher order behaviors and a diagnosis of behavioral disorder, developmental delay, or neurological impairment. In some embodiments, a video and/or audio dataset comprises previously identified behavioral patterns and a diagnosis of behavioral disorder, developmental delay, or neurological impairment. In some embodiments, a video and/or audio dataset comprises previously identified behavioral units and previously identified higher order behaviors. In some embodiments, a video and/or audio dataset comprises previously identified behavioral units, previously identified higher order behaviors, and a diagnosis of behavioral disorder, developmental delay, or neurological impairment. In some embodiments, a video and/or audio dataset comprises previously identified higher order behaviors and previously identified behavioral patterns. In some embodiments, a video and/or audio dataset comprises previously identified higher order behaviors, previously identified behavioral patterns, and a diagnosis of behavioral disorder, developmental delay, or neurological impairment. In some embodiments, a video and/or audio dataset comprises previously identified behavioral units and previously identified behavioral patterns. In some embodiments, a video and/or audio dataset comprises previously identified behavioral units, previously identified behavioral patterns, and a diagnosis of behavioral disorder, developmental delay, or neurological impairment. In some embodiments, a video and/or audio dataset comprises previously identified behavioral units, previously identified higher order behaviors and previously identified behavioral patterns. In some embodiments, a video and/or audio dataset comprises previously identified behavioral units, previously identified higher order behaviors, previously identified behavioral patterns, and a diagnosis of behavioral disorder, developmental delay, or neurological impairment.

In some embodiments, a trained machine learning software module analyzes new video and/or audio data that has not been previously associated with behavioral units, higher order behaviors, behavioral patterns, or a particular behavioral disorder, developmental delay, or neurological impairment. In some embodiments, the machine learning software module identifies one or more behavioral units, higher order behaviors, or behavioral patterns present in the new video and/or audio data. In some embodiments, the machine learning software module identifies one or more behavioral units present in the new video and/or audio data. In some embodiments, the machine learning software module identifies one or higher order behaviors present in the new video and/or audio data. In some embodiments, the machine learning software module identifies one or more behavioral patterns present in the new video and/or audio data. In some embodiments, the machine learning algorithm analyzes new video and/or audio data and provides a probability that one or more behavioral disorders, developmental delays, or neurological impairments is present in an individual being evaluated.

In some embodiments, one or more machine learning software modules are utilized to identify behavioral units, identify higher order behaviors, identify behavioral patterns, and provide a diagnosis of a behavioral disorders, developmental delays, or neurological impairments. In some embodiments, a machine learning software module for the identification of behavioral units is a feature detection algorithm. In some embodiments, a machine learning software module for the identification of higher order behaviors is a higher order behavior detection algorithm. In some embodiments, a machine learning software module for the identification behavioral patterns is a behavioral pattern detection algorithm. In some embodiments, a machine learning software module for the diagnosis of behavioral disorders, developmental delays, or neurological impairments is a behavioral assessment algorithm.

In some embodiments, the machine learning software module is a supervised learning algorithm. In some embodiments, the machine learning software module is selected from nearest neighbor, naive Bayes, decision tree, linear regression, support vector machine, or neural network.

In some embodiments, the machine learning software module provides a probability diagnosis without taking into account contextual indicators. In some embodiments, the machine learning software module provides a probability diagnosis through the analysis of the video or audio data solely. In some embodiments, the machine learning software module provides a probability diagnosis through the analysis of the video or audio data and contextual indicators. For example, a user provides video data and audio data of a 5 year old male child responding to questions designed to evaluate the child for autism. In one embodiment, the machine learning software module analyzes the video and audio data and includes data input by the user related to contextual indicators such as the child's age, sex, suspected diagnosis, surroundings and expectation of verbal responses to questions. In another embodiment, the machine learning software module analyzes the video and audio data without the contextual indicators exemplified above.

In some embodiments, the methods disclosed herein utilize a probability score for recommending a diagnosis. For example, the machine learning software modules may analyze a data set and determine that a number of indications are present and assign varying scores that reflect the degree of overlap in the behavior units, higher order behavior, or behavioral patterns identified in the data set to those identified in the data sets used to train the machine learning software module for each indication. In some embodiments, the probability score is a reflection of how the data fit each modeled indication. In some embodiments, one or more behavioral disorders, developmental delays, or neurological impairments are given probability scores. In some embodiments, the probability score is termed a "prediction."

In some embodiments, a probability score threshold can be used in conjunction with a probability score to determine whether or not a diagnosis is recommended. For example, if a probability score is too low, a diagnosis for the indication is not recommended.

In some embodiments, the probability threshold is used to tune the sensitivity of the trained machine learning software module. For example, the probability threshold can be 1%, 2%, 5%, 10%, 15%, 20%, 25%, 30%, 35%, 40%, 45%, 50%, 55%, 60%, 65%, 70%, 75%, 80%, 85%, 90%, 95%, 98% or 99%. In some embodiments, the probability threshold is adjusted if the accuracy, sensitivity or specificity falls below a predefined adjustment threshold. In some embodiments, the adjustment threshold is used to determine the parameters of the training period. For example, if the accuracy of the probability threshold falls below the adjustment threshold, the system can extend the training period and/or require additional recordings and/or identity data. In some embodiments, the additional recordings and/or identity data can be included into the training data. In some embodiments, the additional recordings and/or identity data can be used to refine the training data set.

Figure 3:
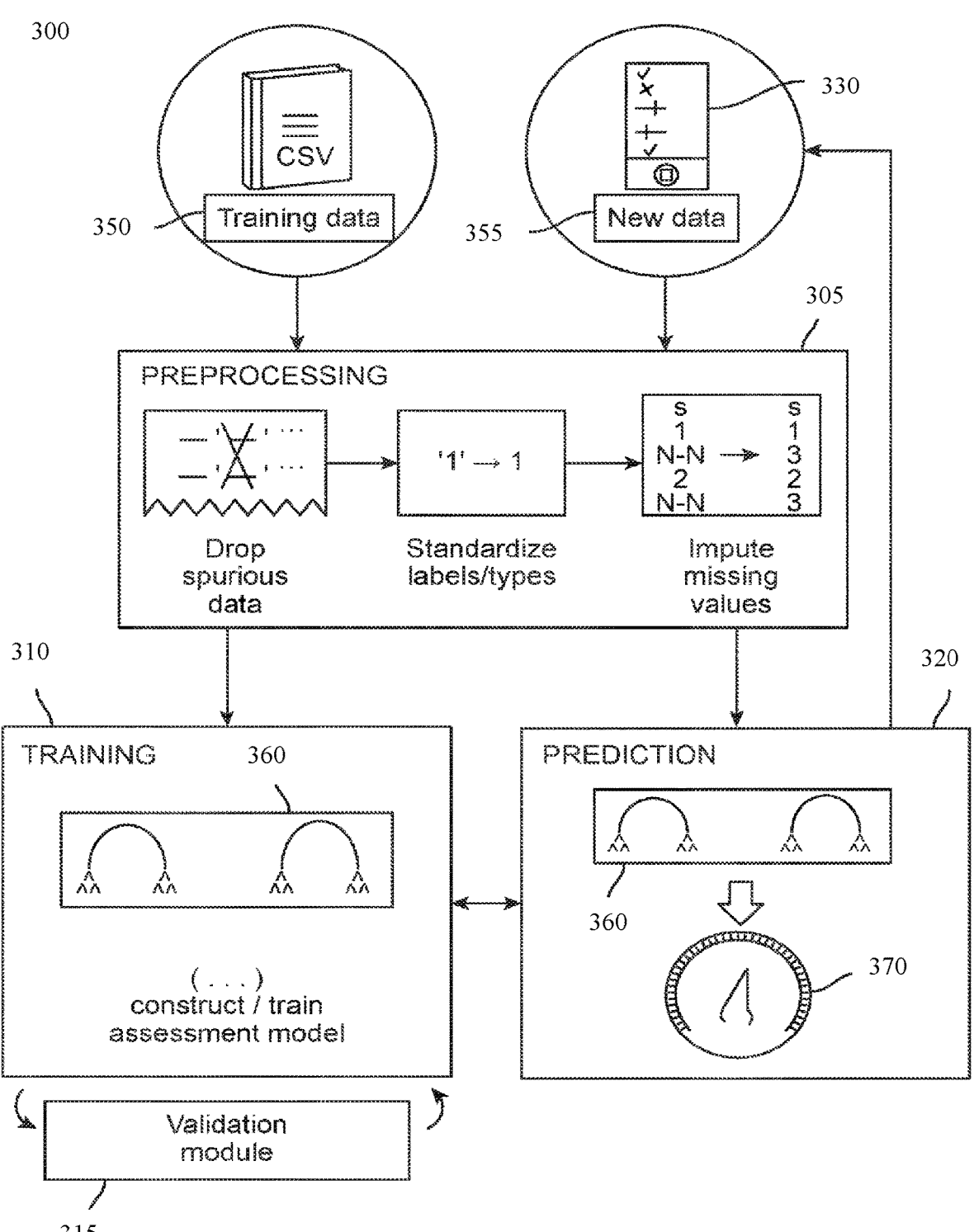
FIG. 3 is a schematic diagram of an exemplary data processing module for providing the machine learning algorithms and methods described herein.

FIG. 3 is a schematic diagram of an exemplary data processing module 300 for providing the machine learning algorithms and methods described herein. The data processing module 300 generally comprises a preprocessing module 305, a training module 310, and a prediction module 320. The data processing module can extract training data 350 from a database, or intake new data 355 with a user interface 330. The preprocessing module can apply one or more transformations to standardize the training data or new data for the training module or the prediction module. The preprocessed training data can be passed to the training module, which can construct a trained machine learning algorithm 360 based on the training data. The training module may further comprise a validation module 315, configured to validate the trained machine learning algorithm using any appropriate validation algorithm (e.g., Stratified K-fold cross-validation). The preprocessed new data can be passed on to the prediction module, which may output a prediction 370 of whether a particular condition is likely to be present in the individual (e.g. a behavioral disorder, developmental delay, or neurologic impairment) by fitting the new data to the machine learning algorithm constructed with the training module.

The training data 350, used by the training module to construct the machine learning model, can comprise a plurality of datasets from a plurality of subjects, each subject's dataset comprising an array behavioral units, higher order behaviors, or behavior patterns and a classification of the subject's behavioral disorders, developmental delays, or neurological impairments. Behavioral units may comprise movement or sound of a subject that is machine detectable and clinically relevant to the likely presence or absence of a behavioral disorder, developmental delay, or neurologic impairment. Each behavioral unit, higher order behavior, or behavior pattern may be relevant to the identification of one or more developmental disorders or conditions, and each corresponding behavioral unit, higher order behavior, or behavior pattern may indicate the degree of presence of the disorder in the specific subject. For example, behavior pattern may be the ability of the subject to engage in imaginative or pretend play, and the value for a particular subject may be a score corresponding to the degree of presence of the behavioral pattern in the subject. The behavioral pattern may be observed in the subject, for example with a video of the subject engaging in a certain behavior, and the behavioral pattern identified through the analysis of the video recording by the machine learning algorithm. In addition, each subject's dataset in the training data also comprises a classification any behavioral disorders, developmental delays, or neurological impairments present in the subject. For example, the classification may be autism, autism spectrum disorder (ASD), or non-spectrum. Preferably, the classification comprises a clinical diagnosis, assigned by qualified personnel such as licensed clinical psychologists, in order to improve the predictive accuracy of the machine learning algorithm. The training data may comprise datasets available from large data repositories, such as Autism Diagnostic Interview-Revised (ADI-R) data and/or Autism Diagnostic Observation Schedule (ADOS) data available from the Autism Genetic Resource Exchange (AGRE), or any datasets available from any other suitable repository of data (e.g., Boston Autism Consortium (AC), Simons Foundation, National Database for Autism Research, etc.). Alternatively or in combination, the training data may comprise large self-reported datasets, which can be crowd-sourced from users (e.g., via websites, mobile applications, etc.).

The preprocessing module 305 can be configured to apply one or more transformations to the extracted training data to clean and normalize the data, for example. The preprocessing module can be configured to discard data which contain spurious metadata or contain very few observations. The preprocessing module can be further configured to standardize the encoding of behavioral units.

The training module 310 is used to train a machine learning algorithm. The machine learning algorithm can be constructed to capture, based on the training data, the statistical relationship, if any, between a given behavioral unit, higher order behavior, or behavior pattern and a specific behavioral disorder, developmental delay, or neurological impairment. The machine learning algorithm may, for example, comprise the statistical correlations between a plurality of clinical characteristics and clinical diagnoses of one or more behavioral disorders, developmental delays, or neurological impairments. A given behavioral unit may have a different predictive utility for classifying each of the plurality behavioral disorders, developmental delays, or neurological impairments to be evaluated. A probability score may be extracted that describes the probability of the specific behavioral disorders, developmental delays, or neurological impairments for predicting each of the plurality of behavioral disorders, developmental delays, or neurological impairments. The machine learning algorithm can be used to extract these statistical relationships from the training data and build a model that can yield an accurate prediction of a disorder when a dataset comprising one or more behavioral disorders, developmental delays, or neurological impairments is fitted to the model.

One or more machine learning algorithms may be used to construct the machine learning algorithm used to provide probability scores, such as support vector machines that deploy stepwise backwards behavioral unit selection and/or graphical models, both of which can have advantages of inferring interactions between behavioral units. Machine learning algorithms or other statistical algorithms may be used, such as convolutional neural networks (CNN), recurrent neural networks (RNN), long short term memory networks (LSTM), alternating decision trees (ADTree), Decision Stumps, functional trees (FT), logistic model trees (LMT), logistic regression, Random Forests, linear classifiers, or any machine learning algorithm or statistical algorithm known in the art. One or more algorithms may be used together to generate an ensemble method, wherein the ensemble method may be optimized using a machine learning ensemble meta-algorithm such as a boosting (e.g., AdaBoost, LPBoost, TotalBoost, BrownBoost, MadaBoost, LogitBoost, etc.) to reduce bias and/or variance. Once a machine learning algorithm is derived from the training data, the model may be used as a prediction tool to assess the risk of a subject for having one or more disorders. Machine learning analyses may be performed using one or more of many programming languages and platforms known in the art, such as TensorFlow, Keras, R, Weka, Python, and/or Matlab, for example.

Alternatively or in combination, behavioral units, higher order behaviors, or behavioral patterns of interest in a subject may be evaluated through structured interactions with the subject. For example, the subject may be asked to play a game such as a computer game, and the performance of the subject on the game may be used to evaluate one or more behavioral units, higher order behaviors, or behavioral patterns of the subject. The subject may be presented with one or more stimuli (e.g., visual stimuli presented to the subject via a display), and the response of the subject to the stimuli may be used to evaluate the subject's behavioral units, higher order behaviors, or behavioral patterns. The subject may be asked to perform a certain task (e.g., subject may be asked to pop bubbles with his or her fingers), and the response of the subject to the request or the ability of the subject to carry out the requested task may be used to evaluate to the subject's behavioral units, higher order behaviors, or behavioral patterns.

Systems and Devices

Figure 4:
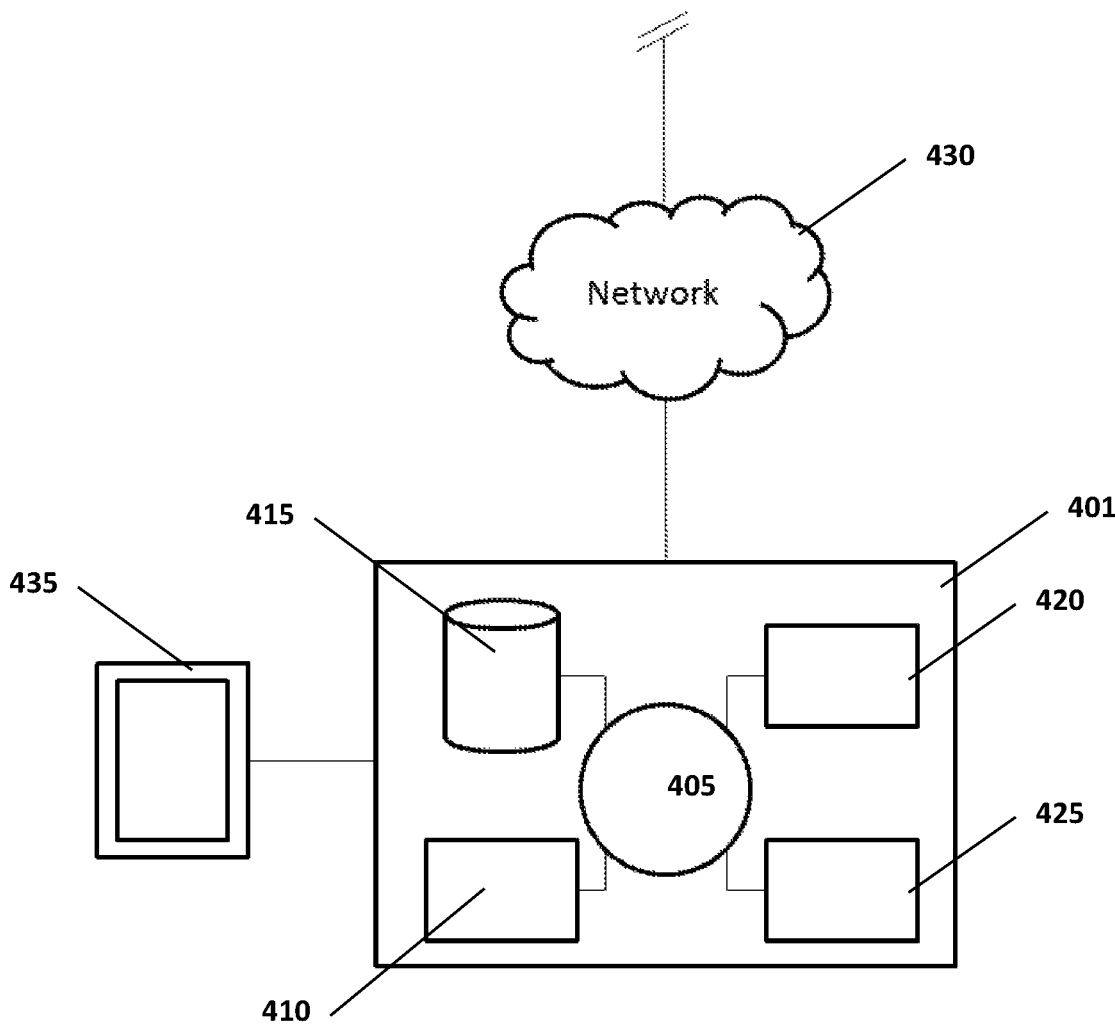
FIG. 4 shows a computer device suitable for incorporation with the platforms, devices, and methods described herein.

The present disclosure provides computer control devices that are programmed to implement methods of the disclosure. FIG. 4 shows a computer device 401 suitable for incorporation with the platforms, devices, and methods described herein. The computer device 401 can process various aspects of information of the present disclosure, such as, for example, questions and answers, responses, statistical analyses. The computer device 401 can be an electronic device of a user or a computer device that is remotely located with respect to the electronic device. The electronic device can be a mobile electronic device.

The computer device 401 includes a central processing unit (CPU, also "processor" and "computer processor" herein) 405, which can be a single core or multi core processor, or a plurality of processors for parallel processing. The computer device 401 also includes memory or memory location 410 (e.g., random-access memory, read-only memory, flash memory), electronic storage unit 415 (e.g., hard disk), communication interface 420 (e.g., network adapter) for communicating with one or more other devices, and peripheral devices 425, such as cache, other memory, data storage and/or electronic display adapters. The memory 410, storage unit 415, interface 420 and peripheral devices 425 are in communication with the CPU 405 through a communication bus (solid lines), such as a motherboard. The storage unit 415 can be a data storage unit (or data repository) for storing data. The computer device 401 can be operatively coupled to a computer network ("network") 430 with the aid of the communication interface 420. The network 430 can be the Internet, an internet and/or extranet, or an intranet and/or extranet that is in communication with the Internet. The network 430 in some cases is a telecommunication and/or data network. The network 430 can include one or more computer servers, which can enable distributed computing, such as cloud computing. The network 430, in some cases with the aid of the computer device 401, can implement a peer-to-peer network, which may enable devices coupled to the computer device 401 to behave as a client or a server.

The CPU 405 can execute a sequence of machine-readable instructions, which can be embodied in a program or software. The instructions may be stored in a memory location, such as the memory 410. The instructions can be directed to the CPU 405, which can subsequently program or otherwise configure the CPU 405 to implement methods of the present disclosure. Examples of operations performed by the CPU 405 can include fetch, decode, execute, and writeback.

The CPU 405 can be part of a circuit, such as an integrated circuit. One or more other components of the device 401 can be included in the circuit. In some cases, the circuit is an application specific integrated circuit (ASIC).

The storage unit 415 can store files, such as drivers, libraries and saved programs. The storage unit 415 can store user data, e.g., user preferences and user programs. The computer device 401 in some cases can include one or more additional data storage units that are external to the computer device 401, such as located on a remote server that is in communication with the computer device 401 through an intranet or the Internet.

The computer device 401 can communicate with one or more remote computer devices through the network 430. For instance, the computer device 401 can communicate with a remote computer device of a user (e.g., a parent). Examples of remote computer devices and mobile communication devices include personal computers (e.g., portable PC), slate or tablet PC's (e.g., Apple® iPad, Samsung® Galaxy Tab), telephones, Smart phones (e.g., Apple® iPhone, Android-enabled device, Blackberry®), or personal digital assistants. The user can access the computer device 401 with the network 430.

Methods as described herein can be implemented by way of machine (e.g., computer processor) executable code stored on an electronic storage location of the computer device 401, such as, for example, on the memory 410 or electronic storage unit 415. The machine executable or machine readable code can be provided in the form of software. During use, the code can be executed by the processor 405. In some cases, the code can be retrieved from the storage unit 415 and stored on the memory 410 for ready access by the processor 405. In some situations, the electronic storage unit 415 can be precluded, and machine-executable instructions are stored on memory 410.

The code can be pre-compiled and configured for use with a machine have a processer adapted to execute the code, or the code can be compiled during runtime. The code can be supplied in a programming language that can be selected to enable the code to execute in a pre-compiled or as-compiled fashion.

Aspects of the devices and methods provided herein, such as the computer device 401, can be embodied in programming. Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such memory (e.g., read-only memory, random-access memory, flash memory) or a hard disk. "Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

Hence, a machine readable medium, such as computer-executable code, may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer device. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

The computer device 401 can include or be in communication with an electronic display 435 that comprises a user interface (UI) for providing, for example, questions and answers, analysis results, recommendations. Examples of UI's include, without limitation, a graphical user interface (GUI) and web-based user interface.

Platforms, devise, and methods of the present disclosure can be implemented by way of one or more algorithms and with instructions provided with one or more processors as disclosed herein. An algorithm can be implemented by way of software upon execution by the central processing unit 405. The algorithm can be, for example, random forest, graphical models, support vector machine or other.

Although the above steps show a method of a device in accordance with an example, a person of ordinary skill in the art will recognize many variations based on the teaching described herein. The steps may be completed in a different order. Steps may be added or deleted. Some of the steps may comprise sub-steps. Many of the steps may be repeated as often as if beneficial to the platform.

Each of the examples as described herein can be combined with one or more other examples. Further, one or more components of one or more examples can be combined with other examples.

Treatments

The platforms, devices, and methods disclosed herein can incorporate pharmaceutical treatment. In some embodiments, drugs are used to treat behavioral disorders, developmental delays, and neurologic impairments disclosed herein. In some embodiments, the efficacy of drug treatment is monitored or evaluated. In some embodiments, a method for administering a drug to a subject may comprise: detecting a behavioral disorders, developmental delays, or neurological impairments of the subject with a machine learning algorithms disclosed herein; and administering the drug to the subject in response to the detected behavioral disorders, developmental delays, or neurological impairments. The behavioral disorder, developmental delay, or neurological impairment may comprise attention deficit disorder (ADD), obsessive-compulsive disorder, acute stress disorder, adjustment disorder, agoraphobia, Alzheimer's disease, anorexia nervosa, anxiety disorders, bereavement, bipolar disorder, body dysmorphic disorder, brief psychotic disorder, bulimia nervosa, conduct disorder, delusional disorder, depersonalization disorder, depression, disruptive mood dysregulation disorder, dissociative amnesia, dissociative disorder, dissociative fugue, dysthymic disorder, eating disorders, gender dysphoria, generalized anxiety disorder, hoarding disorder, intermittent explosive disorder, kleptomania, panic disorder, Parkinson's disease, pathological gambling, postpartum depression, posttraumatic stress disorder, premenstrual dysphoric disorder, pseudobulbar affect, pyromania, schizoaffective disorder, schizophrenia, schizophreniform disorder, seasonal affective disorder, shared psychotic disorder, social anxiety phobia, specific phobia, stereotypic movement disorder, Tourette's disorder, transient tic disorder, or trichotillomania.

The behavioral disorder, developmental delay, or neurological impairment may comprise autism spectrum disorder, and the drug may be selected from the group consisting of risperidone, quetiapine, amphetamine, dextroamphetamine, methylphenidate, methamphetamine, dextroamphetamine, dexmethylphenidate, guanfacine, atomoxetine, lisdexamfetamine, clonidine, and aripiprazolecomprise; or the behavioral disorder, developmental delay, or neurological impairment may comprise attention deficit disorder (ADD), and the drug may be selected from the group consisting of amphetamine, dextroamphetamine, methylphenidate, methamphetamine, dextroamphetamine, dexmethylphenidate, guanfacine, atomoxetine, lisdexamfetamine, clonidine, and modafinil; or the behavioral disorder, developmental delay, or neurological impairment may comprise obsessive-compulsive disorder, and the drug may be selected from the group consisting of buspirone, sertraline, escitalopram, citalopram, fluoxetine, paroxetine, venlafaxine, clomipramine, and fluvoxamine; or the behavioral disorder, developmental delay, or neurological impairment may comprise acute stress disorder, and the drug may be selected from the group consisting of propranolol, citalopram, escitalopram, sertraline, paroxetine, fluoextine, venlafaxine, mirtazapine, nefazodone, carbamazepine, divalproex, lamotrigine, topiramate, prazosin, phenelzine, imipramine, diazepam, clonazepam, lorazepam, and alprazolam; or the behavioral disorder, developmental delay, or neurological impairment may comprise adjustment disorder, and the drug may be selected from the group consisting of busiprone, escitalopram, sertraline, paroxetine, fluoextine, diazepam, clonazepam, lorazepam, and alprazolam; or behavioral disorder, developmental delay, or neurological impairment may comprise agoraphobia, and the drug may be selected from the group consisting of diazepam, clonazepam, lorazepam, alprazolam, citalopram, escitalopram, sertraline, paroxetine, fluoextine, and busiprone; or the behavioral disorder, developmental delay, or neurological impairment may comprise Alzheimer's disease, and the drug may be selected from the group consisting of donepezil, galantamine, memantine, and rivastigmine; or the behavioral disorder, developmental delay, or neurological impairment may comprise anorexia nervosa, and the drug may be selected from the group consisting of olanzapine, citalopram, escitalopram, sertraline, paroxetine, and fluoxetine; or the behavioral disorder, developmental delay, or neurological impairment may comprise anxiety disorders, and the drug may be selected from the group consisting of sertraline, escitalopram, citalopram, fluoxetine, diazepam, buspirone, venlafaxine, duloxetine, imipramine, desipramine, clomipramine, lorazepam, clonazepam, and pregabalin; or the behavioral disorder, developmental delay, or neurological impairment may comprise bereavement, and the drug may be selected from the group consisting of citalopram, duloxetine, and doxepin; or the behavioral disorder, developmental delay, or neurological impairment may comprise binge eating disorder, and the drug may be selected from the group consisting of lisdexamfetamine; or the behavioral disorder, developmental delay, or neurological impairment may comprise bipolar disorder, and the drug may be selected from the group consisting of topiramate, lamotrigine, oxcarbazepine, haloperidol, risperidone, quetiapine, olanzapine, aripiprazole, and fluoxetine; or the behavioral disorder, developmental delay, or neurological impairment may comprise body dysmorphic disorder, and the drug may be selected from the group consisting of sertraline, escitalopram, and citalopram; or the behavioral disorder, developmental delay, or neurological impairment may comprise brief psychotic disorder, and the drug may be selected from the group consisting of clozapine, asenapine, olanzapine, and quetiapine; or the behavioral disorder, developmental delay, or neurological impairment may comprise bulimia nervosa, and the drug may be selected from the group consisting of sertraline and fluoxetine; or the behavioral disorder, developmental delay, or neurological impairment may comprise conduct disorder, and the drug may be selected from the group consisting of lorazepam, diazepam, and clobazam; or the behavioral disorder, developmental delay, or neurological impairment may comprise delusional disorder, and the drug may be selected from the group consisting of clozapine, asenapine, risperidone, venlafaxine, bupropion, and buspirone; the behavioral disorder, developmental delay, or neurological impairment may comprise depersonalization disorder, and the drug may be selected from the group consisting of sertraline, fluoxetine, alprazolam, diazepam, and citalopram; or the behavioral disorder, developmental delay, or neurological impairment may comprise depression, and the drug may be selected from the group consisting of sertraline, fluoxetine, citalopram, bupropion, escitalopram, venlafaxine, aripiprazole, buspirone, vortioxetine, and vilazodone; or the behavioral disorder, developmental delay, or neurological impairment may comprise disruptive mood dysregulation disorder, and the drug may be selected from the group consisting of quetiapine, clozapine, asenapine, and pimavanserin; or the behavioral disorder, developmental delay, or neurological impairment may comprise dissociative amnesia, and the drug may be selected from the group consisting of alprazolam, diazepam, lorazepam, and chlordiazepoxide; or the behavioral disorder, developmental delay, or neurological impairment may comprise dissociative disorder, and the drug may be selected from the group consisting of bupropion, vortioxetine, and vilazodone; or the behavioral disorder, developmental delay, or neurological impairment may comprise dissociative fugue, and the drug may be selected from the group consisting of amobarbital, aprobarbital, butabarbital, and methohexitlal; or the behavioral disorder, developmental delay, or neurological impairment may comprise dysthymic disorder, and the drug may be selected from the group consisting of bupropion, venlafaxine, sertraline, and citalopram; the behavioral disorder, developmental delay, or neurological impairment may comprise eating disorders, and the drug may be selected from the group consisting of olanzapine, citalopram, escitalopram, sertraline, paroxetine, and fluoxetine; or the behavioral disorder, developmental delay, or neurological impairment may comprise gender dysphoria, and the drug may be selected from the group consisting of estrogen, prostogen, and testosterone; or the behavioral disorder, developmental delay, or neurological impairment may comprise generalized anxiety disorder, and the drug may be selected from the group consisting of venlafaxine, duloxetine, buspirone, sertraline, and fluoxetine; or the behavioral disorder, developmental delay, or neurological impairment may comprise hoarding disorder, and the drug may be selected from the group consisting of buspirone, sertraline, escitalopram, citalopram, fluoxetine, paroxetine, venlafaxine, and clomipramine; or the behavioral disorder, developmental delay, or neurological impairment may comprise intermittent explosive disorder, and the drug may be selected from the group consisting of asenapine, clozapine, olanzapine, and pimavanserin; or the behavioral disorder, developmental delay, or neurological impairment may comprise kleptomania, and the drug may be selected from the group consisting of escitalopram, fluvoxamine, fluoxetine, and paroxetine; or the behavioral disorder, developmental delay, or neurological impairment may comprise panic disorder, and the drug may be selected from the group consisting of bupropion, vilazodone, and vortioxetine; or the behavioral disorder, developmental delay, or neurological impairment may comprise Parkinson's disease, and the drug may be selected from the group consisting of rivastigmine, selegiline, rasagiline, bromocriptine, amantadine, cabergoline, and benztropine; or the behavioral disorder, developmental delay, or neurological impairment may comprise pathological gambling, and the drug may be selected from the group consisting of bupropion, vilazodone, and vartioxetine; or the behavioral disorder, developmental delay, or neurological impairment may comprise postpartum depression, and the drug may be selected from the group consisting of sertraline, fluoxetine, citalopram, bupropion, escitalopram, venlafaxine, aripiprazole, buspirone, vortioxetine, and vilazodone; or the behavioral disorder, developmental delay, or neurological impairment may comprise posttraumatic stress disorder, and the drug may be selected from the group consisting of sertraline, fluoxetine, and paroxetine; or the behavioral disorder, developmental delay, or neurological impairment may comprise premenstrual dysphoric disorder, and the drug may be selected from the group consisting of estadiol, drospirenone, sertraline, citalopram, fluoxetine, and busiprone; or the behavioral disorder, developmental delay, or neurological impairment may comprise pseudobulbar affect, and the drug may be selected from the group consisting of dextromethorphan hydrobromide, and quinidine sulfate; or the behavioral disorder, developmental delay, or neurological impairment may comprise pyromania, and the drug may be selected from the group consisting of clozapine, asenapine, olanzapine, paliperidone, and quetiapine; or the behavioral disorder, developmental delay, or neurological impairment may comprise schizoaffective disorder, and the drug may be selected from the group consisting of sertraline, carbamazepine, oxcarbazepine, valproate, haloperidol, olanzapine, and loxapine; or the behavioral disorder, developmental delay, or neurological impairment may comprise schizophrenia, and the drug may be selected from the group consisting of chlopromazine, haloperidol, fluphenazine, risperidone, quetiapine, ziprasidone, olanzapine, perphenazine, aripiprazole, and prochlorperazine; or the behavioral disorder, developmental delay, or neurological impairment may comprise schizophreniform disorder, and the drug may be selected from the group consisting of paliperidone, clozapine, and risperidone; or the behavioral disorder, developmental delay, or neurological impairment may comprise seasonal affective disorder, and the drug may be selected from the group consisting of sertraline, and fluoxetine; or the behavioral disorder, developmental delay, or neurological impairment may comprise shared psychotic disorder, and the drug may be selected from the group consisting of clozapine, pimavanserin, risperidone, and lurasidone; or the behavioral disorder, developmental delay, or neurological impairment may comprise social anxiety phobia, and the drug may be selected from the group consisting of amitriptyline, bupropion, citalopram, fluoxetine, sertraline, and venlafaxine; or the behavioral disorder, developmental delay, or neurological impairment may comprise specific phobia, and the drug may be selected from the group consisting of diazepam, estazolam, quazepam, and alprazolam; or the behavioral disorder, developmental delay, or neurological impairment may comprise stereotypic movement disorder, and the drug may be selected from the group consisting of risperidone, and clozapine; or the behavioral disorder, developmental delay, or neurological impairment may comprise Tourette's disorder, and the drug may be selected from the group consisting of haloperidol, fluphenazine, risperidone, ziprasidone, pimozide, perphenazine, and aripiprazole; or the behavioral disorder, developmental delay, or neurological impairment may comprise transient tic disorder, and the drug may be selected from the group consisting of guanfacine, clonidine, pimozide, risperidone, citalopram, escitalopram, sertraline, paroxetine, and fluoxetine; or the behavioral disorder, developmental delay, or neurological impairment may comprise trichotillomania, and the drug may be selected from the group consisting of sertraline, fluoxetine, paroxetine, desipramine, and clomipramine.

Devices and Systems for Evaluating Behavioral Disorders, Developmental Delays, and Neurologic Impairments Described herein are platforms, devices, and methods for determining the developmental progress of a subject. For example, the described platforms, devices, and methods can identify a subject as developmentally advanced in one or more areas of development or cognitively declining in one or more cognitive functions, or identify a subject as developmentally delayed or at risk of having one or more behavioral disorders, developmental delays, or neurologic impairments. The platforms, devices, and methods disclosed can determine the subject's progress by evaluating a plurality of behavioral units of the subject based on an assessment model, wherein the assessment model can be generated from large datasets of relevant subject populations using machine-learning approaches.

The platforms, devices, and methods are herein described in the context of identifying one or more behavioral disorders, developmental delays, or neurologic impairments of a subject. For example, the platforms, devices, and methods can be used to identify a subject as developmentally advanced, by identifying one or more areas of development in which the subject is advanced. To identify one or more areas of advanced development, the platforms, devices, and methods may be configured to assess one or more features or characteristics of the subject that are related to advanced or gifted behaviors, for example. The platforms, devices, and methods as described can also be used to identify a subject as cognitively declining in one or more cognitive functions, by evaluating the one or more cognitive functions of the subject.

Described herein are platforms, devices, and methods for diagnosing or assessing behavioral units, behavioral functions, and/or higher level behavioral or behavioral patterns associated with one or more behavioral disorders, developmental delays, or neurologic impairments in a subject. This process can include evaluation of cognitive functions, features, or characteristics that relate to one or more behavioral disorders, developmental delays, or neurologic impairments. For example, a person may be evaluated for speech and/or language proficiency based on the behavioral units, higher order behavior, and/or behavioral patterns disclosed herein.

Described herein are platforms, devices, and methods for diagnosing or assessing risk for one or more behavioral disorders, developmental delays, or neurologic impairments in a subject. The method may comprise providing a data processing module, which can be utilized to construct and administer an assessment procedure for screening a subject for one or more of a plurality of developmental disorders or conditions. The assessment procedure can evaluate a plurality of features or characteristics of the subject through the use of the machine learning algorithm, wherein each feature can be related to the likelihood of the subject having at least one of the plurality of disorders screenable by the procedure. Each feature may be related to the likelihood of the subject having two or more related disorders, wherein the two or more related disorders may have one or more related symptoms. The features can be assessed in many ways. For example, the features may be assessed via a subject's answers to questions, observations of a subject, or results of a structured interaction with a subject, as described herein.

In some embodiments, systems and devices disclosed herein comprise a recording device. In some embodiments, video and/or audio recording are taken with a mobile device. In some embodiments, the mobile device is a smartphone, a tablet, a smartwatch, or any device with a mobile camera or recording feature. In some embodiments, the video and/or audio recording is taken with a stationary camera and/or microphone. For example, an individual may be asked questions in a clinician's office and have their responses recorded with a camera on a tripod with a mounted microphone. In some embodiments, the camera is a high-definition camera. In some embodiments, the individual is prompted to provide a response through the device interface, for example, selecting or typing answers or responses to questions or prompts within a touchscreen interface of the device. In some embodiments, the audio itself is recorded and analyzed to gauge behavior, for example, determining the level of speech and language. The information obtained based on analysis of these inputs (e.g., audio, video, responses, etc.) can be evaluated to determine the appropriate therapeutic. A digital therapeutic can be an interactive activity in which the activity is dynamically modified or changed while the individual is engaging in the activity based analysis of the inputs. Various modalities can be utilized in which the individual is continually engaging in an activity, being monitored during the activity, and the activity is dynamically modified or adjusted based on real-time analysis of the individual's input or responses. As an example, a storytelling activity can guide the individual through an interactive story that can split down different storylines or threads of varying difficulty in which the appropriate thread is selected based on an assessment of the individual's speech and language level in relation to the respective difficulties of the available threads.

In some cases, the device operates at a frame rate of ~15-20 FPS, which enables facial expressions recognition within 100 ms. The device can operate at a frame rate of 10 FPS to 100 FPS. The device can operate at a frame rate of 1 FPS to 10 FPS, 1 FPS to 20 FPS, 1 FPS to 30 FPS, 1 FPS to 40 FPS, 1 FPS to 50 FPS, 1 FPS to 100 FPS, 10 FPS to 15 FPS, 10 FPS to 20 FPS, 10 FPS to 25 FPS, 10 FPS to 30 FPS, 10 FPS to 35 FPS, 10 FPS to 40 FPS, 10 FPS to 45 FPS, 10 FPS to 50 FPS, 10 FPS to 60 FPS, 10 FPS to 80 FPS, 10 FPS to 100 FPS, 15 FPS to 20 FPS, 15 FPS to 25 FPS, 15 FPS to 30 FPS, 15 FPS to 35 FPS, 15 FPS to 40 FPS, 15 FPS to 45 FPS, 15 FPS to 50 FPS, 15 FPS to 60 FPS, 15 FPS to 80 FPS, 15 FPS to 100 FPS, 20 FPS to 25 FPS, 20 FPS to 30 FPS, 20 FPS to 35 FPS, 20 FPS to 40 FPS, 20 FPS to 45 FPS, 20 FPS to 50 FPS, 20 FPS to 60 FPS, 20 FPS to 80 FPS, 20 FPS to 100 FPS, 25 FPS to 30 FPS, 25 FPS to 35 FPS, 25 FPS to 40 FPS, 25 FPS to 45 FPS, 25 FPS to 50 FPS, 25 FPS to 60 FPS, 25 FPS to 80 FPS, 25 FPS to 100 FPS, 30 FPS to 35 FPS, 30 FPS to 40 FPS, 30 FPS to 45 FPS, 30 FPS to 50 FPS, 30 FPS to 60 FPS, 30 FPS to 80 FPS, 30 FPS to 100 FPS, 35 FPS to 40 FPS, 35 FPS to 45 FPS, 35 FPS to 50 FPS, 35 FPS to 60 FPS, 35 FPS to 80 FPS, 35 FPS to 100 FPS, 40 FPS to 45 FPS, 40 FPS to 50 FPS, 40 FPS to 60 FPS, 40 FPS to 80 FPS, 40 FPS to 100 FPS, 45 FPS to 50 FPS, 45 FPS to 60 FPS, 45 FPS to 80 FPS, 45 FPS to 100 FPS, 50 FPS to 60 FPS, 50 FPS to 80 FPS, 50 FPS to 100 FPS, 60 FPS to 80 FPS, 60 FPS to 100 FPS, or 80 FPS to 100 FPS. The device can operate at a frame rate of 10 FPS, 15 FPS, 20 FPS, 25 FPS, 30 FPS, 35 FPS, 40 FPS, 45 FPS, 50 FPS, 60 FPS, 80 FPS, or 100 FPS. The device can operate at a frame rate of at least 1 FPS, 5 FPS, 10 FPS, 15 FPS, 20 FPS, 25 FPS, 30 FPS, 35 FPS, 40 FPS, 45 FPS, 50 FPS, 60 FPS, or 80 FPS. The device can operate at a frame rate of at most 15 FPS, 20 FPS, 25 FPS, 30 FPS, 35 FPS, 40 FPS, 45 FPS, 50 FPS, 60 FPS, 80 FPS, or 100 FPS.

In some cases, the device can detect facial expressions or motions within 10 ms to 200 ms. The device can detect facial expressions or motions within 10 ms to 20 ms, 10 ms to 30 ms, 10 ms to 40 ms, 10 ms to 50 ms, 10 ms to 60 ms, 10 ms to 70 ms, 10 ms to 80 ms, 10 ms to 90 ms, 10 ms to 100 ms, 10 ms to 150 ms, 10 ms to 200 ms, 20 ms to 30 ms, 20 ms to 40 ms, 20 ms to 50 ms, 20 ms to 60 ms, 20 ms to 70 ms, 20 ms to 80 ms, 20 ms to 90 ms, 20 ms to 100 ms, 20 ms to 150 ms, 20 ms to 200 ms, 30 ms to 40 ms, 30 ms to 50 ms, 30 ms to 60 ms, 30 ms to 70 ms, 30 ms to 80 ms, 30 ms to 90 ms, 30 ms to 100 ms, 30 ms to 150 ms, 30 ms to 200 ms, 40 ms to 50 ms, 40 ms to 60 ms, 40 ms to 70 ms, 40 ms to 80 ms, 40 ms to 90 ms, 40 ms to 100 ms, 40 ms to 150 ms, 40 ms to 200 ms, 50 ms to 60 ms, 50 ms to 70 ms, 50 ms to 80 ms, 50 ms to 90 ms, 50 ms to 100 ms, 50 ms to 150 ms, 50 ms to 200 ms, 60 ms to 70 ms, 60 ms to 80 ms, 60 ms to 90 ms, 60 ms to 100 ms, 60 ms to 150 ms, 60 ms to 200 ms, 70 ms to 80 ms, 70 ms to 90 ms, 70 ms to 100 ms, 70 ms to 150 ms, 70 ms to 200 ms, 80 ms to 90 ms, 80 ms to 100 ms, 80 ms to 150 ms, 80 ms to 200 ms, 90 ms to 100 ms, 90 ms to 150 ms, 90 ms to 200 ms, 100 ms to 150 ms, 100 ms to 200 ms, or 150 ms to 200 ms. The device can detect facial expressions or motions within 10 ms, 20 ms, 30 ms, 40 ms, 50 ms, 60 ms, 70 ms, 80 ms, 90 ms, 100 ms, 150 ms, or 200 ms. The device can detect facial expressions or motions within at least 10 ms, 20 ms, 30 ms, 40 ms, 50 ms, 60 ms, 70 ms, 80 ms, 90 ms, 100 ms, or 150 ms. The device can detect facial expressions or motions within at most 20 ms, 30 ms, 40 ms, 50 ms, 60 ms, 70 ms, 80 ms, 90 ms, 100 ms, 150 ms, or 200 ms.

In some embodiments, systems and devices disclosed herein comprise a biosensor for taking a measurement of the user. For example, a biosensor may be used to measure an individual's heartbeat, blood sugar level, rate breathing or activity level. In some embodiments, the biosensor comprises an electrocardiogram or electroencephalogram sensor, potentiometer, accelerometer, or gyrometer. Such measurements can be used to evaluate or augment the evaluation of an individual's response or interaction with a digital diagnostic and/or therapeutic activity, for example, an interactive storytelling activity during which an individual is guided through a story that elicits verbal, video, and/or digital responses that are used to dynamically modify the activity.

Digital Processing Device

In some embodiments, the platforms, systems, media, and methods described herein include a digital processing device, or use of the same. In further embodiments, the digital processing device includes one or more hardware central processing units (CPUs) or general purpose graphics processing units (GPGPUs) that carry out the device's functions. In still further embodiments, the digital processing device further comprises an operating system configured to perform executable instructions. In some embodiments, the digital processing device is optionally connected a computer network. In further embodiments, the digital processing device is optionally connected to the Internet such that it accesses the World Wide Web. In still further embodiments, the digital processing device is optionally connected to a cloud computing infrastructure. In other embodiments, the digital processing device is optionally connected to an intranet. In other embodiments, the digital processing device is optionally connected to a data storage device.

In accordance with the description herein, suitable digital processing devices include, by way of non-limiting examples, server computers, desktop computers, laptop computers, notebook computers, sub-notebook computers, netbook computers, netpad computers, set-top computers, media streaming devices, handheld computers, Internet appliances, mobile smartphones, tablet computers, personal digital assistants, video game consoles, and vehicles. Those of skill in the art will recognize that many smartphones are suitable for use in the system described herein. Those of skill in the art will also recognize that select televisions, video players, and digital music players with optional computer network connectivity are suitable for use in the system described herein. Suitable tablet computers include those with booklet, slate, and convertible configurations, known to those of skill in the art.

In some embodiments, the digital processing device includes an operating system configured to perform executable instructions. The operating system is, for example, software, including programs and data, which manages the device's hardware and provides services for execution of applications. Those of skill in the art will recognize that suitable server operating systems include, by way of non-limiting examples, FreeBSD, OpenBSD, NetBSD®, Linux, Apple® Mac OS X Server®, Oracle® Solaris®, Windows Server®, and Novell® NetWare®. Those of skill in the art will recognize that suitable personal computer operating systems include, by way of non-limiting examples, Microsoft® Windows®, Apple® Mac OS X®, UNIX®, and UNIX-like operating systems such as GNU/Linux®. In some embodiments, the operating system is provided by cloud computing. Those of skill in the art will also recognize that suitable mobile smart phone operating systems include, by way of non-limiting examples, Nokia® Symbian® OS, Apple® iOS®, Research In Motion® BlackBerry OS®, Google® Android®, Microsoft® Windows Phone® OS, Microsoft® Windows Mobile® OS, Linux®, and Palm® WebOS®. Those of skill in the art will also recognize that suitable media streaming device operating systems include, by way of non-limiting examples, Apple TV®, Roku®, Boxee®, Google TV®, Google Chromecast®, Amazon Fire®, and Samsung® HomeSync®. Those of skill in the art will also recognize that suitable video game console operating systems include, by way of non-limiting examples, Sony®PS3®, Sony® PS4®, Microsoft® Xbox 360®, Microsoft Xbox One, Nintendo® Wii®, Nintendo® Wii U®, and Ouya®.

In some embodiments, the device includes a storage and/or memory device. The storage and/or memory device is one or more physical apparatuses used to store data or programs on a temporary or permanent basis. In some embodiments, the device is volatile memory and requires power to maintain stored information. In some embodiments, the device is non-volatile memory and retains stored information when the digital processing device is not powered. In further embodiments, the non-volatile memory comprises flash memory. In some embodiments, the non-volatile memory comprises dynamic random-access memory (DRAM). In some embodiments, the non-volatile memory comprises ferroelectric random access memory (FRAM). In some embodiments, the non-volatile memory comprises phase-change random access memory (PRAM). In other embodiments, the device is a storage device including, by way of non-limiting examples, CD-ROMs, DVDs, flash memory devices, magnetic disk drives, magnetic tapes drives, optical disk drives, and cloud computing based storage. In further embodiments, the storage and/or memory device is a combination of devices such as those disclosed herein.

In some embodiments, the digital processing device includes a display to send visual information to a user. In some embodiments, the display is a liquid crystal display (LCD). In further embodiments, the display is a thin film transistor liquid crystal display (TFT-LCD). In some embodiments, the display is an organic light emitting diode (OLED) display. In various further embodiments, on OLED display is a passive-matrix OLED (PMOLED) or active-matrix OLED (AMOLED) display. In some embodiments, the display is a plasma display. In other embodiments, the display is a video projector. In yet other embodiments, the display is a head-mounted display in communication with the digital processing device, such as a VR headset. In further embodiments, suitable VR headsets include, by way of non-limiting examples, HTC Vive, Oculus Rift, Samsung Gear VR, Microsoft HoloLens, Razer OSVR, FOVE VR, Zeiss VR One, Avegant Glyph, Freefly VR headset, and the like. In still further embodiments, the display is a combination of devices such as those disclosed herein.

In some embodiments, the digital processing device includes an input device to receive information from a user. In some embodiments, the input device is a keyboard. In some embodiments, the input device is a pointing device including, by way of non-limiting examples, a mouse, trackball, track pad, joystick, game controller, or stylus. In some embodiments, the input device is a touch screen or a multi-touch screen. In other embodiments, the input device is a microphone to capture voice or other sound input. In other embodiments, the input device is a video camera or other sensor to capture motion or visual input. In further embodiments, the input device is a Kinect, Leap Motion, or the like. In still further embodiments, the input device is a combination of devices such as those disclosed herein.

Non-Transitory Computer Readable Storage Medium

In some embodiments, the platforms, systems, media, and methods disclosed herein include one or more non-transitory computer readable storage media encoded with a program including instructions executable by the operating system of an optionally networked digital processing device. In further embodiments, a computer readable storage medium is a tangible component of a digital processing device. In still further embodiments, a computer readable storage medium is optionally removable from a digital processing device. In some embodiments, a computer readable storage medium includes, by way of non-limiting examples, CD-ROMs, DVDs, flash memory devices, solid state memory, magnetic disk drives, magnetic tape drives, optical disk drives, cloud computing systems and services, and the like. In some cases, the program and instructions are permanently, substantially permanently, semi-permanently, or non-transitorily encoded on the media.

Computer Program

In some embodiments, the platforms, systems, media, and methods disclosed herein include at least one computer program, or use of the same. A computer program includes a sequence of instructions, executable in the digital processing device's CPU, written to perform a specified task. Computer readable instructions may be implemented as program modules, such as functions, objects, Application Programming Interfaces (APIs), data structures, and the like, that perform particular tasks or implement particular abstract data types. In light of the disclosure provided herein, those of skill in the art will recognize that a computer program may be written in various versions of various languages.

The functionality of the computer readable instructions may be combined or distributed as desired in various environments. In some embodiments, a computer program comprises one sequence of instructions. In some embodiments, a computer program comprises a plurality of sequences of instructions. In some embodiments, a computer program is provided from one location. In other embodiments, a computer program is provided from a plurality of locations. In various embodiments, a computer program includes one or more software modules. In various embodiments, a computer program includes, in part or in whole, one or more web applications, one or more mobile applications, one or more standalone applications, one or more web browser plug-ins, extensions, add-ins, or add-ons, or combinations thereof.

Web Application

In some embodiments, a computer program includes a web application. In light of the disclosure provided herein, those of skill in the art will recognize that a web application, in various embodiments, utilizes one or more software frameworks and one or more database systems. In some embodiments, a web application is created upon a software framework such as Microsoft® .NET or Ruby on Rails (RoR). In some embodiments, a web application utilizes one or more database systems including, by way of non-limiting examples, relational, non-relational, object oriented, associative, and XML database systems. In further embodiments, suitable relational database systems include, by way of non-limiting examples, Microsoft® SQL Server, mySQL™, and Oracle®. Those of skill in the art will also recognize that a web application, in various embodiments, is written in one or more versions of one or more languages. A web application may be written in one or more markup languages, presentation definition languages, client-side scripting languages, server-side coding languages, database query languages, or combinations thereof. In some embodiments, a web application is written to some extent in a markup language such as Hypertext Markup Language (HTML), Extensible Hypertext Markup Language (XHTML), or eXtensible Markup Language (XML). In some embodiments, a web application is written to some extent in a presentation definition language such as Cascading Style Sheets (CSS). In some embodiments, a web application is written to some extent in a client-side scripting language such as Asynchronous Javascript and XML (AJAX), Flash® Actionscript, Javascript, or Silverlight®. In some embodiments, a web application is written to some extent in a server-side coding language such as Active Server Pages (ASP), ColdFusion®, Perl, Java™, JavaServer Pages (JSP), Hypertext Preprocessor (PHP), Python™, Ruby, Tcl, Smalltalk, WebDNA®, or Groovy. In some embodiments, a web application is written to some extent in a database query language such as Structured Query Language (SQL). In some embodiments, a web application integrates enterprise server products such as IBM® Lotus Domino®. In some embodiments, a web application includes a media player element. In various further embodiments, a media player element utilizes one or more of many suitable multimedia technologies including, by way of non-limiting examples, Adobe® Flash®, HTML 5, Apple® QuickTime®, Microsoft® Silverlight®, Java™, and Unity®.

Mobile Application

In some embodiments, a computer program includes a mobile application provided to a mobile digital processing device. In some embodiments, the mobile application is provided to a mobile digital processing device at the time it is manufactured. In other embodiments, the mobile application is provided to a mobile digital processing device via the computer network described herein.

In view of the disclosure provided herein, a mobile application is created by techniques known to those of skill in the art using hardware, languages, and development environments known to the art. Those of skill in the art will recognize that mobile applications are written in several languages. Suitable programming languages include, by way of non-limiting examples, C, C++, C#, Objective-C, Java™, Javascript, Pascal, Object Pascal, Python™, Ruby, VB.NET, WML, and XHTML/HTML with or without CSS, or combinations thereof.

Suitable mobile application development environments are available from several sources. Commercially available development environments include, by way of non-limiting examples, AirplaySDK, alcheMo, Appcelerator®, Celsius, Bedrock, Flash Lite, .NET Compact Framework, Rhomobile, and WorkLight Mobile Platform. Other development environments are available without cost including, by way of non-limiting examples, Lazarus, MobiFlex, MoSync, and Phonegap. Also, mobile device manufacturers distribute software developer kits including, by way of non-limiting examples, iPhone and iPad (iOS) SDK, Android™ SDK, BlackBerry® SDK, BREW SDK, Palm® OS SDK, Symbian SDK, webOS SDK, and Windows® Mobile SDK.

Those of skill in the art will recognize that several commercial forums are available for distribution of mobile applications including, by way of non-limiting examples, Apple® App Store, Google® Play, Chrome Web Store, BlackBerry® App World, App Store for Palm devices, App Catalog for webOS, Windows® Marketplace for Mobile, Ovi Store for Nokia® devices, Samsung® Apps, and Nintendo® DSi Shop.

Standalone Application

In some embodiments, a computer program includes a standalone application, which is a program that is run as an independent computer process, not an add-on to an existing process, e.g., not a plug-in. Those of skill in the art will recognize that standalone applications are often compiled. A compiler is a computer program(s) that transforms source code written in a programming language into binary object code such as assembly language or machine code. Suitable compiled programming languages include, by way of non-limiting examples, C, C++, Objective-C, COBOL, Delphi, Eiffel, Java™, Lisp, Python™, Visual Basic, and VB .NET, or combinations thereof. Compilation is often performed, at least in part, to create an executable program. In some embodiments, a computer program includes one or more executable complied applications.

Web Browser Plug-In

In some embodiments, the computer program includes a web browser plug-in (e.g., extension, etc.). In computing, a plug-in is one or more software components that add specific functionality to a larger software application. Makers of software applications support plug-ins to enable third-party developers to create abilities which extend an application, to support easily adding new features, and to reduce the size of an application. When supported, plug-ins enable customizing the functionality of a software application. For example, plug-ins are commonly used in web browsers to play video, generate interactivity, scan for viruses, and display particular file types. Those of skill in the art will be familiar with several web browser plug-ins including, Adobe® Flash® Player, Microsoft® Silverlight®, and Apple® QuickTime®.

In view of the disclosure provided herein, those of skill in the art will recognize that several plug-in frameworks are available that enable development of plug-ins in various programming languages, including, by way of non-limiting examples, C++, Delphi, Java™, PHP, Python™, and VB .NET, or combinations thereof.

Web browsers (also called Internet browsers) are software applications, designed for use with network-connected digital processing devices, for retrieving, presenting, and traversing information resources on the World Wide Web. Suitable web browsers include, by way of non-limiting examples, Microsoft® Internet Explorer®, Mozilla® Firefox®, Google® Chrome, Apple® Safari®, Opera Software® Opera®, and KDE Konqueror. In some embodiments, the web browser is a mobile web browser. Mobile web browsers (also called microbrowsers, mini-browsers, and wireless browsers) are designed for use on mobile digital processing devices including, by way of non-limiting examples, handheld computers, tablet computers, netbook computers, subnotebook computers, smartphones, music players, personal digital assistants (PDAs), and handheld video game systems. Suitable mobile web browsers include, by way of non-limiting examples, Google® Android® browser, RIM BlackBerry® Browser, Apple® Safari®, Palm® Blazer, Palm® WebOS® Browser, Mozilla® Firefox® for mobile, Microsoft® Internet Explorer® Mobile, Amazon® Kindle® Basic Web, Nokia® Browser, Opera Software® Opera® Mobile, and Sony® PSP™ browser.

Software Modules

In some embodiments, the platforms, systems, media, and methods disclosed herein include software, server, and/or database modules, or use of the same. In view of the disclosure provided herein, software modules are created by techniques known to those of skill in the art using machines, software, and languages known to the art. The software modules disclosed herein are implemented in a multitude of ways. In various embodiments, a software module comprises a file, a section of code, a programming object, a programming structure, or combinations thereof. In further various embodiments, a software module comprises a plurality of files, a plurality of sections of code, a plurality of programming objects, a plurality of programming structures, or combinations thereof. In various embodiments, the one or more software modules comprise, by way of non-limiting examples, a web application, a mobile application, and a standalone application. In some embodiments, software modules are in one computer program or application. In other embodiments, software modules are in more than one computer program or application. In some embodiments, software modules are hosted on one machine. In other embodiments, software modules are hosted on more than one machine. In further embodiments, software modules are hosted on cloud computing platforms. In some embodiments, software modules are hosted on one or more machines in one location. In other embodiments, software modules are hosted on one or more machines in more than one location.

Databases

In some embodiments, the platforms, systems, media, and methods disclosed herein include one or more databases, or use of the same. In various embodiments, suitable databases include, by way of non-limiting examples, relational databases, non-relational databases, object oriented databases, object databases, entity-relationship model databases, associative databases, and XML databases. Further non-limiting examples include SQL, PostgreSQL, MySQL, Oracle, DB2, and Sybase. In some embodiments, a database is internet-based. In further embodiments, a database is web-based. In still further embodiments, a database is cloud computing-based. In other embodiments, a database is based on one or more local computer storage devices.

Platforms for Evaluating Behavioral Disorders, Developmental Delays, and Neurologic Impairments In some embodiments, disclosed herein are platforms for evaluating behavioral disorders, developmental delays, and neurologic impairments comprising one or more computing devices each with an application that allows communication and/or sharing of data between the one or more computing devices. In some embodiments, an application provides a user a specialized portal such as, for example, a healthcare provider portal and a patient portal. Features provided by the applications on the platform described herein include recording an individual and evaluating the individual using the techniques described herein.

In some embodiments, a user records a video of an individual to be evaluated through the use of a recording application on a first user application on a first computing device. In some embodiments, the user application provides direction as to the user on the type and length of recording. In some embodiments, the recording is of the individual moving, responding to questions or requests, eating, emoting, sleeping, playing, conversing, watching (e.g. television), responding to or going about their business.

In some embodiments, the recording analyzed by a machine learning software module that provides probability scores for each possible diagnosis to a clinician through the use of a clinician application. In some embodiments, a probability score must rise above a numerical threshold to be displayed in the clinician application. In some embodiments, probability scores that fall below a specified threshold are displayed in a separate tab or screen in the clinician application. In some embodiments, the clinician reviews the results of the analysis and requests additional data through the clinician's application. For example, a clinician may receive results that a child has a probability score of 35% for a type of autism, a probability score of 48% for a type of mental retardation, and a probability score of 10% for a speech disorder. The probability score threshold is set to 25%, and the clinician reviews the scores for autism and mental retardation. The clinician orders behavioral tests through the application and requests an additional video of the child performing tasks that are indicative of one or both indications. In some embodiments, the clinician diagnoses the individual with the aid of the results provided by the machine learning algorithm. In some embodiments, the clinician inputs the diagnosis into the application and the data and diagnosis is available to a health care provider.

In some embodiments, the healthcare provider is able to coordinate the treatment of the individual and provide advice for treatment to the user and individual. In some embodiments, the individual's treating clinicians in the network of the healthcare provider are able to access the recordings and diagnostic tests.

EXAMPLES

Example 1

A parent is concerned that their 2-year-old child has missed several developmental milestones and reaches out to a clinician to assess the child for any developmental delays. The clinician request that the parent downloads an application on the parent's smartphone and take a video of the child responding to questions, playing with an adult, and playing alone. The application provides guidance regarding the filming of the child with respect to angle of filming, distance of filming, and lighting considerations. The parent takes the videos through the application and also enters in personal information about the child such as sex, date of birth, and type of activity being filmed. The videos are sent to the clinician and automatically analyzed by one or more machine learning algorithms. The clinician is given a probability score for the diagnosis of a developmental delay. The clinician reviews the higher order behaviors and behavioral patterns detected by the one or more machine learning algorithms and confirms that the data used for the diagnosis is clinically relevant. The clinician may order an additional test to confirm the proposed diagnosis. The physician and parent meet to discuss the diagnosis and treatment. The clinician is able to point to specific behaviors in the videos and show the parent the observed behavior. The clinician provides treatment advice and requests that videos are taken at specified intervals to monitor progress of the child and the effectiveness of the proposed treatment. The clinician may change treatment if progress is not seen. The clinician may receive alternative proposed diagnoses following the analysis of subsequent videos and prescribe additional testing or treatment.

Example 2

A child displays a number of behaviors that are symptomatic of a both autism and ADHD. The one or more machine learning algorithms described herein analyze video recordings of the child. The machine learning algorithms are able to recognize behavior units, higher order behaviors and behavioral patterns that are unique to each of the two diagnoses but are difficult to recognize with the human eye. The one or more machine learning algorithms provide a probability score for each of the two diagnoses, finding that the child is very likely to have ADHD and unlikely be autistic.

Example 3

A parent is concerned that their 2-year-old child has missed several developmental milestones and reaches out to a clinician to assess the child for any developmental delays. The clinician requests that the parent download an application on the parent's smartphone and help the child engage in interactive activities provided in the application. The interactive activities provide digital therapy in the form of facilitating and improving the child's speech and language development while also continuously assessing the child based on input data gathered from the child's engagement with the activities. The application provides a virtual character that offers guidance regarding the activities and engages the child by asking questions or providing prompts to elicit feedback or response from the child.

The application performs an in-home automated assessment for speech and language development in young children by providing an interactive module for a variety of interactive digital activities for children to engage in. The parent turns on the software application on the tablet and selects a storybook reading activity for the child. The story book reading activity provides a digital character who provides guidance (see FIG. 5A). The child is presented with a story sequence and corresponding text accompanying the story sequence (see FIG. 5A). After the story sequence is complete, the digital character may ask the child questions about the story sequence to evaluate the child's story comprehension (FIG. 5C).

Figure 6A:
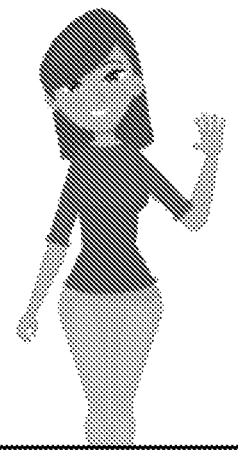
FIG. 6A shows a non-limiting illustration of a graphical display with a virtual character providing instructions to a user during an activity.
Figure 6B:
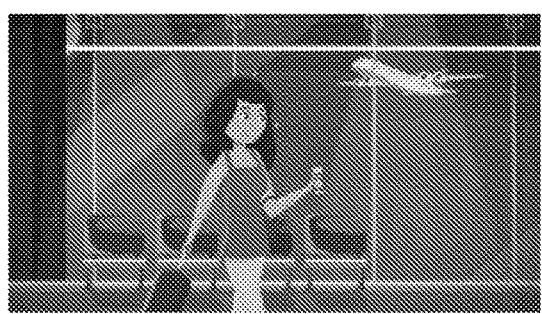
FIG. 6B shows a non-limiting illustration of a graphical display with a story sequence corresponding to a story.
Figure 6B:
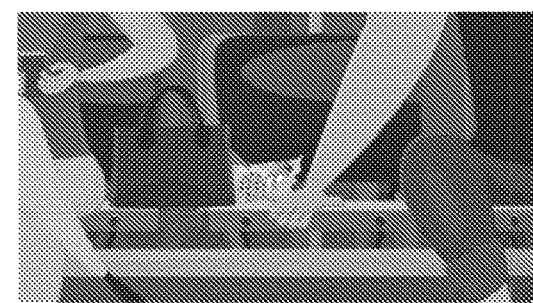
Figure 6B:
Figure 6B:
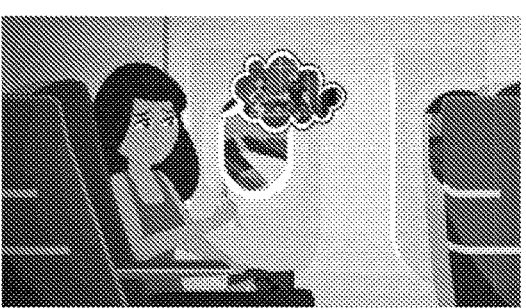

Next, the digital character asks the child to tell the story to their parents, thereby testing the child's ability for story retelling (see FIG. 6A). Visual sequences from the story are shown in FIG. 6B, and the child's retelling of the story is analyzed to determine his proficiency in retelling the sequences. The digital character may also ask the child to come up with a story based on a picture prompt and evaluate the child's response to determine proficiency for providing a picture-elicited narrative (see FIGS. 7A and 7B).

Figure 8:
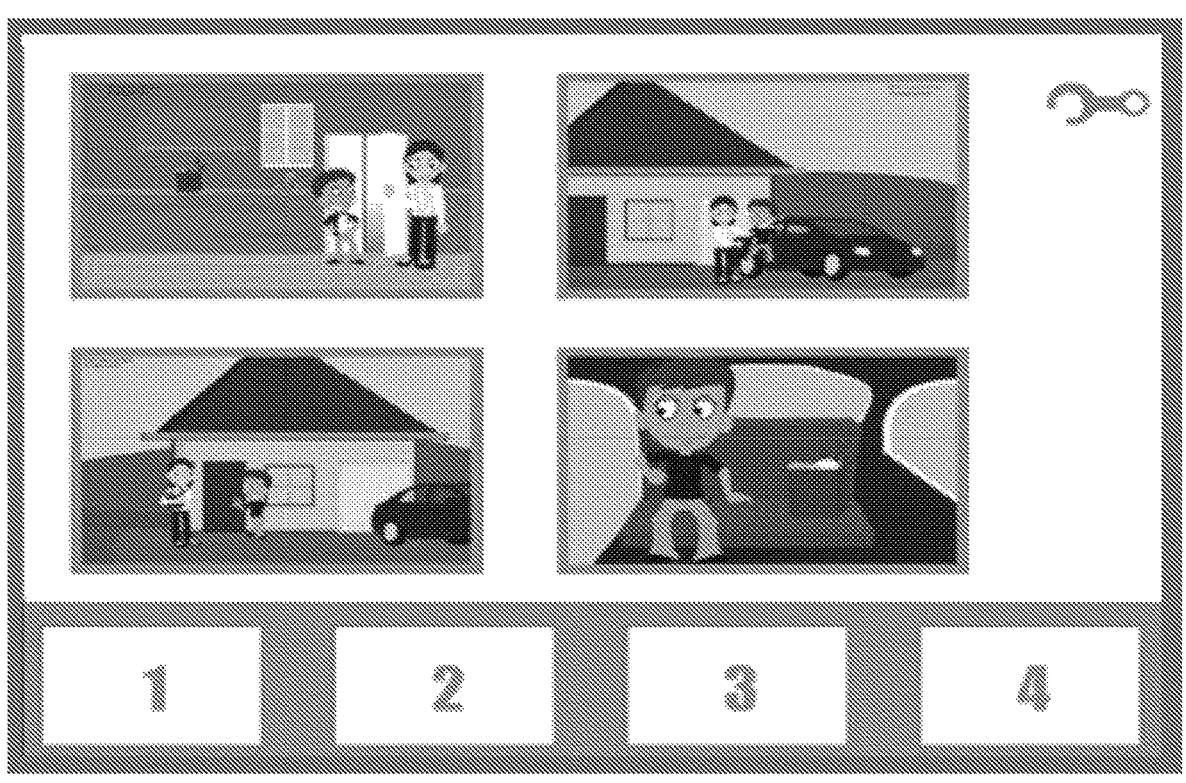
FIG. 8 shows a non-limiting illustration of a graphical display with a series of images for a user to arrange into the correct story sequence.
Figure 9:
FIG. 9 shows a non-limiting illustration of a graphical display with an interface for a user to create a story or narrative.
Figure 10:
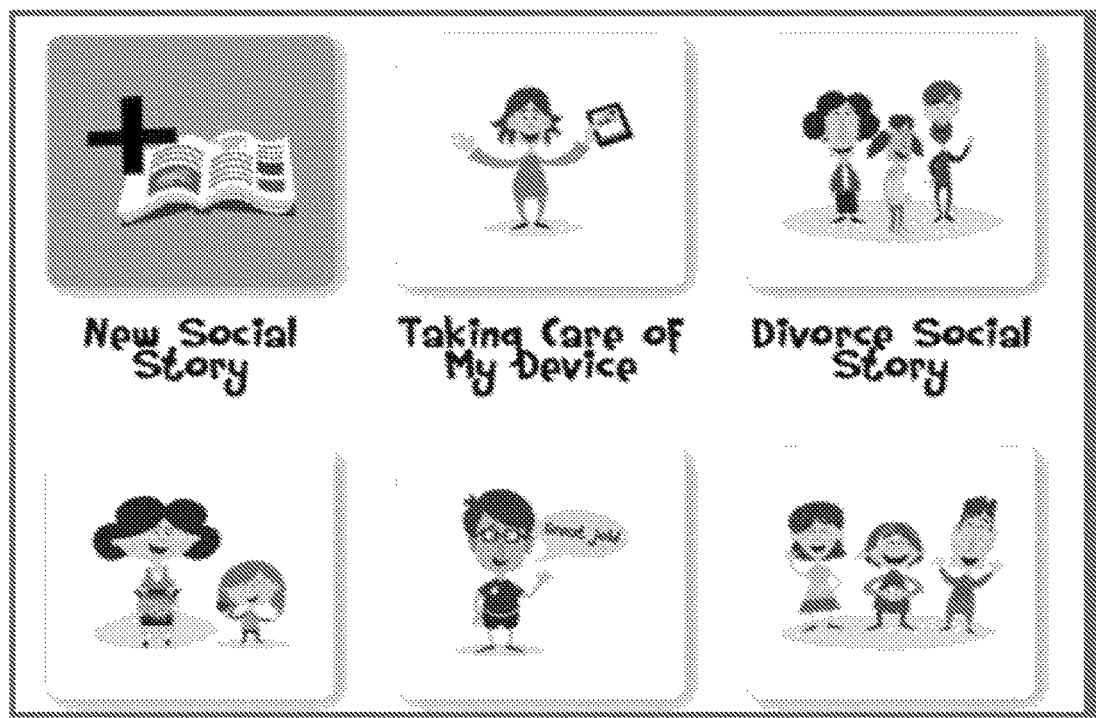
FIG. 10 shows a non-limiting illustration of a graphical display with an activity that provides embedding intervention through social stories.

Additional activities provided by the interactive module can include coloring in an uncolored picture or image, manipulating story sequences (e.g., putting sequences in the correct numbering order or alternatively coming up with a new sequence order; see FIG. 8), and/or personalizing storytelling by allowing a child to create their own story through manipulating and/or arranging story sequences, characters, objects, colors, or other visual elements (see FIG. 9). The personalized storytelling can include manipulation and arrangement of audio sequences as well, for example, matching audio sequences or clips to visual story sequences. As an example, a child is presented with a graphic user interface through the application that has interactive selectable buttons for adding, removing, enlarging/shrinking, moving, coloring, or editing various virtual objects (e.g., characters, animals, tools, clothing, vehicles, buildings, and other objects). Text or dialogue can also be inserted along with corresponding audio clips.

Figure 11:
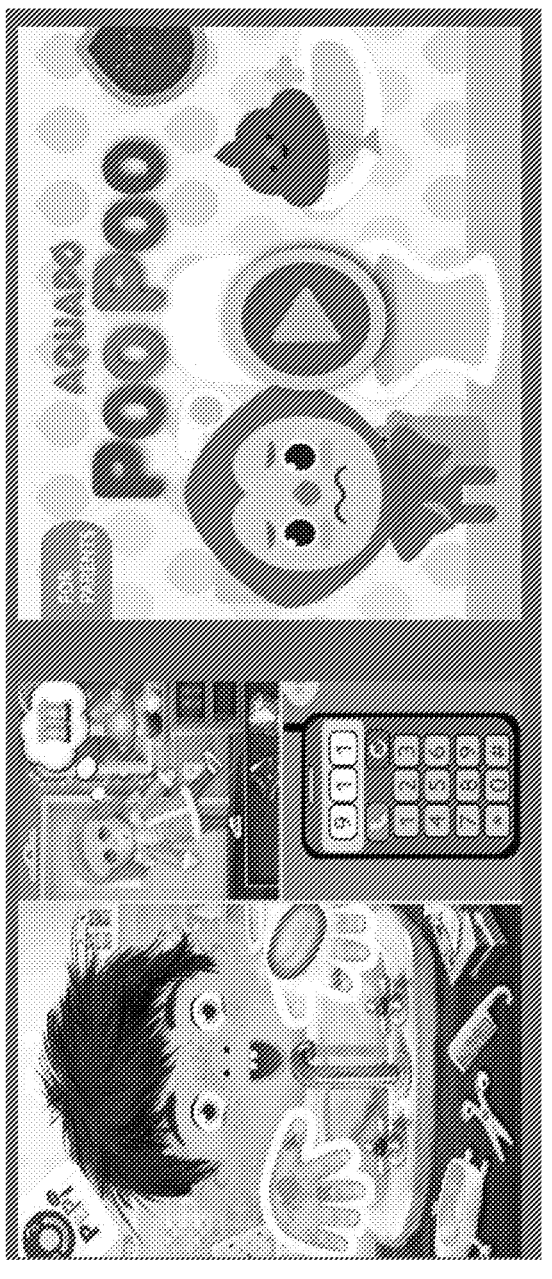
FIG. 11 shows a non-limiting illustration of a graphical display with an activity that provides game-based life skill training.
Figure 12A:
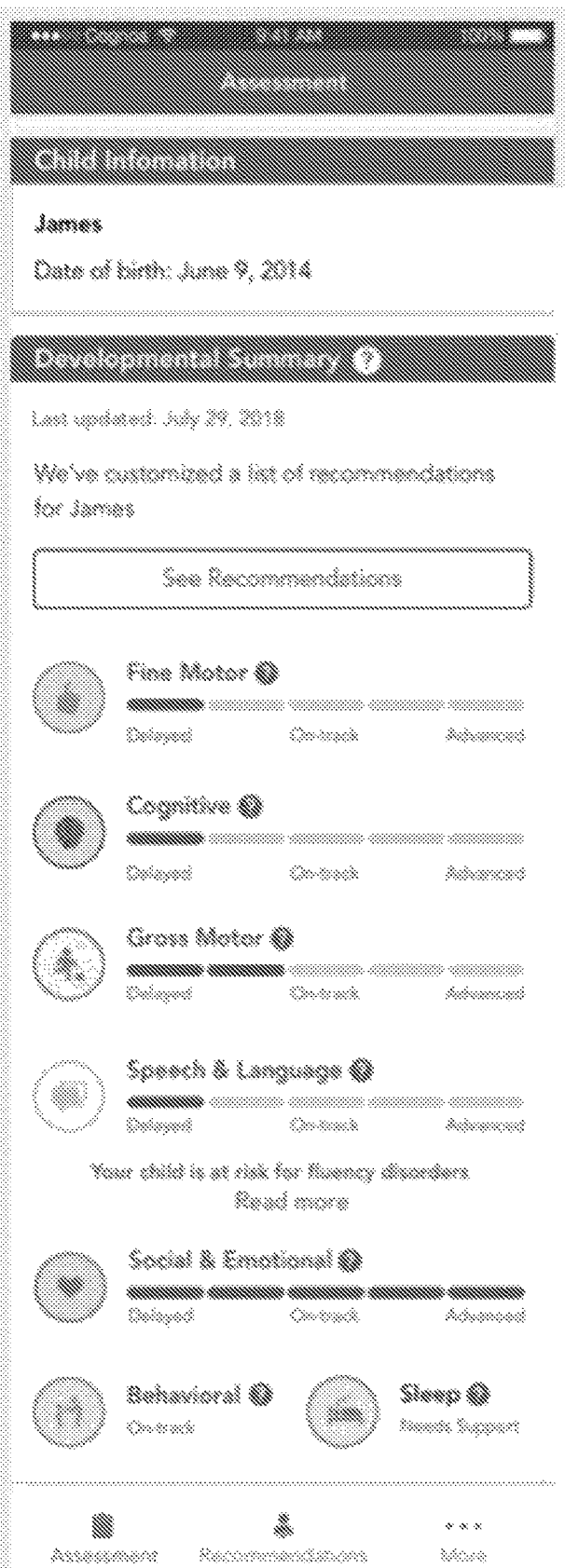
FIG. 12A, FIG. 12B, and FIG. 12C show non-limiting illustrations of a graphical display with the results of an assessment.
Figure 12B:
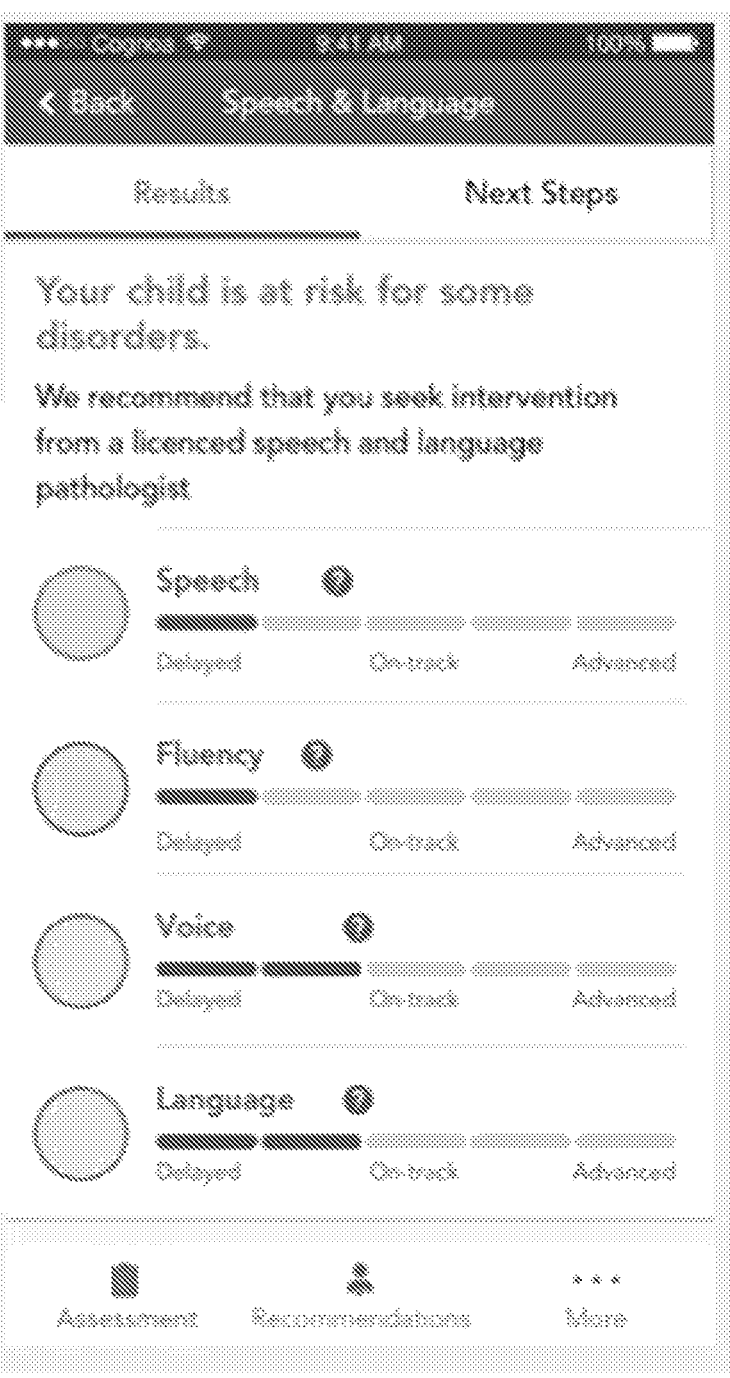
Figure 12C:
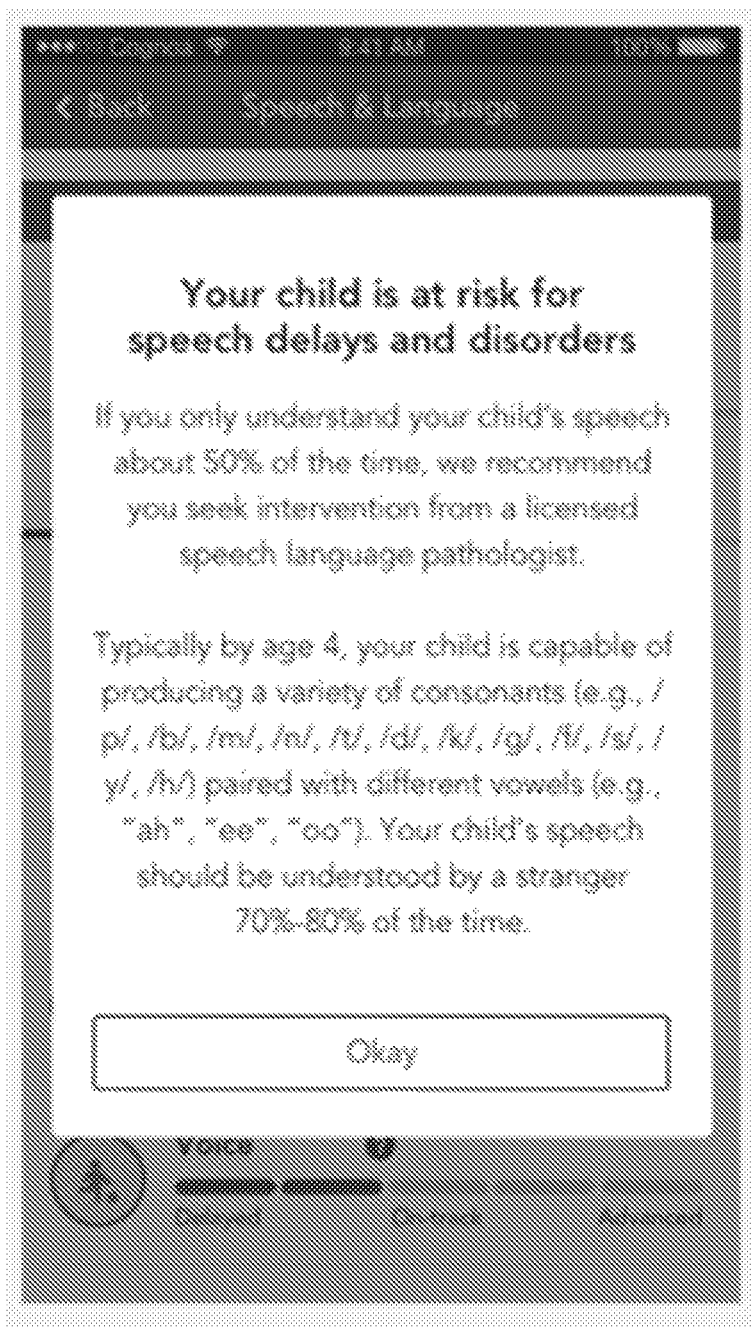

Additional activities provided by the interactive module can include embedding intervention through social stories (see FIG. 10) or game-based life skill training (see FIG. 11).

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A computer-implemented method for automated audio or video assessment of an individual, said method comprising:

(a) providing a storytelling activity to said individual using a story told through one or more images shown via a user interface on a display of a computing device;

(b) receiving, via said user interface on said display of said computing device, feedback from said individual while said individual is provided said storytelling activity in (a), said feedback corresponding to said story of said storytelling activity;

(c) changing said story of said storytelling activity responsive to said feedback received from said individual in (b), thereby generating a changed story of said storytelling activity told through one or more changed images shown via said user interface on said display of said computing device;

(d) providing said storytelling activity having said changed story told through said one or more changed images shown via said user interface on said display of said computing device, wherein said storytelling activity is configured to elicit a plurality of behavioral units in said individual;

(e) receiving, with said computing device, input data comprising at least one of audio information of said individual or video information of said individual, wherein said input data is received from said individual in response to providing said storytelling activity having said changed story in (d);

(f) identifying, with said computing device, said plurality of behavioral units within said input data, wherein each behavioral unit of said plurality of behavioral units comprises a behavior that makes up a higher order behavior; and (g) identifying, with said computing device, said higher order behavior based at least in part on at least one behavioral unit from said plurality of behavioral units.

2. The method of claim 1, wherein at least one of said plurality of behavioral units comprises a facial movement by said individual, a body movement by said individual, or a sound made by said individual.

3. The method of claim 1, wherein said higher order behavior comprises a verbal communication or a non-verbal communication.

4. The method of claim 3, wherein said non-verbal communication comprises a facial expression, posture, gesture, eye contact, or touch.

5. The method of claim 1, wherein said input data comprises said video information for said individual, and wherein identifying said higher order behavior in (g) comprises analyzing said video information using facial recognition to detect one or more facial movements.

6. The method of claim 1, wherein said input data comprises said audio information for said individual, and wherein identifying said higher order behavior in (g) comprises analyzing said audio information using audio recognition to detect one or more sounds, words, or phrases.

7. The method of claim 1, wherein identifying said higher order behavior comprises generating a timeline of said plurality of behavioral units.

8. The method of claim 7, further comprising generating a behavioral pattern based at least in part on said timeline of said plurality of behavioral units or said higher order behavior.

9. The method of claim 1, wherein said input data further comprises information or responses provided by a caretaker of said individual, wherein said information or responses comprise answers to questions.

10. The method of claim 1, further comprising generating a prediction comprising a positive classification, a negative classification, or an inconclusive classification with respect to one or more of: a behavioral disorder, a developmental delay, or a neurologic impairment.

11. The method of claim 1, further comprising obtaining said at least one of said audio information for said individual or said video information for said individual through a mobile computing device, wherein said mobile computing device comprises a smartphone, tablet computer, laptop, smartwatch or other wearable computing device.

12. The method of claim 11, wherein obtaining said at least one of said audio information for said individual or said video information for said individual comprises capturing one or both of video footage or an audio recording, wherein said one or both of said video footage or said audio recording correspond to one or both of said individual or interactions between a person and said individual.

13. The method of claim 10, wherein said one or more of a behavioral disorder, a developmental delay, or a neurologic impairment comprises one or more of: pervasive development disorder (PDD), autism spectrum disorder (ASD), social communication disorder, restricted repetitive behaviors, interests, and activities (RRBs), autism ("classical autism"), Asperger's Syndrome ("high functioning autism"), PDD-not otherwise specified (PDD-NOS, "atypical autism"), attention deficit disorder (ADD), attention deficit and hyperactivity disorder (ADHD), speech and language delay, obsessive compulsive disorder (OCD), depression, schizophrenia, Alzheimer's disease, dementia, intellectual disability, or learning disability.

14. The method of claim 1, wherein identifying said higher order behavior is performed using a machine learning software module.

15. The method of claim 14, wherein said machine learning software module is selected from nearest neighbor, naive Bayes, decision tree, linear regression, support vector machine, or neural network.

16. The method of claim 1, wherein said storytelling activity provides a virtual character guiding said individual through said story.

17. The method of claim 1, wherein said higher order behavior comprises one or more of: articulation of speech sounds, fluency, voice, ability to understand and decode language, or ability to produce and use language.

18. The method of claim 1, further comprising: dynamically modifying at least part of said story of said storytelling activity based at least in part on said input data.

19. The method of claim 1, wherein said story of said storytelling activity comprises an interactive story.

* * * * *